(12) United States Patent
Kriesel et al.

(10) Patent No.: US 7,767,810 B2
(45) Date of Patent: *Aug. 3, 2010

(54) MACROCYCLIC MODULES COMPRISING LINKED CYCLIC SYNTHON UNITS FOR USE IN THE FORMATION OF SELECTIVELY PERMEABLE MEMBRANES

(75) Inventors: Joshua W. Kriesel, San Francisco, CA (US); Timothy B. Karpishin, Castro Valley, CA (US); Donald B. Bivin, Oakland, CA (US); Grant Merrill, San Francisco, CA (US); Martin S. Edelstein, Foster City, CA (US); Thomas H. Smith, San Carlos, CA (US); Jeffery A. Whiteford, Belmont, CA (US); Robert T. Jonas, Palo Alto, CA (US)

(73) Assignee: Covalent Partners, LLC, Hayward, CA (US)

( * ) Notice: Subject to any disclaimer, the term of this patent is extended or adjusted under 35 U.S.C. 154(b) by 922 days.

This patent is subject to a terminal disclaimer.

(21) Appl. No.: 11/199,913

(22) Filed: Aug. 8, 2005

(65) Prior Publication Data

US 2006/0128680 A1 Jun. 15, 2006

Related U.S. Application Data

(63) Continuation of application No. 10/226,400, filed on Aug. 23, 2002, now abandoned, which is a continuation-in-part of application No. 10/071,377, filed on Feb. 7, 2002, now abandoned.

(51) Int. Cl.
C07D 487/00 (2006.01)
(52) U.S. Cl. .................................................. 540/471
(58) Field of Classification Search .................. None
See application file for complete search history.

(56) References Cited

U.S. PATENT DOCUMENTS

| | | |
|---|---|---|
| 3,847,949 A | 11/1974 | Pedersen et al. |
| 4,031,111 A | 6/1977 | Pedersen et al. |
| 4,438,251 A | 3/1984 | Herweh |
| 4,554,076 A | 11/1985 | Speaker |
| 4,828,917 A | 5/1989 | Wegner et al. |
| 4,948,506 A | 8/1990 | Lonsdale et al. |
| 5,059,510 A | 10/1991 | Jones, Jr. et al. |
| 5,143,784 A | 9/1992 | Mita |
| 5,196,257 A | 3/1993 | Barraud et al. |
| 5,342,934 A | 8/1994 | Still et al. |
| 5,357,029 A | 10/1994 | Takekoshi et al. |
| 5,384,168 A | 1/1995 | Dübal et al. |
| 5,405,550 A | 4/1995 | Michl et al. |
| 5,405,552 A | 4/1995 | Jüngbauer et al. |
| 5,622,945 A | 4/1997 | Sessler et al. |
| 5,702,777 A | 12/1997 | Rösch et al. |
| 5,831,087 A | 11/1998 | Haubs et al. |
| 5,876,830 A | 3/1999 | Michl et al. |
| 5,883,246 A | 3/1999 | Brückner et al. |
| 6,033,773 A | 3/2000 | Yang et al. |
| 6,045,821 A | 4/2000 | Garrity et al. |
| 6,210,551 B1 | 4/2001 | Osman et al. |
| 6,262,257 B1 | 7/2001 | Gale et al. |
| 6,380,347 B1 | 4/2002 | Lau et al. |
| 7,368,564 B2 | 5/2008 | Whiteford et al. |
| 2002/0026047 A1 | 2/2002 | Gale et al. |
| 2003/0199688 A1 | 10/2003 | Kriesel et al. |
| 2004/0034223 A1 | 2/2004 | Karpishin et al. |
| 2004/0106741 A1 | 6/2004 | Kriesel et al. |
| 2004/0260085 A1 | 12/2004 | Kriesel et al. |
| 2005/0154199 A1 | 7/2005 | Whiteford et al. |
| 2006/0041077 A1 | 2/2006 | Kriesel et al. |
| 2006/0128680 A1 | 6/2006 | Kriesel et al. |
| 2006/0270846 A1 | 11/2006 | Karpishin et al. |

FOREIGN PATENT DOCUMENTS

DE 196 36 337 A1 3/1998

(Continued)

OTHER PUBLICATIONS

U.S. Appl. No. 12/077,734, filed Mar. 2008, Whiteford et al.*
Korupoju et al. Chemical Communications, 1998, 12, 1267-68.*
Korupoju et al. Chemical Communication, 1998, 1267-68.*
Dorwald Side Reactions in Organic Synthesis, 2005, p. IX of preface.*

(Continued)

Primary Examiner—James O Wilson
Assistant Examiner—Noble Jarrell
(74) Attorney, Agent, or Firm—Finnegan, Henderson, Farabow, Garrett & Dunner, LLP

(57) ABSTRACT

Certain macrocyclic modules comprising 3-24 synthons are provided herein. Each synthon is independently selected from cyclic substituents, wherein each synthon selected is bonded to the next through a linker to form a closed ring that defines a pore. One or more lipophilic moieties and one or more hydrophilic moieties are bonded to one or more of the synthons, resulting in the formation of the desired macrocyclic modules. Those modules may be subsequently linked to one another to form selectively-permeable membranes. Membranes comprising macrocyclic modules may be useful in filtering certain molecular species from a solution. Selective passage of particular species is determined, in part, by the size of the module's pore and the nature of the lipophilic/hydrophobic species attached thereto. Also provided are methods of making and using macrocyclic modules and membranes.

11 Claims, 4 Drawing Sheets

FOREIGN PATENT DOCUMENTS

| | | |
|---|---|---|
| DE | 196 46 537 A1 | 5/1998 |
| SU | 1139730 | 2/1985 |
| SU | 1139731 | 2/1985 |
| SU | 1266849 | 10/1986 |
| SU | 1532560 | 12/1989 |
| WO | WO 92/12708 | 8/1992 |
| WO | WO 95/11449 | 4/1995 |
| WO | WO 96/39402 | 12/1996 |
| WO | WO 97/37995 | 10/1997 |
| WO | WO 99/51570 | 10/1999 |
| WO | WO 03/066646 A1 | 8/2003 |
| WO | WO 03/067286 A1 | 8/2003 |

OTHER PUBLICATIONS

Akine et al., "Synthesis and Crystal Structure of a Novel Triangular Macrocyclic Molecule, Tris(H2saloph), and its Water Complex," *Tetrahedron Letters* 42:8861-8864 (2001).

Alston et al., "Second Sphere Coordination of Tetraammineplatinum(II) by a Macropolycyclic Crown Ether Bisamide Receptor," *Angew. Chem. Int. Ed Engl.* 26(7):692-693 (1987).

Arslanov, V.V., "Monolayers and Langmuir-Blodgett Films of Monomers and Polymers Polyreactions, Structural Transformations, Properties and Applications," *Advances in Colloid and Interface Science* 40:307-370 (1992).

Asfari et al., "Synthesis and Properties of Double-Calix[4]arenes, Doubly-Crowned Calix[4]arenes, and Double-Calix-Crowns," *Pure & Appl. Chem.* 65(3):585-590 (1993).

Baguley et al., "Heterocyclic Imines and Amines. Part VIII. Identification of "o-Cyanothiobenzamide" as 1-Imino-3-Thioisoindoline, and its Conversion With Amines Into Macrocycles and Intermediates," *The Journal of the Chemical Society* Part I: 709-719 (1957).

Belanger et al., "Chloroplast Biogenesis—47:Spectroscopic Study of Net Spectral Shifts Induced by Axial Ligand Coordination in Metalated Tetrapyrroles," *Spectrochim. Acta*, 40A(9):807-827 (1984).

Böhmer V., "Calixarenes, Macrocycles With (Almost) Unlimited Possibilities," *Angew Chem. Eng. Int. Ed.* 34(7):713-745 (1995).

Busch et al., "Molecular Template Effect: Historical View, Principles, and Perspectives" Chapter 1 *In Compr. Supremol. Chem.* Atwood, J.L. et al. eds. *Elsevier Science Inc.*: New York, NY 9:1-43 (1996).

Chadim et al., "(3+3)-Cyclocondensation of the Enantiopure and Racemic Forms of *Trans*-1, 2-Diaminocyclohexane with Terephthaldehyde. Formation of Diasteromeric Molecular Triangles and Their Stereoselective Solid-State Stacking into Microporous Chiral Columns," *Tetrahedron: Asymmetry* 12:127-133 (2001).

Conner et al., "Perforated Monolayers," *Advanced Materials* 6(11):872-874 (1994).

Conner et al., "Perforated Monolayers: Fabrication of Calix[6]arene-Based Composite Membranes That Function as Molecular Sieves," *Langmuir* 9:2389-2397 (1993).

Dutta et al., "Stoichiometric and Metal-Deficient Copper (II) Complexes of a Dinucleating Macrocyclic Ligand. Structural Studies," *Inorg. Chem.* 37(19):5029-5032 (1998).

Endo et al., "Synthesis of Novel Peptidomimetics, Cyclic Hexamers of Unnatural Amino Acids, 2,5-Disubstituted 3-Aminobenzoic Acids," *Heterocycles* 51(2):337-344 (1999).

Gawronski et al., "Designing Large Triangular Chiral Macrocycles Efficient [3 +3] Diamine-Dialdehyde Condensations Based on Conformational Bias," *J. Org. Chem.* 65:5768-5773 (2000).

Hendel et al., "Extraordinary Cohesiveness of a Boronic Acid-Based Calix[6]arene Monolayer at the Air-Water Interface," *Langmuir* 12(23):5745-5746 (1996).

Hendel et al., "Insight Into The Fabrication Of Highly Permselective Polymer/Surfactant Composite Membranes," *Polymeric Materials Science and Engineering (PMSE) Proceedings of the American Chemical Society, Division of Polymeric Materials, Science and Engineering*, (Sep. 8-11, 1997) Las Vegas: NV 77:318-319 (1997).

Höger et al., "High-Yield Macrocyclization via Glaser Coupling of Temporary Covalent Templated Bisacetylenes," *J. Org. Chem.* 62:4556-4557 (1997).

Höger et al., "Shape-Persistent Macrocycles: Building Blocks for Comply Organic and Polymeric Architectures," *Macromol. Symp.* 177:185-191 (2002).

Höger et al., "Solvent Triggering Between Conformational States in Amphiphilec Shape-Persistent Macrocycles," *JACS.* 124(23):6734-6736 (2002).

Höger et al., "Template-Direoted Synthesis of Shape-persistent Macrocyclic Amphiphiles with Convergently Arranged Functionalities," *Chem. Eur. J.* 5(6):1686-1691 (1999).

Höger S., "Highly Efficient Template-Based Preparation of Shape-Persistent Macrocyclics," *Macromol. Symp.* 142:185-191 (1999).

Holliday et al., "Strategies for the Construction of Supramolecular Compounds Through Coordination Chemistry," *Angew. Chem. Int. Ed.* 40(11):2022-2043 (2001).

Hosokawa et al., "8,16,24,32,40,48-Hexamethoxy[$2_6$]Metacyclophane-1,9,17,25,33,41-Hexayne: A Novel Near Planar Ammonium-Selective Ionophore," *Chem. Commun.* 1948-1949 (2001).

Ishida et al., "Molecular Design and Synthesis of Artifical Ion Channels Based on Cyclic Peptides Containing Unnatural Amino Acids," *J. Org. Chem.* 66(9):2978-2989 (2001).

Ito et al., "Syntheses of Chiral Homoazacalix[4]arenes Incorporating Amino Acid Residues: Molecular Recognition for Racemic Quaternary Ammonium Ions," *J. Org. Chem.* 67(21):7519-7522 (2002).

Kim et al., "$CaCl_3$ or $Ca_2Cl_4$ Complexing Cyclic Aromatic Amide. Template Effect on Cyclization," *J. Am. Chem. Soc.* 118(6):1545-1546 (1996).

Kim et al., "Pyrene-Armed Calix[4]azacrowns as New Fluorescent Ionophores: "Molecular Taekowndo" Process via -Fluorescence Change," *J. Org. Chem.* 67:2348-2351 (2002).

Kon et al., "Synthesis of Macrocyclic Cage Compounds by Diamine-Dihalide One-Step Coupling-Reaction," *J. Org. Chem.* 65:3708-3715 (2000).

Korupoju et al., Formation of Dinuclear Macrocyclic And Mononuclear Acyclic Complexes of a New Trinucleating Hexaaza Triphenoiic Schiff Base Macrocycle: Structure and NLO Properties, *J. Chem. Soc. Dalton Trans.* pp. 2845-2852 (2000).

Korupoju et al., "New Optically Active Hexaaza Triphenolic Macrocycles: Synthesis, Molecular Structure and Crystal Packing Features," *Chemical Communications* 12:1267-1268 (1998).

Kraft et al., "Regioselective Synthesis of Calixcrowns Derived From p-tert-Butylcalix[5]arene," *Tetrahedron* 49(27):6019-6024 (1993).

Kuhnert et al., "Synthesis of Novel Chiral Non-Racemic Substituted Trianglimine and Trianglamine Macrocycles," *Tetrahedron Letters* 43:3329-3332 (2002).

Kuhnert et al., "Synthesis of Novel Enantiomerically Pure Trianglimine and Trianglamine Macrocycles," *Tetrahedron: Asymmetry* 13:123-128 (2002).

Kuroda et al., "Syntheses and Redox Behavior of Novel Cyclic Hosts Having Multiple Redox Centers of NAD+ Analogue," *Tetrahedron Letters* 38:3939-3942 (1997).

Lee et al., "Membrane Composites Derived from Porous Versus Nonporous Surfactants: Evidence for Uniqueness of Calix[6]arene-Based Surfactants," *J. Am. Chem. Soc.* 117(25):6793-6794 (1995).

Lee et al., "Unusual Pressure Effects on the Permeation Properties of a Langmuir-Blodgett Composite Membrane," *J. Am. Chem. Soc.* 117(42)10599-10600 (1995).

Li et al., "Synthesis and Characterization of 'Calixsalens': A New Class of Macrocyclic Chiral Ligands," *Chem. Commun.* pp. 1531-1532 (1999).

Lin et al., "Hydrogen-Bond-Assisted π-Stacking of Shape-Persistent Cyclopbanes," *J. Org. Chem.* 67(21):7761-7768 (2002).

Markowitz et al., "Perforated Monolayers: Design and Synthesis of Porous and Cohesive Monolayers From Mercurated Calix[*n*]arenes," *J. Am. Chem. Soc.* 111(21):8192-8200 (1989).

Markowitz et al., "Perforated Monolayers: Porous and Cohesive Monolayers from Mercurated Calix[6]arenes," *J. Am. Chem. Soc.* 110:7545-7546 (1988).

Mohanta et al., "Macrocyclic $Cu^{II}2$, $Cu^{II}4$, $Ni^{II}3$, and $Ni^{II}4$ Complexes: Magnetic Properties of Tetranuclear Systems," *Inorg. Chem.* 36(21):4656-4664 (1997).

Molina et al., "A Generalized and Efficient Preparation of a Novel Class of Macrocyclic Bis(guanidines) From Cyclic Bis(carbodiimides)," *J. Org.Chem.* 63:2922-2927 (1998).

Morrison et al., "Shape-Persistent Macrocyclic Amphiphiles: Molecular Reversible Coats," *Chem Commun.* 20:2313-2314 (1996).

Murakami et al., "Supramolecular Effects and Molecular Discrimination by Macrocyclic Hosts Embedded in Synthetic Bilayer Membranes," *Proc. Natl. Acad. Sci. USA* 90:1140-1145 (1993).

Nakamoto et al., Langmuir Monolayers of *p*-Octadecylcalix[4]arene, *American Chemical Society*, 5(4):1116-17 (1989).

Notti et al., "Calix[4]-and Calix[5]arene-Based Multicavity Macrocyles," *J. Org. Chem.* 67(21):7569-7572 (2002).

O'Connor et al., "Calixarenes in Electroanalysis," *Electroanalysis* 7(3):205-215 (1995).

Perrin et al., "Industrial Applications of Calixarenes," In *Calixarenes: A Versatile Class of Macrocyclic Compounds*, Vicens, J. et al. eds, 3:235-259 (1991).

Pigge et al., "An Enaminone-Directed Benzannuiation/Macrocyclization Approach to Cyclophane Ring Systems," *J. Org. Chem.* 67(13):4547-4552 (2002).

Qian et al., "Spectroscopic Studies of the Multiporphyrin Arrays at the Air-Water Interface and in Langmuir-Blodgett Films," *Thin Solid Film* 397:266-275 (2001).

Ruaudel-Teixier A., "Supermolecular Architecture in Langmuir-Blodgett Films: Control and Chemistry," *Heterogeneous Chemistry Reviews.* 3:1-15 (1996).

Rudkevich et al., "Calix[4]arene Salenes: A Bifunctional Receptor for $NaH_2PO_4$," *J.Org. Chem.* 59(13):3683-3686 (1994).

Schrader et al., "Towards Synthetic Adrenaline Receptors," *Materials Science & Engineering*, C18:147-155 (2001).

Shetty et al., "Assembly of Amphiphilic Phenylacetylene Macrocycles at the Air-Water Interface and on Solid Surfaces," *J. Am. Chem. Soc.* 118(39):9409-9414 (1996).

Timmerman et al., "A Novel Type of Stereoisomerism in Calix[4]arene-Based Carceplexes," *Angew. Chem.* 33(22):2345-2348 (1994).

Tsukruk V.V., "Assembly of Supramolecular Polymers in Ultrathin Films," *Prog. Polym. Sci.* 22(2):247-311 (1997).

Van der Heyden et al., "Probing Inter- and Intramolecular Interactions of Six New *p-tert*-Butylcalix[4]arene-Based Bipyridyl Podands with Langmuir Monolayers," *Langmuir* 18:8854-8861 (2002).

van Nostrum et al., "Supramolecular Architectures From Phthalocyanine Building Blocks," *Polym. Prepr.* 34(1):164-165 (1993).

van Nostrum et al., "Supramolecular Architectures From Phthalocyanine Building Blocks," *Macromol. Symp.* 77:267-276 (1994).

Wilkop et al., "Smart Structures for Sensing Environmental Pollution," *Proceedings of SPIE-The International Society for Optical Engineering (Smart Electronics and MEMS)*, Mar. 1-3, 1999 Newport Beach, CA 3673:327-334 (1999).

Yan et al., "Selective Dampening of the Gas Permeability of a Langmuir-Blodgett Film Using Moist Permeants," *J. Am. Chem. Soc.* 122:11944-11947 (2002).

Yatsimirskii et al., "Interphase Transport of Iron (III) Chloride by Means of Macrocyclic Ligands," *Theoretical and Experimental Chemistry* 22(10):162-167 with Table of Contents, *A translation of the article published in Teoreticheskaya I Eksperimental naya Khimiya* (Jan.-Feb. 1986) 22(1):174-180 (1986).

Yoshino et al., "An Artificial Ion Channel Formed by a Macrocyclic Resorcin[4]arene With Amphiphilic Cholic Acid Ether Groups," *Angew. Chem. Int. Ed. Engl.* 40(2):457-459 (2001).

Zhao et al., "Synthesis and Self-Association of an Imine-Containing *m*-Phenylene Ethynylene Macrocycle," *J. Org. Chem.* 67(11):3548-3554 (2002).

Foreign language article, "Calixarene-A macrocyclic Compound with Bright Prospect," *Chemical Research and Application*, 2(2):8-21 (1990).

Foreign language article, "Synthesis and Application of Calix[4]pyrrole Macrocyclic Compounds," *Hecheng Huaxue*, 9(5):436-438 (2001).

International Search Report mailed Dec. 18, 2003, issued in PCT Application No. PCT/US03/03830.

International Search Report mailed Feb. 23, 2004, issued in PCT Application No. PCT/US03/03829.

International Search Report mailed Jul. 6, 2005, issued in PCT Application No. PCT/US03/22749.

Supplementary European Search Report mailed May 13, 2005, in European Patent Application No. 03709017.2-1211.

Supplementary European Search Report mailed May 13, 2005, in European Patent Application No. 03709018.0-1211.

Office Action mailed Jan. 23, 2004, in U.S. Appl. No. 10/071,377, filed Feb. 7, 2002.

Office Action mailed Jul. 6, 2004, in U.S. Appl. No. 10/071,377, filed Feb. 7, 2002.

Office Action mailed Apr. 18, 2005, in U.S. Appl. No. 10/071,377, filed Feb. 7, 2002.

Office Action mailed Jan. 23, 2004, in U.S. Appl. No. 10/226,400, filed Aug. 23, 2002.

Office Action mailed Jul. 6, 2004, in U.S. Appl. No. 10/226,400, filed Aug. 23, 2002.

Office Action mailed Apr. 7, 2005, in U.S. Appl. No. 10/226,400, filed Aug. 23, 2002.

Office Action mailed Dec. 19, 2005, in U.S. Appl. No. 10/359,894, filed Feb. 7, 2003.

Office Action mailed Sep. 27, 2006, in U.S. Appl. No. 10/359,894, filed Feb. 7, 2003.

Office Action mailed May 4, 2007, in U.S. Appl. No. 10/359,894, filed Feb. 7, 2003.

Advisory Action mailed Oct. 3, 2007, in U.S. Appl. No. 10/359,894, filed Feb. 7, 2003.

Notice of Allowance mailed Apr. 30, 2008, in U.S. Appl. No. 10/359,894, filed Feb. 7, 2003.

Office Action mailed Dec. 23, 2004, in U.S. Appl. No. 10/426,475, filed Apr. 29, 2003.

Office Action mailed Mar. 10, 2005, in U.S. Appl. No. 10/426,475, filed Apr. 29, 2003.

Office Action mailed Aug. 2, 2007, in U.S. Appl. No. 11/207,383, filed Aug. 18, 2005.

Office Action mailed Feb. 11, 2008, in U.S. Appl. No. 11/207,383, filed Aug. 18, 2005.

Office Action mailed Sep. 26, 2008, in U.S. Appl. No. 11/207,383, filed Aug. 18, 2005.

Office Action mailed Jan. 12, 2006, in U.S. Appl. No. 11/202,322, filed Aug. 10, 2005.

Office Action mailed Jun. 21, 2006, in U.S. Appl. No. 11/202,322, filed Aug. 10, 2005.

Office Action mailed Oct. 12, 2006, in U.S. Appl. No. 11/202,322, filed Aug. 10, 2005.

Office Action mailed Jan. 16, 2007, in U.S. Appl. No. 11/202,322, filed Aug. 10, 2005.

Office Action mailed May 16, 2007, in U.S. Appl. No. 11/202,322, filed Aug. 10, 2005.

Office Action mailed Jan. 11, 2008, in U.S. Appl. No. 11/202,322, filed Aug. 10, 2005.

Office Action mailed Aug. 25, 2008, in U,S. Appl. No. 11/202,322, filed Aug. 10, 2005.

* cited by examiner

US 7,767,810 B2

MACROCYCLIC MODULES COMPRISING LINKED CYCLIC SYNTHON UNITS FOR USE IN THE FORMATION OF SELECTIVELY PERMEABLE MEMBRANES

CROSS REFERENCE TO RELATED APPLICATIONS

This application is a continuation of U.S. patent application Ser. No. 10/226,400, filed on Aug. 23, 2002 now abandoned, which is a continuation in part of U.S. patent application Ser. No. 10/071,377, filed on Feb. 7, 2002 now abandoned, the contents of each of which are incorporated herein by reference in their entirety.

FIELD OF THE INVENTION

This invention is related to the fields of organic chemistry and nanotechnology. In particular, it relates to materials and methods for the preparation of synthons used to construct macrocyclic module compositions.

BACKGROUND OF THE INVENTION

One area of nanotechnology is to develop chemical building blocks from which hierarchical molecules of predicted properties can be assembled. An approach to making chemical building blocks or nanostructures begins at the atomic and molecular level by designing and synthesizing starting materials with highly tailored properties. Precise control at the atomic level is the foundation for development of rationally tailored synthesis-structure-property relationships which can provide materials of unique structure and predictable properties. This approach to nanotechnology is inspired by nature where, for example, from twenty common amino acids found in natural proteins, more than $10^5$ stable and unique proteins are made.

Nanotechnology has also been described by K. Eric Drexler in *Engines of Creation* as "the knowledge and means for designing, fabricating and employing molecular scale devices by the manipulation and placement of individual atoms and molecules with precision on the atomic scale." A quest of nanotechnology is to prepare molecular architectures capable of performing on a nanometer scale functions normally observed for large-scale constructs. For example, rotaxanes and polyrotaxanes are molecules that are interlocked, but not chemically bound to one another, which act like nano-machines. In other examples, carbon nanotubes and similar constructs have been created which may function as molecular scaffold units, or as transport channels, storage units, or encapsulators for various atoms and molecules. The use of biological processes is also being studied as an approach to the assembly of non-biological nano-devices. For example, U.S. Pat. No. 5,468,851 discloses building various structures from polynucleotide segments.

In U.S. Pat. No. 5,876,830 an approach to the construction of macromolecular structures by coupling molecular modules using connectors, spacers, and binders is described. The modules were adhered to a surface and reacted to form grids or nets on the surface.

International Patent Application WO 01/27028 A1 describes structural sub-units or synthons which could be used to prepare molecular nanostructures, machines and devices. Synthons used were closo-carboranes, which are rigid polyhedral structures, selected for their availability and requisite substitutional control and structural diversity.

Some aspects of nanotechnology are described in *Chemical Reviews,* 1999(7).

One field that will benefit from nanotechnology is filtration using membranes. Conventional membranes used in a variety of separation processes can be made selectively permeable to various molecular species. The permeation properties of conventional membranes generally depend on the pathways of transport of species through the membrane structure. While the diffusion pathway in conventional selectively permeable materials can be made tortuous in order to control permeation, porosity is not well defined or controlled by conventional methods. The ability to fabricate regular or unique pore structures of membranes is a long-standing goal of separation technology.

In one example, the formation of selectively permeable membranes of monomolecular thickness was described by Hendel, et al., *Journal of the Amer. Chem. Soc.,* 1997, 119: 6909-18, who reported preparation of calix[6]arenes and their deposition as Langmuir-Blodgett films on a porous poly [1(trimethylsilyl)-1-propyne] substrate, where the calix[6] arene molecules are not coupled or bound to each other in the film. A selectively permeable membrane was described for which the ratio of the normalized flux of helium gas to nitrogen gas was found to significantly exceed the conventional Graham's law prediction.

Resistance to flow of species through a membrane may also be governed by the flow path length. Resistance can be greatly reduced by using a very thin film as a membrane, at the cost of reduced mechanical strength of the membrane material. Conventional membranes may have a barrier thickness of at least one to two hundred nanometers, and often up to millimeter thickness. In general, a thin film of membrane barrier material can be deposited on a porous substrate of greater thickness to restore material strength.

Membrane separation processes are used to separate components from a fluid in which atomic or molecular components having sizes smaller than a certain "cut-off" size can be separated from components of larger size. Normally, species smaller than the cut-off size are passed by the membrane. The cut-off size may be an approximate empirical value which reflects the phenomenon that the rate of transport of components smaller than the cut-off size is merely faster than the rate of transport of larger components. In conventional pressure-driven membrane separation processes, the primary factors affecting separation of components are size, charge, and diffusivity of the components in the membrane structure. In dialysis, the driving force for separation is a concentration gradient, while in electrodialysis electromotive force is applied to ion selective membranes.

Thus, what is needed is an approach to making chemical building blocks or nanostructures from starting materials with tailored properties.

SUMMARY OF THE INVENTION

In one aspect, a macrocyclic module composition is provided which may be made from three to about twenty-four cyclic synthons, provided at least one of the synthons is different from the others. The synthons of the macrocyclic module composition form a closed ring.

In some variations, a macrocyclic module composition may include functional groups for coupling to other macrocyclic modules. A composition may include two or more closed rings coupled together.

In other variations, one or more functional groups may be coupled to one or more of the cyclic synthons of a macrocyclic module composition, the functional group(s) located at the pore of the composition, where the macrocyclic module composition may have a first pore dimension in a first conformation when a first group of substituents is located at the pore and a second pore dimension in a second conformation when a second group of substituents is located at the pore.

In further variations, a composition may include a closed ring, a functional group coupled to the closed ring at the pore, and a selected species to be transported through the pore.

In another aspect, a method is provided to make a composition to transport selected species through the composition, by selecting a first cyclic synthon substituted with at functional group and selecting from two to about twenty-three additional cyclic synthons, then incorporating the cyclic synthons into a macrocyclic module composition in which the functional group of the first cyclic synthon is located at the pore of the composition.

In one variation, a macrocyclic module composition may be coupled to a solid

In one aspect, a macrocyclic module composition is provided having from three to twenty four cyclic synthons forming a closed ring of cyclic synthons which retains film area after a period of time on a Langmuir trough.

In another aspect, a linkage is formed between coupled cyclic synthons.

In another aspect, a method for making a macrocyclic module composition is provided wherein a plurality of a first cyclic synthon is contacted with a plurality of a second cyclic synthon, and the macrocyclic module composition is isolated therefrom. A linker molecule may be contacted with the mixture of synthons.

In another variation, a method for making a macrocyclic module composition is provided wherein a plurality of a first cyclic synthon is contacted with a plurality of a second cyclic synthon, and a plurality of the first cyclic synthon is contacted with the mixture. The first cyclic synthon may be supported on a solid phase.

In another variation, a method for making a macrocyclic module composition is provided wherein a plurality of a first cyclic synthon is contacted with a plurality of a second cyclic synthon, and a plurality of a third cyclic synthon is contacted with the mixture. The first cyclic synthon may be supported on a solid phase.

In another variation, a method for making a macrocyclic module includes a template for bringing together synthons.

DETAILED DESCRIPTION OF THE INVENTION

Synthons for Macrocyclic Modules

Figure 1A:
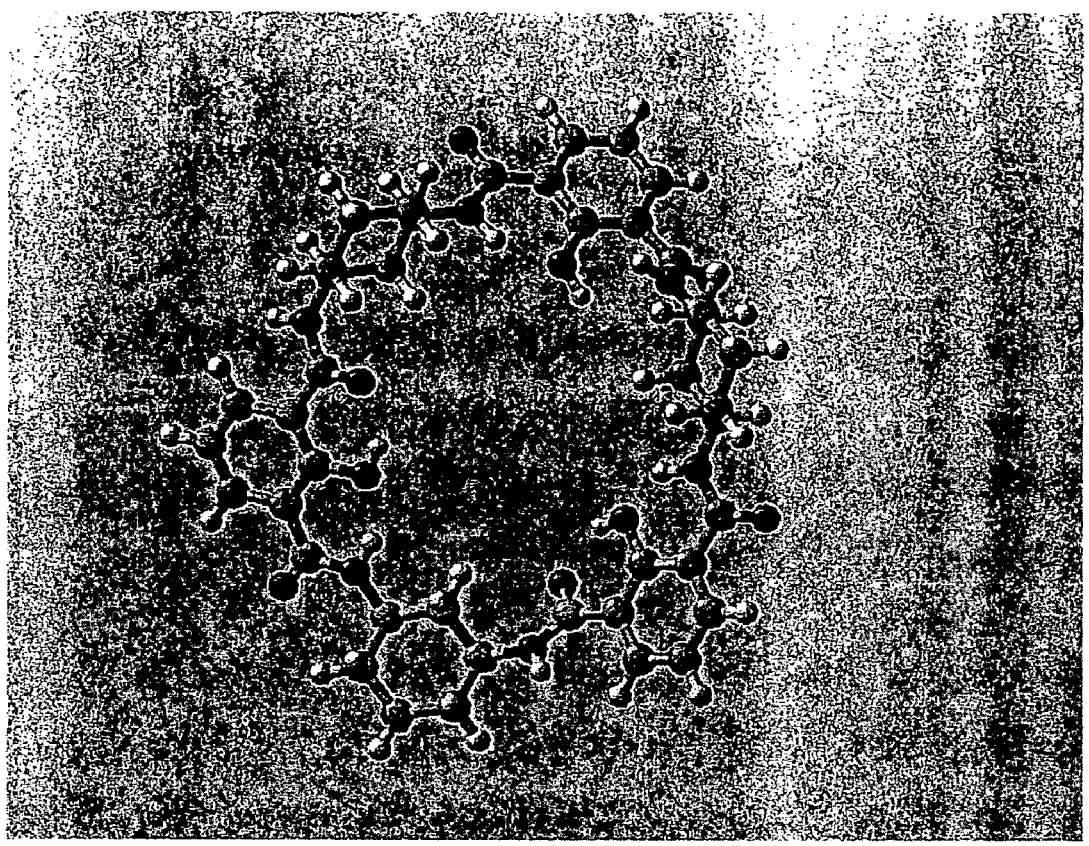
FIG. 1A shows a representation of an example of the structure of an embodiment of a hexamer macrocyclic module.

As used herein, the term "alkyl" refers to a branched or unbranched monovalent hydrocarbon radical. An "n-mC" alkyl or "(nC-mC)alkyl" refers to all alkyl groups containing from n to m carbon atoms. For example, a 1-4C alkyl refers to a methyl, ethyl, propyl, or butyl group. All possible isomers of an indicated alkyl are also included. Thus, propyl includes isopropyl, butyl includes n-butyl, isobutyl and t-butyl, and so on. The term alkyl includes substituted alkyls. As used herein, the term "substituted alkyl" refers to an alkyl group with an additional group or groups attached to any carbon of the alkyl group. Additional groups attached to a substituted alkyl may include one or more functional groups such as alkyl, aryl, acyl, halogen, alkylhalo, hydroxy, amino, alkoxy, alkylamino, acylamino, acyloxy, aryloxy, aryloxyalkyl, mercapto, both saturated and unsaturated cyclic hydrocarbons, heterocycles, and others.

As used herein, the terms "R," "R'," and "R''" in a chemical formula refer to a hydrogen or an organic group, each independently selected, unless stated otherwise.

As used herein, the term "aryl" refers to an aromatic group which may be a single aromatic ring or multiple aromatic rings which are fused together, linked covalently, or linked to a common group such as a methylene, ethylene, or carbonyl, and includes polynuclear ring structures. An aromatic ring or rings may include substituted or unsubstituted phenyl, naphthyl, biphenyl, diphenylmethyl, and benzophenone groups, among others. The term "aryl" includes substituted aryls.

As used herein, the term "heteroaryl" refers to an aromatic ring(s) in which one or more carbon atoms of the aromatic ring(s) are substituted by a heteroatom such as nitrogen, oxygen, or sulfur. Heteroaryl refers to structures which may include a single aromatic ring, multiple aromatic rings, or one or more aromatic rings coupled to one or more nonaromatic rings. It includes structures having multiple rings, fused or unfused, linked covalently, or linked to a common group such as a methylene or ethylene group, or linked to a carbonyl as in phenyl pyridyl ketone. As used herein, the term "heteroaryl" includes rings such as thiophene, pyridine, isoxazole, phthalimide, pyrazole, indole, furan, or benzo-fused analogues of these rings.

As used herein, the term "saturated cyclic hydrocarbon" refers to ring structures cyclopropyl, cyclobutyl, cyclopentyl groups, and others, including substituted groups. Substituents to saturated cyclic hydrocarbons include substituting one or more carbon atoms of the ring with a heteroatom such as nitrogen, oxygen, or sulfur. Saturated cyclic hydrocarbons include bicyclic structures such as bicycloheptanes and bicyclooctanes, and multicyclic structures.

As used herein, the term "unsaturated cyclic hydrocarbon" refers to a monovalent nonaromatic group with at least one double bond, such as cyclopentene, cyclohexene, and others, including substituted groups. Substituents to unsaturated cyclic hydrocarbons include substituting one or more carbon atoms of the ring with a heteroatom such as nitrogen, oxygen, or sulfur. As used herein, the term "cyclic hydrocarbon" includes substituted and unsubstituted, saturated and unsaturated cyclic hydrocarbons, and multicyclic structures. Unsaturated cyclic hydrocarbons include bicyclic structures such as bicycloheptenes and bicyclooctenes, and multicyclic structures.

As used herein, the terms "amphiphile" or "amphiphilic" refer to a species which exhibits both hydrophilic and lipophilic character. In general, an amphiphile contains a lipophilic moiety and a hydrophilic moiety. An amphiphile may form a Langmuir film.

Examples of hydrophilic moieties include, without limitation, hydroxyl, methoxy, phenol, carboxylic acids and salts thereof, methyl and ethyl esters of carboxylic acids, amides, amino, cyano, ammonium salts, monoalkyl-substituted amino groups, di-alkyl-substituted amino groups, —NRR', —N≡C, —NHR, sulfonium salts, phosphonium salts, polyethyleneglycols, polypropyleneglycols, epoxy groups, acrylates, sulfonamides, nitro, —OP(O)(OCH$_2$CH$_2$N$^+$RR'R")O$^-$, guanidinium, aminate, acrylamide, and pyridinium. Such hydrophilic moieties may include groups such as polyethylene glycols, or for example, polymethylene chains substituted with alcohol, carboxylate, acrylate, methacrylate, or

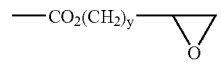

groups, where y is 1-6. Hydrophilic moieties may also include alkyl chains having internal amino or substituted amino groups, for example, internal —NH—, —NC(O)R—, or —NC(O)CH=CH$_2$— groups. Hydrophilic moieties may also include polycaprolactones, polycaprolactone diols, poly(acetic acid)s, poly(vinyl acetates)s, poly(2-vinyl pyridine)s, cellulose esters, cellulose hydroxyl ethers, poly(L-lysine hydrobromide)s, poly(itaconic acid)s, poly(maleic acid)s, poly(styrenesulfonic acid)s, poly(aniline)s, or poly(vinyl phosphonic acid)s.

Examples of lipophilic moieties include, without limitation, linear or branched alkyls, including 1-28C hydrocarbons. The most common example of a lipophilic moiety is a long, straight or branched hydrocarbon chain. Presently preferred lipophilic groups consist of at least (8) carbon atoms in a branched or straight chain. Examples of groups which may be coupled to a synthon or macrocyclic module as a lipophilic group include alkyls, —CH=CH—R, —C≡C—R, —OC(O)—R, —C(O)O—R, —NHC(O)—R, —C(O)NH—R, and —O—R, where R is 4-18C alkyl. As another example, a lipophilic group includes —(8C-28C)alkyl, —O(8C-28C)alkyl, —NH(8C-28C)alkyl, —OC(O)—(8C-28C)alkyl, —C(O)O—(8C-28C)alkyl, —NHC(O)—(8C-28C)alkyl, —C(O)NH—(8C-28C)alkyl, —CH=CH—(8C-28C)alkyl and —C≡C—(8C-28C)alkyl, wherein the carbon atoms of the (8C-28C)alkyl group may be interrupted by one or more —S—, double bond, triple bond or —SiR'R"— groups, substituted with one or more fluorine atoms or any combination of these; R' and R" independently comprise (1C-18C)alkyl. Each chain may independently comprise, without limitation, alkenyl, alkynyl, saturated and unsaturated cyclic hydrocarbons, or aromatic groups. Each chain may also contain, interspersed among the carbons of the chain, one or more silicon atoms substituted with alkyl, alkenyl, alkynyl, saturated and unsaturated cyclic hydrocarbons, or aryl groups. The carbon atoms of each chain may independently be substituted with one or more fluorine atoms. The carbon atoms of an alkyl group may be interrupted by one or more functional groups such as, for example, —S—, double bond, triple bond or —SiR'R"— groups, any of which may be substituted with one or more fluorine atoms, and any combination of such functional groups may be used. R' and R" independently comprise (1C-18C)alkyl.

As used herein, the terms "coupling" and "coupled" with respect to molecular moieties or species, molecules, synthons, and macrocyclic modules refers to their attachment or association with other molecular moieties or species, atoms, molecules, synthons, or macrocyclic modules, whether the attachment or association is specific or non-specific, reversible or non-reversible, is the result of chemical reaction, or the result of direct or indirect physical interactions, complexation, charge transfer, or as the result of magnetic, electrostatic, or electromagnetic interaction. Coupling may be specific or non-specific, and the bonds formed by a coupling reaction are often covalent bonds, or polar-covalent bonds, or mixed ionic-covalent bonds, and may sometimes be Coulombic forces, ionic or electrostatic forces or interactions.

As used herein, the term "functional group" includes, but is not limited to, chemical groups, organic groups, inorganic groups, organometallic groups, aryl groups, heteroaryl groups, cyclic hydrocarbon groups, amino (—NH$_2$), hydroxyl (—OH), cyano (—C≡N), nitro (NO$_2$), carboxyl (—COOH), formyl (—CHO), keto (—CH$_2$C(O)CH$_2$—), alkenyl (—C=C—), alkynyl, (—C≡C—), and halo (F, Cl, Br and I) groups.

In some embodiments, a functional group may be selected from —C(O)F, —C(O)O-4-nitrophenyl, —C(O)O-pentafluorophenyl, —C(O)O—N-hydroxysuccinimide, a lipophilic group, —OH, —C(O)OH, —C(O)H, —C(O)OCH$_3$, —C(O)Cl, —NRR, —NRRR$^+$A$^-$, -MgX, -Li, —OLi, —OK, —ONa, —SH, —C(O)(CH$_2$)$_2$C(O)OCH$_3$, —NH-alkyl-C(O)CH$_2$CH(NH$_2$)CO$_2$-alkyl, —CH=CH$_2$, —CH=CHR, —CH=CR$_2$, 4-vinylaryl, —C(O)CH=CH$_2$, —NHC(O)CH=CH$_2$,

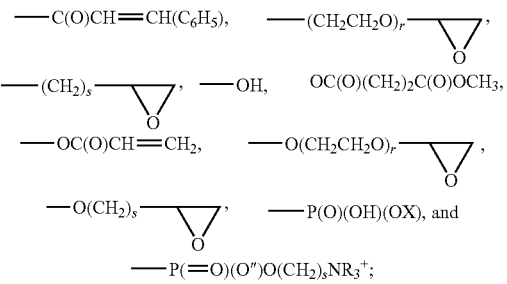

wherein R are each independently selected from hydrogen and (1C-6C)alkyl; X is selected from Cl, Br, and I; A$^-$ is an anion; r is 1-50; and s is 1-4.

As used herein, the term "synthon" refers to a molecule used to make a macrocyclic module. A synthon may be substantially one isomeric configuration, for example, a single enantiomer. A synthon may be substituted with functional groups which are used to couple a synthon to another synthon or synthons, and which are part of the synthon. A synthon may be substituted with an atom or group of atoms which are used to impart hydrophilic, lipophilic, or amphiphilic character to the synthon or to species made from the synthon. A synthon may be substituted with an atom or group of atoms to form one or more functional groups on the synthon which may be used to couple the synthon to another synthon or synthons. The synthon before being substituted with functional groups or groups used to impart hydrophilic, lipophilic, or amphiphilic character may be called the core synthon. As used herein, the term "synthon" refers to a core synthon, and also refers to a synthon substituted with functional groups or groups used to impart hydrophilic, lipophilic, or amphiphilic character.

As used herein, the term "cyclic synthon" refers to a synthon having one or more ring structures. Examples of ring structures include aryl, heteroaryl, and cyclic hydrocarbon structures including bicyclic ring structures and multicyclic ring structures. Examples of core cyclic synthons include, but are not limited to, benzene, cyclohexadiene, cyclopentadiene, naphthalene, anthracene, phenylene, phenanthracene, pyrene, triphenylene, phenanthrene, pyridine, pyrimidine, pyridazine, biphenyl, bipyridyl, cyclohexane, cyclohexene, decalin, piperidine, pyrrolidine, morpholine, piperazine, pyrazolidine, quinuclidine, tetrahydropyran, dioxane, tetrahydrothiophene, tetrahydrofuiran, pyrrole, cyclopentane, cyclopentene, triptycene, adamantane, bicyclo[2.2.1]heptane, bicyclo[2.2.1]heptene, bicyclo[2.2.2]octane, bicyclo[2.2.2]octene, bicyclo[3.3.0]octane, bicyclo[3.3.0]octene, bicyclo[3.3.1]nonane, bicyclo[3.3.1]nonene, bicyclo[3.2.2]nonane, bicyclo[3.2.2]nonene, bicyclo[4.2.2]decane, 7-azabicyclo[2.2.1]heptane, 1,3-diazabicyclo[2.2.1]heptane, and spiro[4.4]nonane. A core synthon comprises all isomers or arrangements of coupling the core synthon to other synthons. For example, the core synthon benzene includes synthons such as 1,2- and 1,3-substituted benzenes, where the linkages between synthons are formed at the 1,2- and 1,3-positions of the benzene ring, respectively. For example, the core synthon benzene includes 1,3-substituted synthons such as

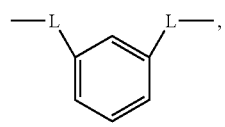

where L is a linkage between synthons and the 2,4,5,6 positions of the benzene ring may also have substituents. A condensed linkage between synthons involves a direct coupling between a ring atom of one cyclic synthon to a ring atom of another cyclic synthon, for example, where synthons M-X and M-X couple to form M-M, where M is a cyclic synthon and X is halogen; as for example when M is phenyl resulting in the condensed linkage

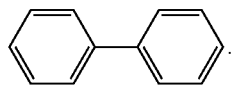

As used herein, the term "activated acid" refers to a —C(O)R moiety in which the R group is readily displaced by a nucleophile to form a covalent bond between the —C(O)— and the nucleophile. Examples of activated acids include acid chlorides, acid fluorides, p-nitrophenyl esters, pentafluorophenyl esters, and N-hydroxysuccinimide esters.

As used herein, the term "amino acid residue" refers to the product formed when a species comprising at least one amino ($-NH_2$) and at least one carboxyl (—C(O)O—) group couples through either of its amino or carboxyl groups with an atom or functional group of a synthon. Whichever of the amino or carboxyl groups is not involved in the coupling may be blocked with a removable protective group.

Macrocyclic Modules

A macrocyclic module is a closed ring of coupled synthons. To make a macrocyclic module, synthons may be substituted with functional groups to couple the synthons to form a macrocyclic module. Synthons may also be substituted with functional groups which will remain in the structure of the macrocyclic module. Functional groups which remain in the macrocyclic module may be used to couple the macrocyclic module to other macrocyclic modules.

A macrocyclic module may contain from three to about twenty-four cyclic synthons. In the closed ring of a macrocyclic module, a first cyclic synthon may be coupled to a second cyclic synthon, the second cyclic synthon may be coupled to a third cyclic synthon, the third cyclic synthon may be coupled to a fourth cyclic synthon, if four cyclic synthons are present in the macrocyclic module, the fourth to a fifth, and so on, until an $n^{th}$ cyclic synthon may be coupled to its predecessor, and the $n^{th}$ cyclic synthon may be coupled to the first cyclic synthon to form a closed ring of cyclic synthons. In one variation, the closed ring of the macrocyclic module may be formed with a linker molecule.

A macrocyclic module may be an amphiphilic macrocyclic module when hydrophilic and lipophilic functional groups exist in the structure. The amphiphilic character of a macrocyclic module may arise from atoms in the synthons, in the linkages between synthons, or in functional groups coupled to the synthons or linkages.

In some variations, one or more of the synthons of a macrocyclic module may be substituted with one or more lipophilic moieties, while one or more of the synthons may be substituted with one or more hydrophilic moieties, thereby forming an amphiphilic macrocyclic module. Lipophilic and hydrophilic moieties may be coupled to the same synthon or linkage in an amphiphilic macrocyclic module. Lipophilic and hydrophilic moieties may be coupled to the macrocyclic module before or after formation of the closed ring of the macrocyclic module. For example, lipophilic or hydrophilic moieties may be added to the macrocyclic module after formation of the closed ring by substitution of a synthon or linkage.

The amphiphilicity of a macrocyclic module may be characterized in part by its ability to form a stable Langmuir film. A Langmuir film may be formed on a Langmuir trough at a particular surface pressure measured in milliNewtons per meter (mN/m) with a particular barrier speed measured in millimeters per minute (mm/min), and the isobaric creep or change in film area at constant surface pressure can be measured to characterize stability of the film. For example, a stable Langmuir film of macrocyclic modules on a water subphase may have an isobaric creep at 5-15 mN/m such that the majority of the film area is retained over a period of time of about one hour. Examples of stable Langmuir films of macrocyclic modules on a water subphase may have isobaric creep at 5-15 mN/m such that about 70% of the film area is retained over a period of time of about 30 minutes, sometimes about 70% of the film area is retained over a period of time of about 40 minutes, sometimes about 70% of the film area is retained over a period of time of about 60 minutes, and sometimes about 70% of the film area is retained over a period of time of about 120 minutes. Other examples of stable Langmuir films of macrocyclic modules on a water subphase may have isobaric creep at 5-15 mN/m such that about 80% of the film area is retained over a period of time of about thirty minutes, sometimes about 85% of the film area is retained over a period of time of about thirty minutes, sometimes about 90% of the film area is retained over a period of time of about thirty minutes, sometimes about 95% of the film area is retained over a period of time of about thirty minutes, and sometimes about 98% of the film area is retained over a period of time of about thirty minutes.

In one aspect, an individual macrocyclic module may include a pore in its structure. Each macrocyclic module may define a pore of a particular size, depending on the conformation and state of the module. Various macrocyclic modules may be prepared which define pores of different sizes.

A macrocyclic module may include a flexibility in its structure. Flexibility may permit a macrocyclic module to more easily form linkages with other macrocyclic modules by coupling reactions. Flexibility of a macrocyclic module may also play a role in regulating passage of species through the pore of the macrocyclic module. For example, flexibility may affect the dimension of the pore of a macrocyclic module since various conformations may be available to the structure. For example, a macrocyclic module may have a certain pore dimension in one conformation when no substituents are located at the pore, and have a different pore dimension in another conformation when one or more substituents are located at the pore. Likewise, a macrocyclic module may have a certain pore dimension in one conformation when one group of substituents are located at the pore, and have a different pore dimension in a different conformation when a different group of substituents are located at the pore. For example, the "one group" of substituents located at the pore may be three alkoxy groups arranged in one regioisomer, while the "different group" of substituents may be two alkoxy groups arranged in another regioisomer. The effect of the "one group" of substituents located at the pore and the "different group" of substituents located at the pore is to provide a macrocyclic module composition which may regulate transport and filtration, in conjunction with other regulating factors.

In making macrocyclic modules from synthons, the synthons may be used as a substantially pure single isomer, for example, as a pure single enantiomer.

In making macrocyclic modules from synthons, one or more coupling linkages are formed between adjacent synthons. The linkage formed between synthons may be the product of the coupling of one functional group on one synthon to a complementary functional group on a second synthon. For example, a hydroxyl group of a first synthon may couple with an acid group or acid halide group of a second synthon to form an ester linkage between the two synthons. Another example is an imine linkage, —CH=N—, resulting from the reaction of an aldehyde, —CH=O, on one synthon with an amine, —NH$_2$, on another synthon. Examples of complementary functional groups and linkages between synthons are shown in Table 1.

TABLE 1

Examples of functional groups of synthons and synthon linkages

| Functional Group A | Functional Group B | Linkage Formed |
|---|---|---|
| —NH$_2$ | —C(O)H | —N=CH— |
| —NH$_2$ | —CO$_2$H | —NHC(O)— |
| —NHR | —CO$_2$H | —NRC(O)— |
| —OH | —CO$_2$H | —OC(O)— |
| —X | —ONa | —O— |
| —SH | —SH | —S—S— |
| —X | —(NR)Li | —NR— |
| —X | —SNa | —S— |
| —X | —NHR | —NR— |
| —X | —CH$_2$CuLi | —CH$_2$— |
| —X | —(CRR')$_{n=1-6}$CuLi | —(CRR')$_n$— |
| synthon-X | synthon-X | synthon-synthon |
| —CH$_2$X | —CH$_2$X | —CH$_2$CH$_2$— |
| —ONa | —C(O)OR | —C(O)O— |
| —SNa | —C(O)OR | —C(O)S— |
| —X | —C≡CH | —C≡C— |
| —C≡CH | —C≡CH | —C≡C—C≡C— |
| —MgX | —C(O)H | —CH(OH)— |
| synthon-NH$_2$ | synthon—epoxide | synthon—CH(OH)—CH$_2$—NH-synthon |
| synthon-MgX | synthon—epoxide | synthon—CH(OH)—CH$_2$-synthon |
| (isopropenyl)synthon | synthon-X | synthon—C(CH$_3$)$_2$—CH$_2$-synthon |
| —C(O)H | —C(O)H | —HC=CH— |
| (CH$_3$)$_2$C=CH-synthon | synthon-C(O)Cl | (CH$_3$)$_2$C=CH—C(O)-synthon |
| —N=C=O | —NH$_2$ | —NHC(O)NH— |
| —N=C=O | HO— | —NHC(O)O— |
| —C(O)H | —NHNH$_2$ | —CH=N—NH— |
| —OH | —OC(O)X | —OC(O)O— |
| (CH$_3$)$_2$C=CH-synthon | synthon-SH | (CH$_3$)$_2$C(S-synthon)—CH$_2$-synthon |

TABLE 1-continued

Examples of functional groups of synthons and synthon linkages

| Functional Group A | Functional Group B | Linkage Formed |
|---|---|---|
| $(CH_3)_2CHC(O)O$-synthon | synthon-$CH(O)$ | synthon–C(CH$_3$)$_2$–C(=O)–O–synthon with OH substituent |
| synthon-$CH_2C(O)OH$ | synthon-$CH_2C(O)OH$ | synthon–CH$_2$–C(=O)–CH(C(=O)OH)–synthon |
| synthon–CH=CH$_2$ | $R_2$SiH-synthon | synthon–CH$_2$–CH$_2$–SiR$_2$–synthon |
| synthon–CH=CH$_2$ | synthon–CH=CH$_2$ | synthon–(cyclobutane)–synthon |
| CH$_2$=C(R)–(Synthon A) | CH$_2$=C(R)–(Synthon B) | cyclobutane with R, R at two carbons and Synthon A, Synthon B at the other two |
| Ph–CH=CH–(Synthon A) | Ph–CH=CH–(Synthon B) | cyclobutane with Ph, Ph and Synthon A, Synthon B substituents |
| —OP(O)(OH)$_2$ | —OH | —OP(O)(OH)O— |

In Table 1, R and R' represent hydrogen or organic groups, and X is halogen or other good leaving groups.

In another variation, a macrocyclic module may have functional groups for coupling to other macrocyclic modules which were coupled to the macrocyclic module after initial preparation of the closed ring. For example, an imine linkage of a macrocyclic module may be substituted with one of various functional groups to produce additional macrocyclic modules. Examples of linkages between synthons having functional groups for coupling macrocyclic modules are shown in Table 2.

TABLE 2

Examples of functional groups of synthons and synthon linkages

| Functional Group of Macrocyclic Module Linkage | Reagent | Substituted Linkage |
|---|---|---|
| $Q_1$–NH–$Q_2$ | Cl–C(=O)–CH=CH$_2$ | $Q_1$–N(C(=O)CH=CH$_2$)–$Q_2$ |
| $Q_1$–CH$_2$–NH–$Q_2$ | Cl–C(=O)–CH=CH$_2$ | $Q_1$–CH$_2$–N(C(=O)CH=CH$_2$)–$Q_2$ |
| $Q_1$–CH(OH)–$Q_2$ | Cl–C(=O)–CH=CH$_2$ | $Q_1$–CH(O–C(=O)CH=CH$_2$)–$Q_2$ |

TABLE 2-continued

Examples of functional groups of synthons and synthon linkages

| Functional Group of Macrocyclic Module Linkage | Reagent | Substituted Linkage |
|---|---|---|
| $Q_1$—CH(X)—$Q_2$ | X—≡—H | $Q_1$—CH(C≡CH)—$Q_2$ |
| $Q_1$—CH(X)—$Q_2$ | X—C$_6$H$_4$—CH=CH$_2$ | $Q_1$—CH(C$_6$H$_4$CH=CH$_2$)—$Q_2$ |
| $Q_1$—NH—$Q_2$ | CH$_2$=C(R)C(O)Cl, R = alkyl | $Q_1$—N(C(O)C(R)=CH$_2$)—$Q_2$ |
| $Q_1$—CH(OH)—$Q_2$ | CH$_2$=C(R)C(O)Cl, R = alkyl | $Q_1$—CH(OC(O)C(R)=CH$_2$)—$Q_2$ |
| $Q_1$—NH—$Q_2$ | PhCH=CHC(O)Cl | $Q_1$—N(C(O)CH=CHPh)—$Q_2$ |
| $Q_1$—CH(OH)—$Q_2$ | PhCH=CHC(O)Cl | $Q_1$—CH(OC(O)CH=CHPh)—$Q_2$ |

In Table 2, X is halogen.

The functional groups of synthons used to form linkages between synthons may be separated from the synthon by a spacer. A spacer can be any atom or group of atoms which couples the functional group to the synthon, and does not interfere with the linkage-forming reaction. A spacer is part of the functional group, and becomes part of the linkage between synthons. An example of a spacer is a methylene group, —CH$_2$—. The spacer may be said to extend the linkage between synthons. For example, if one methylene spacer were inserted in an imine linkage, —CH=N—, the resulting imine linkage may be —CH$_2$CH=N—.

A linkage between synthons may also contain one or more atoms provided by an external moiety other than the two functional groups of the synthons. An external moiety may be a linker molecule which may couple with the functional group of one synthon to form an intermediate which couples with a functional group on another synthon to form a linkage between the synthons, such as, for example, to form a closed ring of synthons from a series of coupled synthons. An example of a linker molecule is formaldehyde. For example, amino groups on two synthons may undergo Mannich reaction in the presence of formaldehyde as the linker molecule to produce the linkage —NHCH$_2$NH—.

In one variation, a macrocyclic module may be a closed ring composition of the formula:

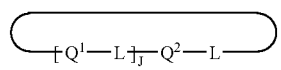

wherein:

The closed ring comprises a total of from three to twenty-four synthons Q; J is 2-23;

$Q^1$ are synthons each independently selected from the group consisting of (a) aryl synthons, (b) heteroaryl synthons, (c) saturated cyclic hydrocarbon synthons, (d) unsaturated cyclic hydrocarbon synthons, (e) saturated bicyclic hydrocarbon synthons, (f) unsaturated bicyclic hydrocarbon synthons, (g) saturated multicyclic hydrocarbon synthons, and (h) unsaturated multicyclic hydrocarbon synthons; wherein ring positions of each $Q^1$ which are not coupled to a linkage L are substituted with hydrogen or organic functional groups containing atoms selected from the group of C, H, N, O, Si, P, S, B, Al, halogens, and metals from the alkali and alkaline earth groups;

$Q^2$ is a synthon independently selected from the group consisting of (a) aryl synthons, (b) heteroaryl synthons, (c) saturated cyclic hydrocarbon synthons, (d) unsaturated cyclic hydrocarbon synthons, (e) saturated bicyclic hydrocarbon synthons, (f) unsaturated bicyclic hydrocarbon synthons, (g) saturated multicyclic hydrocarbon synthons, and (h) unsaturated multicyclic hydrocarbon synthons; wherein ring positions of $Q^2$ which are not coupled to an L are substituted with hydrogen or organic functional groups containing atoms selected from the group consisting of C, H, N, O, Si, P, S, B, Al, halogens, and metals from the alkali and alkaline earth groups;

L are linkages between the synthons each independently selected from the group consisting of synthon-synthon, —NRC(O)—, —OC(O)—, —O—, —S—S—, —S—, —NR—, —(CRR')$_p$—, —CH$_2$NH—, —C(O)S—, —C(O)O—, —C≡C—, —C≡C—C≡C—, —CH(OH)—, —HC=CH—, —NHC(O)NH—, —NHC(O)O—, —NHCH$_2$NH—, —NHCH$_2$CH(OH)CH$_2$NH—, —N=CH(CH$_2$)$_p$CH=N—, —CH$_2$CH(OH)CH$_2$—, —N=CH(CH$_2$)$_h$CH=N— where h is 1-4, —CH=N—NH—, —OC(O)O—, —OP(O)(OH)O—, —CH(OH)CH$_2$NH—, —CH(OH)CH$_2$—, —CH(OH)C(CH$_3$)$_2$C(O)O—,

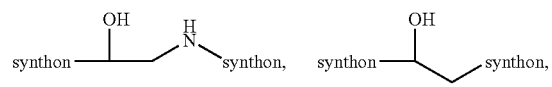

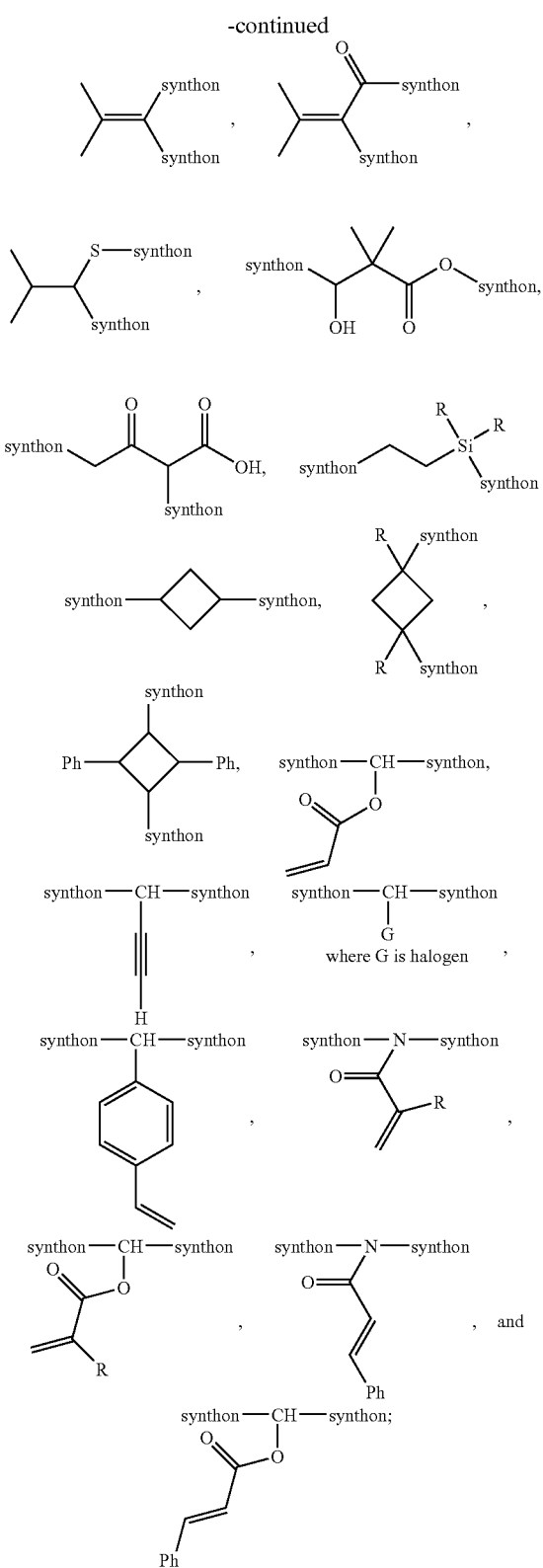

wherein p is 1-6;

wherein R and R' are each independently selected from the group of hydrogen and alkyl; wherein the linkages L are each independently configured with respect to the $Q^1$ and $Q^2$ syn-thons, each L having either of its two possible configurations with respect to the synthons it couples together, the forward and reverse configurations of the linkage with respect to the immediately adjacent synthons to which it couples, for example, $Q^1_a$—NHC(O)-$Q^1_b$ and $Q^1_a$—C(O)NH— $Q^1_b$, if the two configurations are isomerically different structures. Synthons $Q^1$, when independently selected, may be any cyclic synthon as described, so that the J synthons $Q^1$ may be found in the closed ring in any order, for example, cyclohexyl-1,2-phenyl-piperidinyl-1,2-phenyl-1,2-phenyl-cyclohexyl, and so on, and the J linkages L may also be independently selected and configured in the closed ring. The macrocyclic modules represented and encompassed by the formula include all stereoisomers of the synthons involved, so that a wide variety of stereoisomers of the macrocyclic module are included for each closed ring composition of synthons.

A macrocyclic module may include functional groups for coupling the macrocyclic module to a solid surface, substrate, or support. Examples of functional groups of macrocyclic modules which can be used to couple to a substrate or surface include amine, carboxylic acid, carboxylic ester, benzophenone and other light activated crosslinkers, alcohol, glycol, vinyl, styryl, olefin styryl, epoxide, thiol, magnesium halo or Grignard, acrylate, acrylamide, diene, aldehyde, and mixtures thereof. These functional groups may be coupled to the closed ring of the macrocyclic module, and may optionally be attached by a spacer group. Examples of solid surfaces include metal surfaces, ceramic surfaces, polymer surfaces, semiconductor surfaces, silicon wafer surfaces, alumina surfaces, and so on. Examples of functional groups of macrocyclic modules which can be used to couple to a substrate or surface further include those described in the left hand column of Tables 1 and 2. Methods of initiating coupling of the modules to the substrate include chemical, thermal, photochemical, electrochemical, and irradiative methods.

Examples of spacer groups include polyethylene oxides, polypropylene oxides, polysaccharides, polylysines, polypeptides, poly(amino acids), polyvinylpyrrolidones, polyesters, polyvinylchlorides, polyvinylidene fluorides, polyvinylalcohols, polyurethanes, polyamides, polyimides, polysulfones, polyethersulfones, polysulfonamides, and polysulfoxides.

A substrate may have functional groups which couple to the macrocyclic modules. The functional groups of the substrate may be surface groups or linking groups bound to the substrate, which may be formed by reactions which bind the surface groups or linking groups to the substrate. Surface groups may also be created on the substrate by a variety of treatments such as cold plasma treatment, surface etching methods, solid abrasion methods, or chemical treatments. Some methods of plasma treatment are given in Inagaki, *Plasma Surface Modification and Plasma Polymerization*, Technomic, Lancaster, Pa., 1996. The functional groups of the macrocyclic modules and the surface may be blocked with protecting groups until needed. In one variation, a photoreactive group such as a benzophenone group is bound to the surface or substrate. The photoreactive group may be activated with light, for example, ultraviolet light to provide a reactive species which couples to a macrocyclic module.

Examples of modules useful as building blocks are shown in Table 3.
TABLE 3
Examples of macrocyclic modules
| Macrocyclic Module | Structure |
|---|---|
| Hexamer 1a | 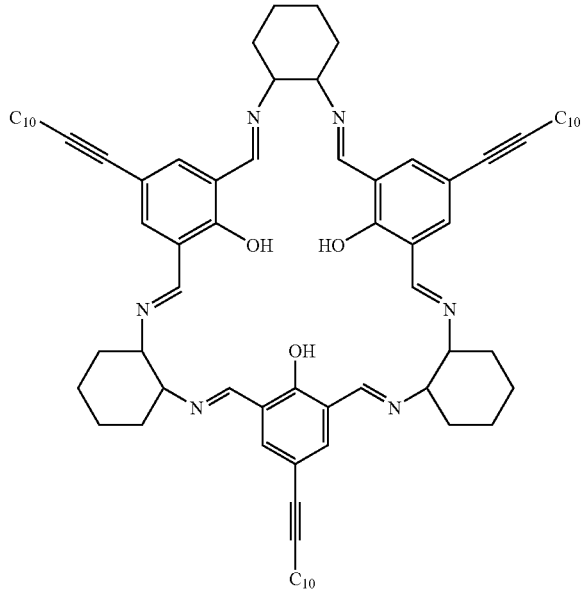 |
| Hexamer 1dh | 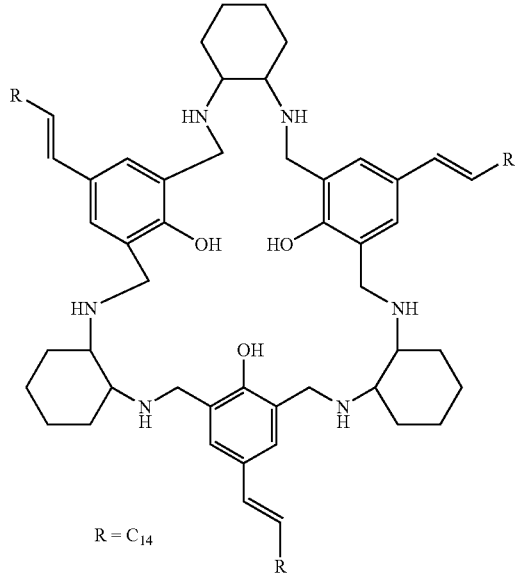  R = C$_{14}$ |

TABLE 3-continued
Examples of macrocyclic modules
| Macrocyclic Module | Structure |
|---|---|
| Hexamer 3j-amine | 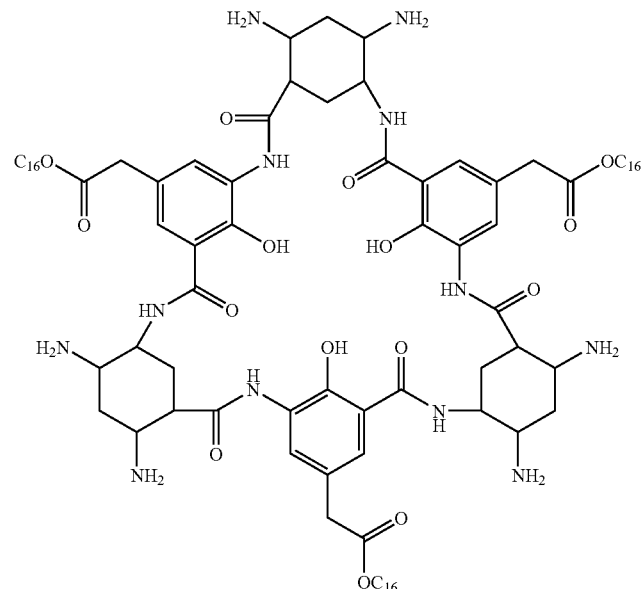 |
| Hexamer 1jh | 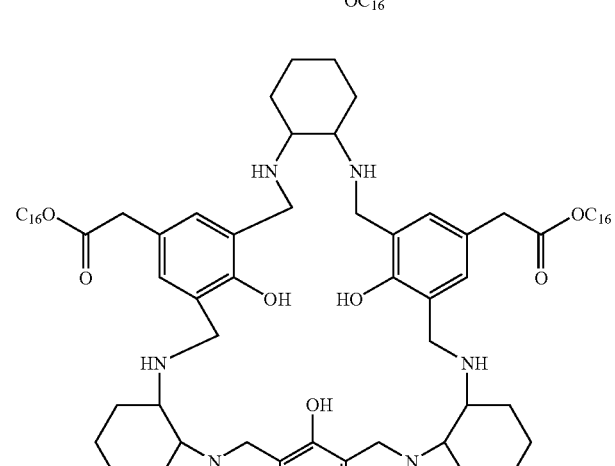 |

TABLE 3-continued

Examples of macrocyclic modules

| Macrocyclic Module | Structure |
|---|---|
| Hexamer 2j-amine/ester | (structure) |
| Hexamer 1dh-acryl | (structure); R = H or acryl, and mixtures there of |

TABLE 3-continued

Examples of macrocyclic modules

| Macrocyclic Module | Structure |
|---|---|
| Octamer 5jh-aspartic | 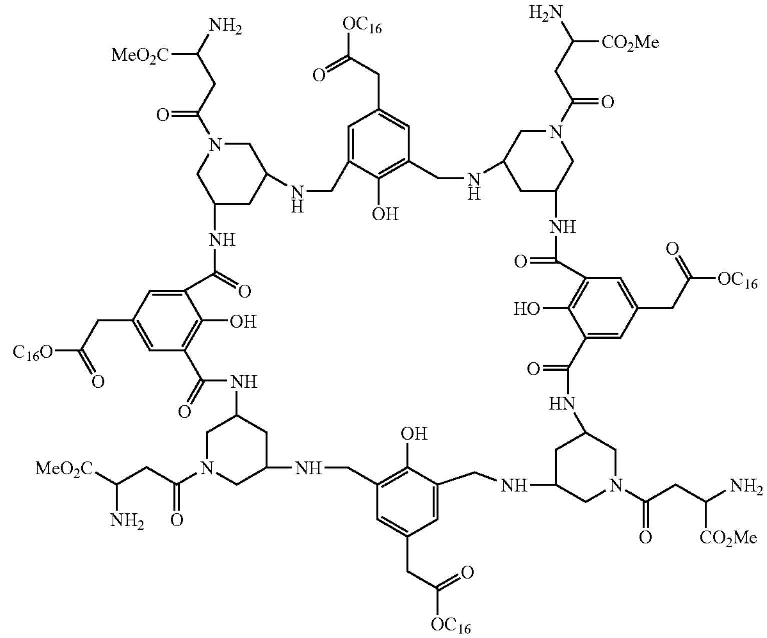 |
| Octamer 4jh-acryl | R = H or (acryloyl group) and mixtures there of |

Macrocyclic Module Pores

An individual macrocyclic module may include a pore in its structure. The size of the pore may determine the size of molecules or other species which can pass through the macrocyclic module. The size of a pore in a macrocyclic module may depend on the structure of the synthons used to make the macrocyclic module, the linkages between synthons, the number of synthons in a module, the structure of any linker molecules used to make the macrocyclic module, and other structural features of the macrocyclic module whether inherent in the preparation of the macrocyclic module or added in later steps or modifications. Stereoisomerism of macrocyclic modules may also be used to regulate the size of a pore of a macrocyclic module by variation of the stereoisomer of each synthon used to prepare the closed ring of the macrocyclic module.

The dimension of a pore in a macrocyclic module may be varied by changing the combination of synthons used to form the macrocyclic module, or by varying the number of synthons in the closed ring. The dimension of a pore may also be varied by substituents on the synthons or linkages. The pore may therefore be made large enough or small enough to achieve an effect on transport of species through the pore. Species which may be transported through the pore of a macrocyclic module include atoms, molecules, biomolecules, ions, charged particles, and photons.

The size of a species may not be the sole determinant of whether it will be able to pass through a pore of a macrocyclic module. Groups or moieties located in or near the pore structure of a macrocyclic module may regulate or affect transport of a species through the pore by various mechanisms. For example, transport of a species through the pore may be affected by groups of the macrocyclic module which interact with the species, by ionic or other interaction, such as chelating groups, or by complexing the species. For example, a charged group such as a carboxylate anion or ammonium group may couple an oppositely-charged species and affect its transport. Substituents of synthons in a macrocyclic module may affect the passage of a species through the pore of the macrocyclic module. Groups of atoms which render the pore of a macrocyclic module more or less hydrophilic or lipophilic may affect transport of a species through the pore. An atom or group of atoms may be located within or proximate to a pore to sterically slow or block the passage of a species through the pore. For example, hydroxyl or alkoxy groups may be coupled to a cyclic synthon and located in the pore of the structure of the macrocyclic module, or may be coupled to a linkage between synthons and located in the pore. A wide range of functional groups may be used to sterically slow or block the passage of a species through the pore, including organic functional groups containing atoms selected from the group consisting of C, H, N, O, Si, P, S, B, Al, halogens, and metals from the alkali and alkaline earth groups. Blocking and slowing passage of a species through the pore may involve reducing the dimension of the pore by steric blocking, as well as slowing the passage of species by creating a path through the pore which is not linear, and providing interaction between the functional group and the species to slow transport. The stereochemical structure of the portion of the macrocyclic module which defines the pore and its interior may also affect transport. Any groups or moieties which affect transport of a species through the pore of a macrocyclic module may be introduced as part of the synthons used to prepare the macrocyclic module, or may be added later by various means. For example, S7-1 could be reacted with $ClC(O)(CH_2)_2C(O)OCH_2CH_3$ to convert the phenol groups to succinyl ester groups. Further, molecular dynamical motion of the synthons and linkages of a partly flexible macrocyclic module may affect transport of a species through the pore of the module. Transport behavior may not be described solely by the structure of the macrocyclic module itself since the presence of the species which is to be transported through the pore affects the flexibility, conformation, and dynamical motions of a macrocyclic module. In general, solvent may also affect transport of solutes through a pore.

Macrocyclic modules and arrays of macrocyclic modules may be useful in size exclusion separations, ion separation, gas separation, separation of enantiomers, small molecule separation, water purification, filtration of bacteria, fungi, or viruses, sewage treatment, and toxin removal, among other uses.

EXAMPLES

The following examples further describe and demonstrate variations within the scope of the present invention. All examples described in this specification, both in the description above and the examples below, as well as in the figures, are given solely for the purpose of illustration and are not to be construed as limiting the present invention. While there have been described illustrative variations of this invention, those skilled in the art will recognize that they may be changed or modified without departing from the spirit and scope of this invention, and it is intended to cover all such changes, modifications, and equivalent arrangements that fall within the true scope of the invention as set forth in the appended claims.

All chemical structures illustrated and described in this specification, both in the description above and the examples below, as well as in the figures, are intended to encompass and include all variations and isomers of the structure which are foreseeable, including all stereoisomers and constitutional or configurational isomers when the illustration, description, or figure is not explicitly limited to any particular isomer.

All documents referenced herein, including applications for patent, patent references, publications, articles, books, and treatises, are specifically incorporated by reference herein in their entirety.

Methods to Prepare Cyclic Synthons

To avoid the need to separate single configurational or enantiomeric isomers from complex mixtures resulting from non-specific reactions, stereospecific or at least stereoselective coupling reactions may be employed in the preparation of the synthons of this invention. The following are examples of synthetic schemes for several classes of synthons useful in the preparation of macrocyclic modules of this invention. In general, the core synthons are illustrated, and lipophilic moieties are not shown on the structures, however, it is understood that all of the following synthetic schemes might encompass additional lipophilic or hydrophilic moieties used to prepare amphiphilic and other modified macrocyclic modules. Species are numbered in relation to the scheme in which they appear; for example, "S1-1" refers to the structure 1 in Scheme 1.

An approach to preparing synthons of 1,3-Diaminocyclohex-5-ene is shown in Scheme 1. Enzymatically assisted partial hydrolysis of the

SCHEME 1

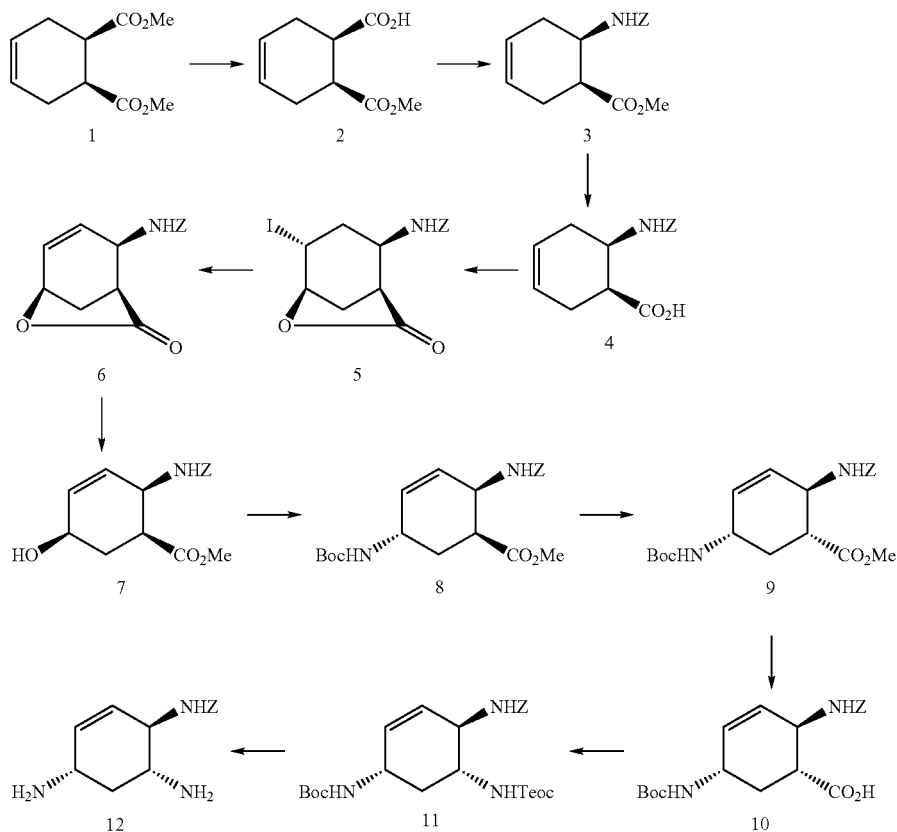

symmetrical diester S1-1 is used to give enantiomerically pure S1-2. S1-2 is subjected to the Curtius reaction and then quenched with benzyl alcohol to give protected amino acid S1-3. Iodolactonization of carboxylic acid S1-4 followed by dehydrohalogenation gives unsaturated lactone S1-6. Opening of the lactone ring with sodium methoxide gives alcohol S1-7, which is converted with inversion of configuration to S1-8 in a one-pot reaction involving mesylation, $SN_2$ displacement with azide, reduction and protection of the resulting amine with di-tert-butyl dicarbonate. Epimerization of S1-8 to the more stable diequatorial configuration followed by saponification gives carboxylic acid S1-10. S1-10 is subjected to the Curtius reaction. A mixed anhydride is prepared using ethyl chloroformate followed by reaction with aqueous $NaN_3$ to give the acyl azide, which is thermally rearranged to the isocyanate in refluxing benzene. The isocyanate is quenched with 2-trimethylsilylethanol to give differentially protected tricarbamate S1-11. Reaction with trifluoroacetic acid (TFA) selectively deprotects the 1,3-diamino groups to provide the desired synthon S1-12.

In another variation, an approach to preparing synthons of 1,3-Diaminocyclohexane is shown in Scheme 1a.

SCHEME 1a

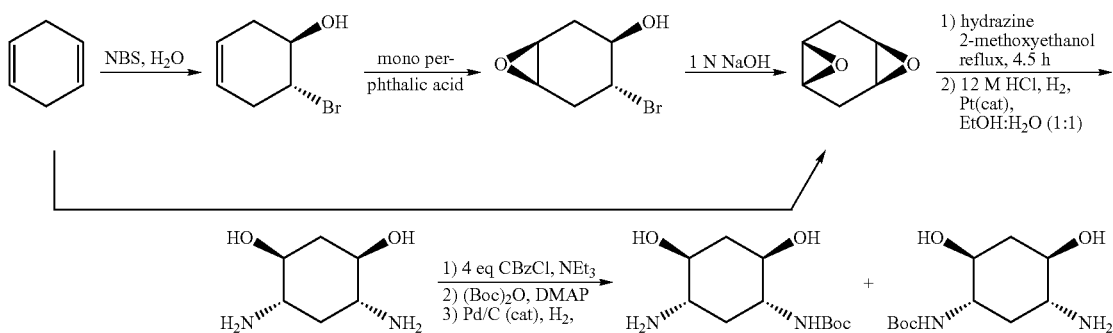

Some aspects of these preparations are given in Suami et al., *J. Org. Chem.* 1975, 40, 456 and Kavadias et al. *Can. J Chem.* 1978, 56, 404.

In another variation, an approach to preparing synthons of 1,3-substituted cyclohexane is shown in Scheme 1.

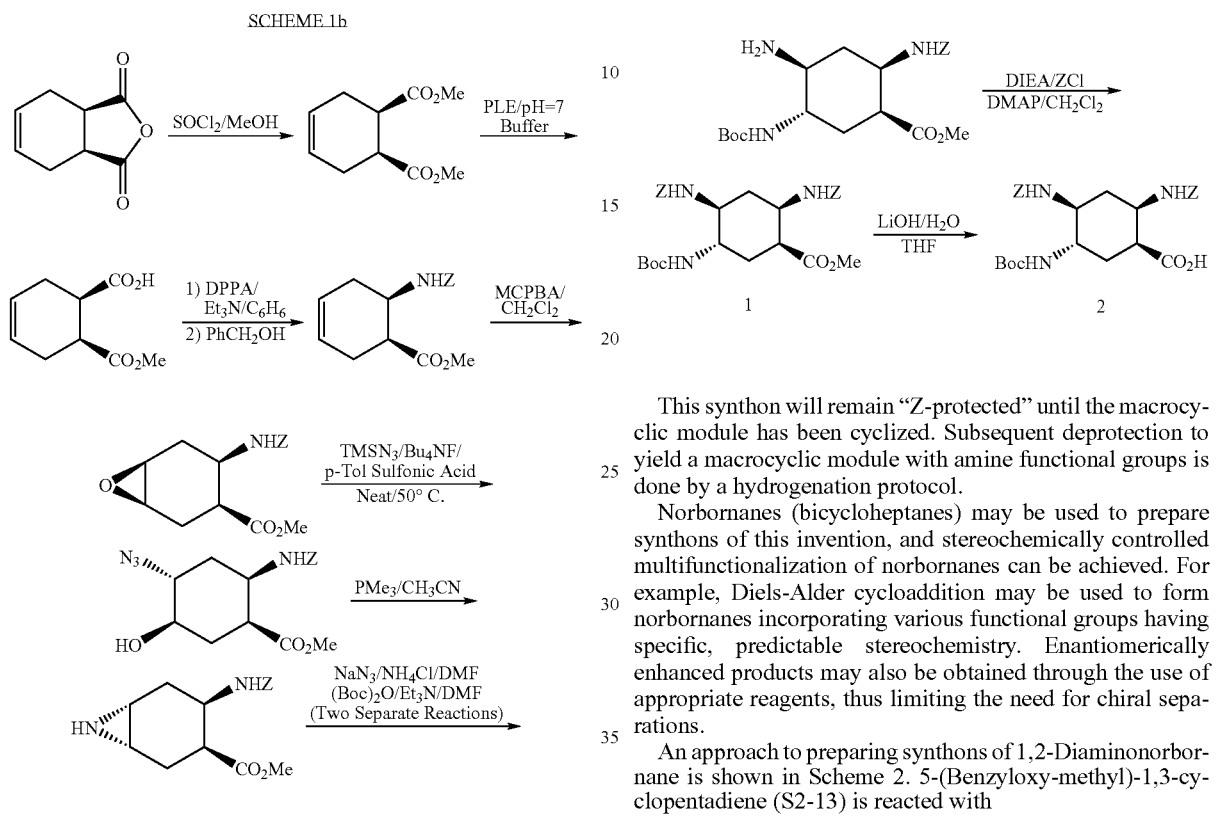

This synthon will remain "Z-protected" until the macrocyclic module has been cyclized. Subsequent deprotection to yield a macrocyclic module with amine functional groups is done by a hydrogenation protocol.

Norbornanes (bicycloheptanes) may be used to prepare synthons of this invention, and stereochemically controlled multifunctionalization of norbornanes can be achieved. For example, Diels-Alder cycloaddition may be used to form norbornanes incorporating various functional groups having specific, predictable stereochemistry. Enantiomerically enhanced products may also be obtained through the use of appropriate reagents, thus limiting the need for chiral separations.

An approach to preparing synthons of 1,2-Diaminonorbornane is shown in Scheme 2. 5-(Benzyloxy-methyl)-1,3-cyclopentadiene (S2-13) is reacted with

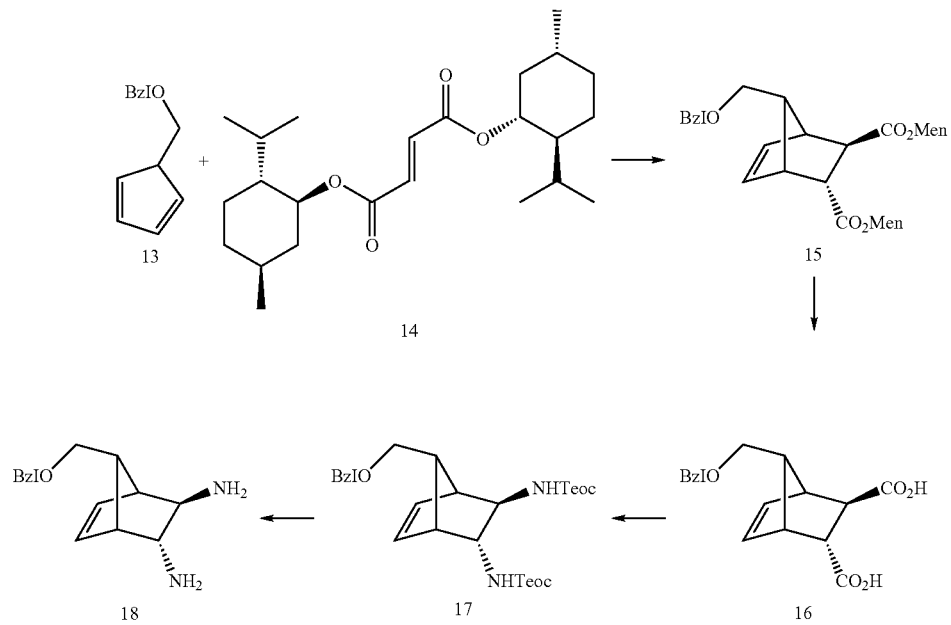

diethylaluminum chloride Lewis acid complex of di-(l)-menthyl fumarate (S2-14) at low temperature to give the diastereomerically pure norbornene S2-15. Saponification with potassium hydroxide in aqueous ethanol gives the diacid S2-16, which is subjected to a tandem Curtius reaction with diphenylphosphoryl azide (DPPA), the reaction product is quenched with 2-trimethylsilylethanol to give the biscarbamate S2-17. Deprotection with TFA gives diamine S2-18.

Another approach to this synthon class is outlined in Scheme 3. Opening of anhydride S3-19 with methanol in the presence of quinidine gives the enantiomerically pure ester acid S3-20. Epimerization of the ester group with sodium methoxide (NaOMe) gives S3-21. A Curtius reaction with DPPA followed by quenching with trimethylsilylethanol gives carbamate S3-22. Saponification with NaOH gives the acid S3-23, which undergoes a Curtius reaction,

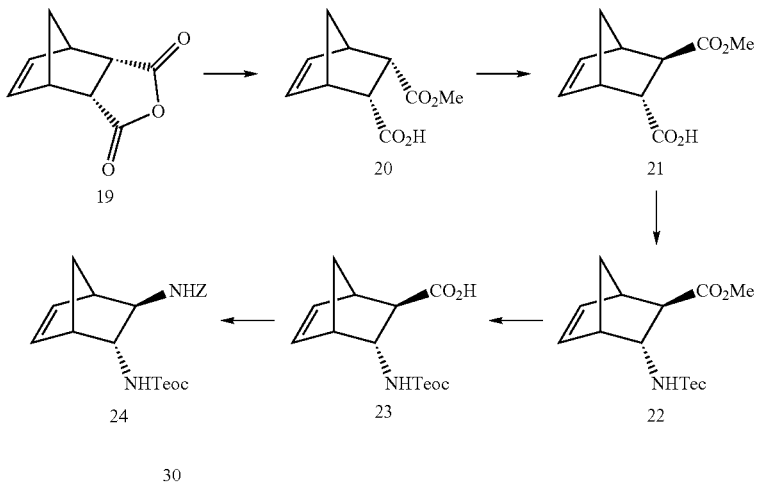

SCHEME 3 then quenched with benzyl alcohol to give differentially protected biscarbamate S3-24. Compound S3-24 can be fully deprotected to provide the diamine or either of the carbamates can be selectively deprotected.

An approach to preparing synthons of endo,endo-1,3-Diaminonorbomane is shown in Scheme 4. 5-Trimethylsilyl-1,3-cyclopentadiene (S4-25) is reacted with the diethylaluminum chloride Lewis acid complex of di-(l)-menthyl fumarate at low temperature to give nearly diastereomerically pure norbornene S4-26. Crystallization of S4-26 from alcohol results in recovery of greater than 99% of the single diastereomer. Bromolactonization followed by silver mediated rearrangement gives mixed diester S4-28 with an alcohol moiety at the 7-position. Protection of the alcohol with benzyl bromide and selective deprotection of the methyl ester gives the free carboxylic acid S4-30. A Curtius reaction results in trimethylsilylethyl carbamate norbornene S4-31. Biscarbonylation of the olefin in methanol, followed by a single-step deprotection and dehydration gives the mono-anhydride S4-33. Quinidine mediated opening of the anhydride with methanol gives S4-34. Curtius transformation of S4-34 gives the biscarbamate S4-35, which is deprotected with TFA or tetrabutylammonium fluoride (TBAF) to give diamine S4-36.

SCHEME 4

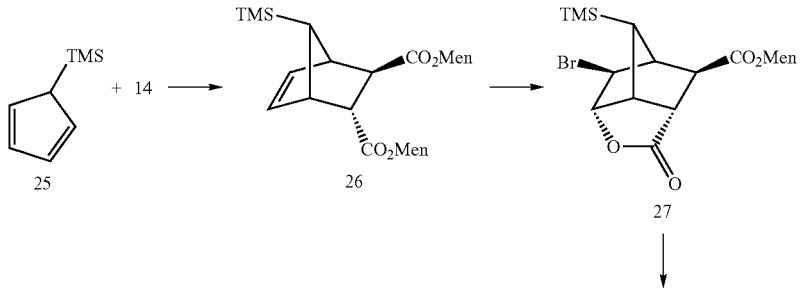

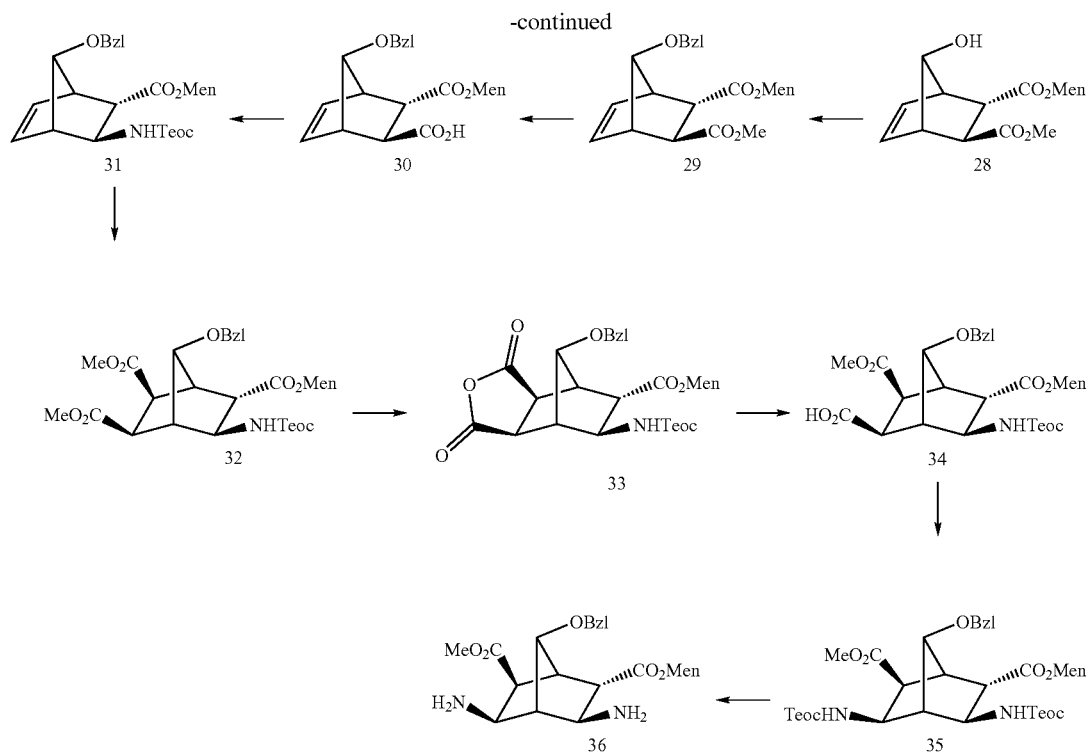

Another approach to this class of synthons is outlined in Scheme 5. Benzyl alcohol opening of S3-19 in the presence of quinidine gives S5-37 in high enantiomeric excess. Iodolactonization followed by NaBH$_4$ reduction gives lactone S5-39. Treatment with NaOMe liberates the methyl ester and the free alcohol to generate S5-40. Transformation of the alcohol S5-40 to the inverted t-butyl carbamate protected amine S5-41 is accomplished in a one-pot reaction by azide deplacement of the mesylate S5-40 followed by reduction to the amine, which is protected with di-tert-butyl dicarbonate. Hydrogenolytic cleavage of the benzyl ester and epimerization of the methyl ester to the exo configuration is followed by protection of the free acid with benzyl bromide to give S5-44. Saponification of the methyl ester followed by a trimethylsilylethanol quenched Curtius reaction

SCHEME 5

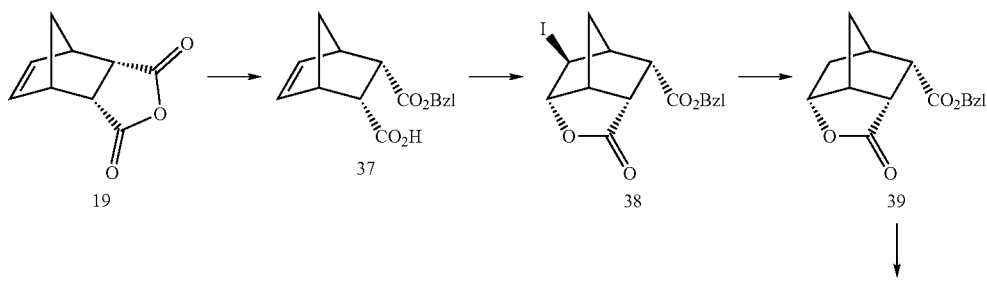

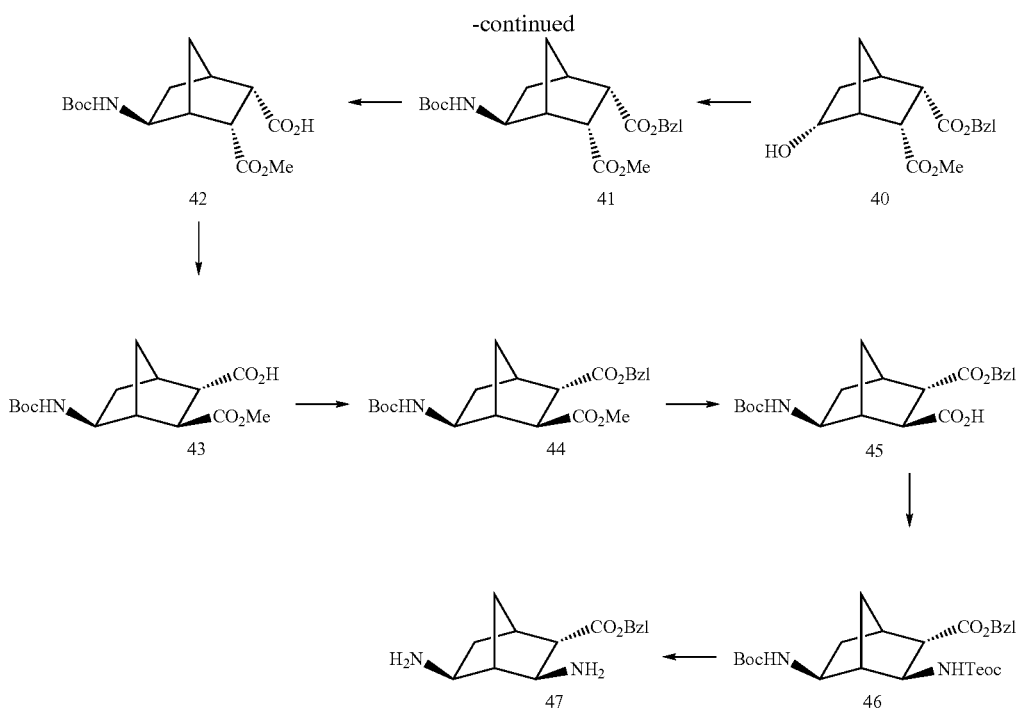

gives the biscarbamate S5-46, which is cleaved with TFA to give the desired diamine S5-47.

An approach to preparing synthons of exo;endo-1,3-Diaminonorbomane is shown in Scheme 6. p-Methoxybenzyl alcohol opening of norbornene anhydride S3-19 in the presence of quinidine gives monoester S6-48 in high enantiomeric excess. Curtius reaction of the free acid gives protected all endo monoacid-monoamine S6-49. Biscarbonylation and anhydride formation gives exo-monoanhydride S6-51. Selective methanolysis in the presence of quinine gives S6-52. A trimethylsilylethanol quenched Curtius reaction gives biscarbamate S6-53. Epimerization of the two esters results in the more sterically stable S6-54. Cleavage of the carbamate groups provides synthon S6-55.

SCHEME 6

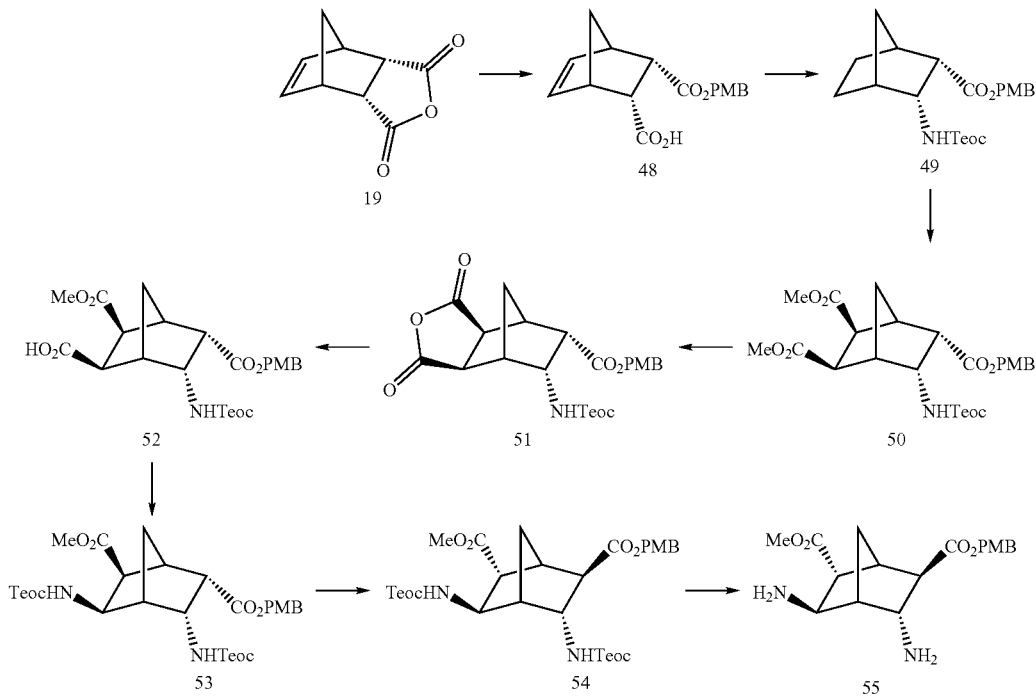

Methods to Prepare Macrocyclic Modules

Synthons may be coupled to one another to form macrocyclic modules. In one variation, the coupling of synthons may be accomplished in a concerted scheme. Preparation of a macrocyclic module by the concerted route requires at least two types of synthons, each type having at least two functional groups for coupling to other synthons. The functional groups may be selected so that a functional group of one type of synthon can couple only to a functional group of the other type of synthon. When two types of synthons are used, a macrocyclic module may be formed having alternating synthons of different types. Scheme 7 illustrates a concerted module synthesis.

Referring to Scheme 7, 1,2-Diaminocyclohexane, S7-1, is a synthon having two amino functional groups for coupling to other synthons, and 2,6-diformyl-4-dodec-1-ynylphenol, S7-2, is a synthon having two formyl groups for coupling to other synthons. An amino group may couple with a formyl group to form an imine linkage. In Scheme 7, a concerted product hexamer macrocyclic module is shown.

In one variation, a mixture of tetramer, hexamer, and octamer macrocyclic modules may be formed in the concerted scheme. The yields of these macrocyclic modules can be varied by changing the concentration of various synthons in the reagent mixture, and among other factors, by changing the solvent, temperature, and reaction time.

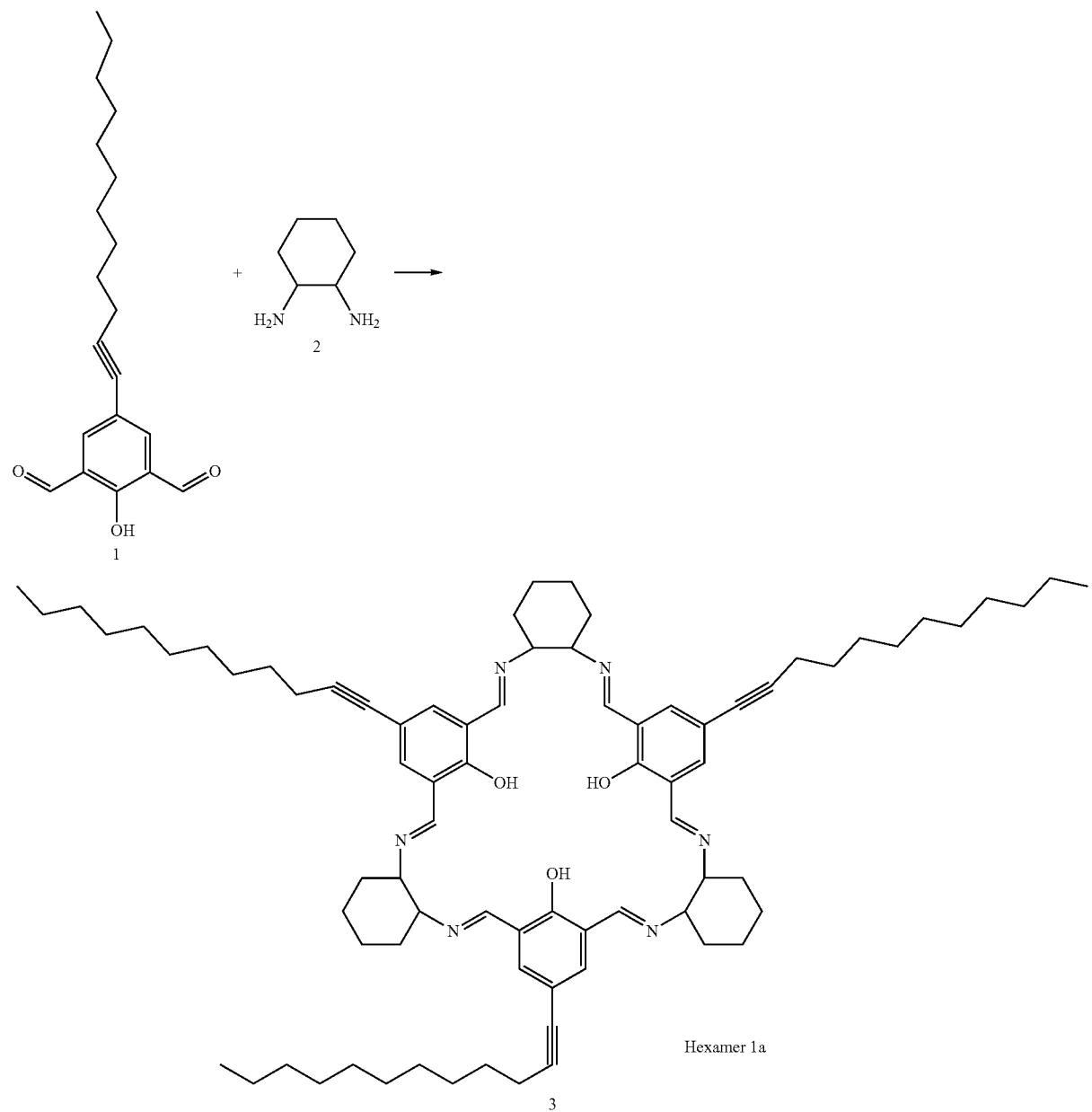

SCHEME 7

Hexamer 1a

The imine groups of S7-3 can be reduced, e.g. with sodium borohydride, to give amine linkages. If the reaction is carried out using 2,6-di(chlorocarbonyl)-4-dodec-1-ynylphenol instead of 2,6-diformyl-4-dodec-1-ynylphenol, the resulting module will contain amide linkages. Similarly, if 1,2-dihydroxycyclohexane is reacted with 2,6-di(chlorocarbonyl)-4-dodec-1-ynylphenol, the resulting module will contain ester linkages.

In some variations, the coupling of synthons may be accomplished in a stepwise scheme. In the stepwise preparation of macrocyclic modules, a first type of synthon is substituted with one protected functional group and one unprotected functional group. A second type of synthon is substituted with an unprotected functional group that will couple with the unprotected functional group on the first synthon. The product of contacting the first type of synthon with the second type of synthon may be a dimer, which is made of two coupled synthons. The second synthon may also be substituted with another functional group which is either protected, or which does not couple with the first synthon when the dimer is formed. The dimer may be isolated and purified, or the preparation may proceed as a one-pot method. The dimer may be contacted with a third synthon having two functional groups, only one of which may couple with the remaining functional group of either the first or second synthons to form a trimer, which is made of three coupled synthons. Such stepwise coupling of synthons may be repeated to form macrocyclic modules of various ring sizes. To cyclize or close the ring of the macrocyclic module, the $n^{th}$ synthon which was coupled to the product may be substituted with a second functional group which may couple with the second functional group of a previously coupled synthon that has not been coupled, which may be deprotected for that step. The stepwise method may be carried out with synthons on solid phase support. Scheme 8 illustrates a stepwise preparation of module SC8-1.

Compound S8-2 is reacted with S8-3, in which the phenol is protected as the benzyl ether and the nitrogen is shown as protected with a group "P," which can be any of a large number of protecting groups well-known in the art, in the presence of methanesulfonyl chloride (Endo, K.; Takahashi, H. *Heterocycles,* 1999, 51, 337), to give S8-4. Removal of the N-protecting group give the free amine S8-5, which can be coupled with synthon S8-6 using any standard peptide coupling reaction such as BOP/HOBt to give S8-7. Deprotection/coupling is repeated, alternating synthons S8-3 and S8-6 until a linear construct with eight residues is obtained. The remaining acid and amine protecting groups on the 8-mer are removed and the oligomer is cyclized, see e.g., Caba, J. M., et al., *J. Org. Chem.,* 2001, 66:7568 (PyAOP cyclization) and Tarver, J. E. et al., *J. Org. Chem.,* 2001, 66:7575 (active ester cyclization). The R group is H or an organic functional group, and X is N, O, or S. Examples of solid supports include Wang resin, hydrogels, silica gels, sepharose, sephadex, agarose, and inorganic solids. Using a solid support might simplify the procedure by obviating purification of intermediates along the way. The final cyclization may be done in a solid phase mode. A "safety-catch linker" approach (Bourne, G. T., et al., *J. Org. Chem.,* 2001, 66:7706) may be used to obtain cyclization and resin cleavage in a single operation.

SCHEME 8

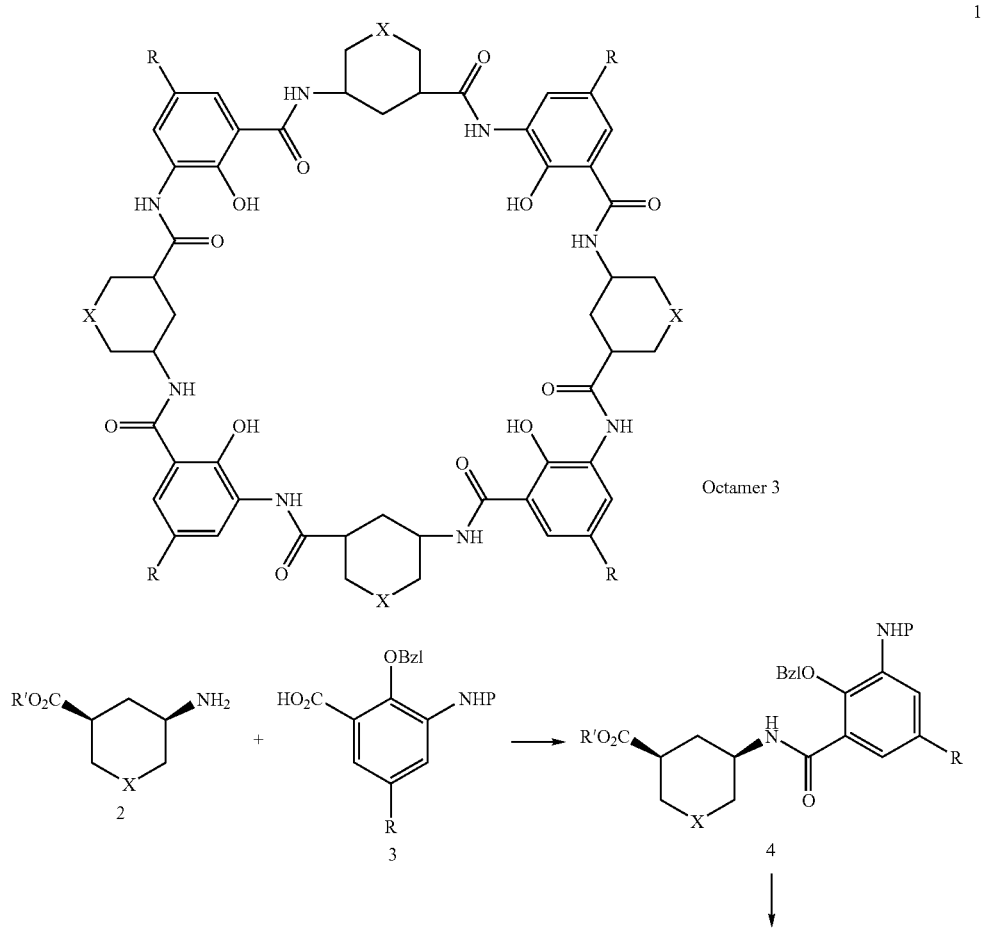

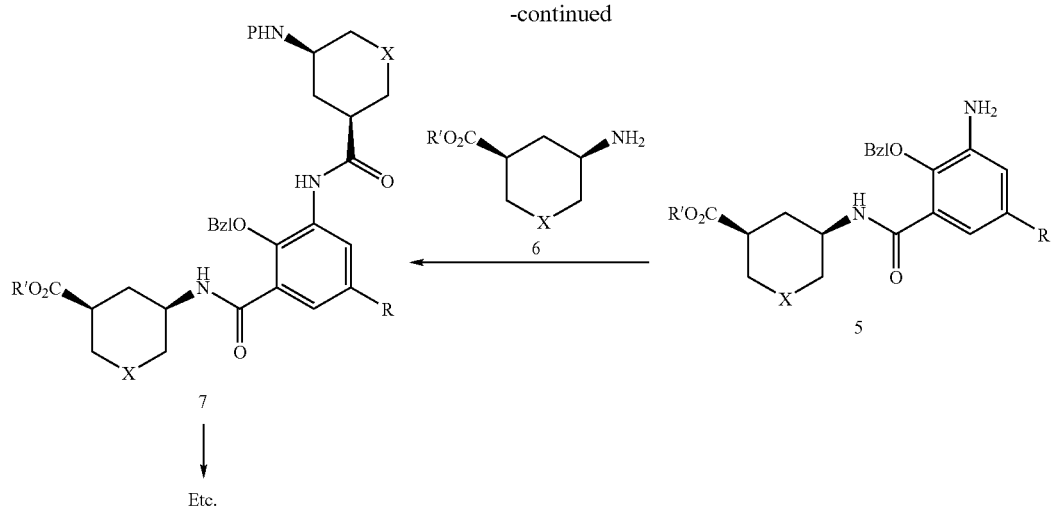
In another variation, a concerted method involves contacting two or more different synthons and a linker molecule as shown in Scheme 9, where R may be an alkyl group or other lipophilic group.
SCHEME 9
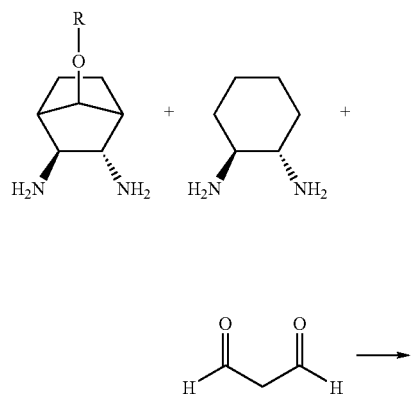
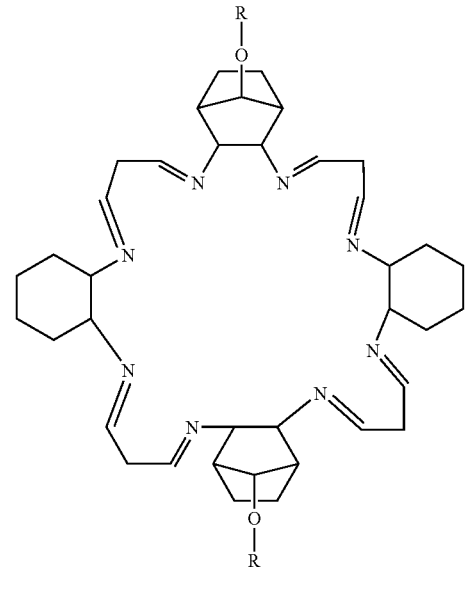
Tetramer-monobicycloheptane
In another variation, a stepwise linear method involves various synthons and a solid phase support as shown in Scheme 10.
SCHEME 10
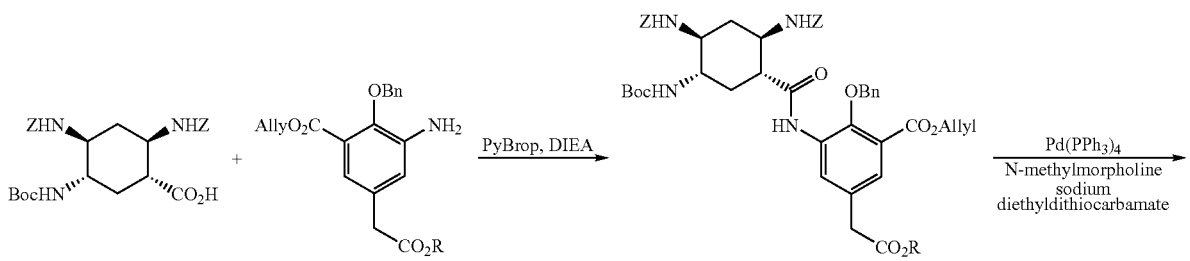

-continued
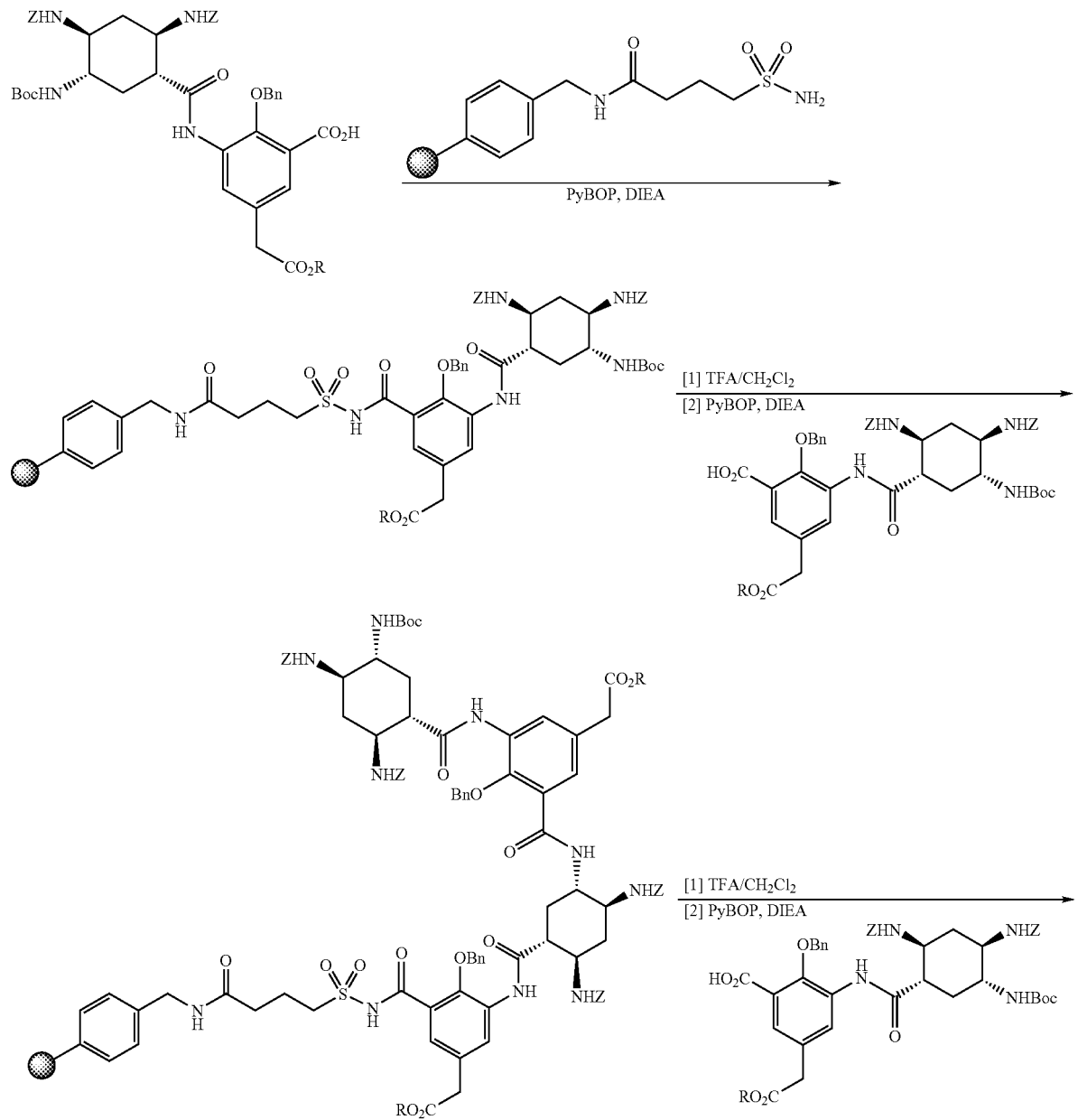

-continued
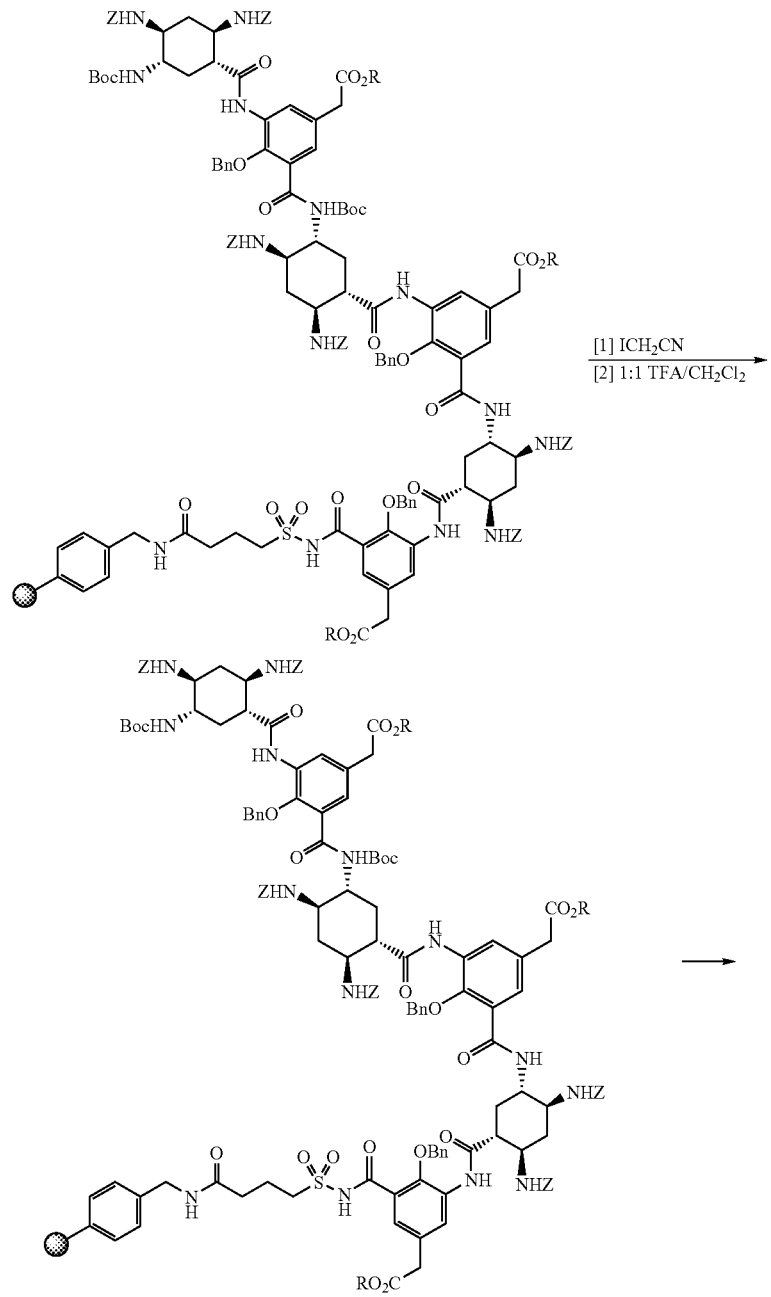

-continued

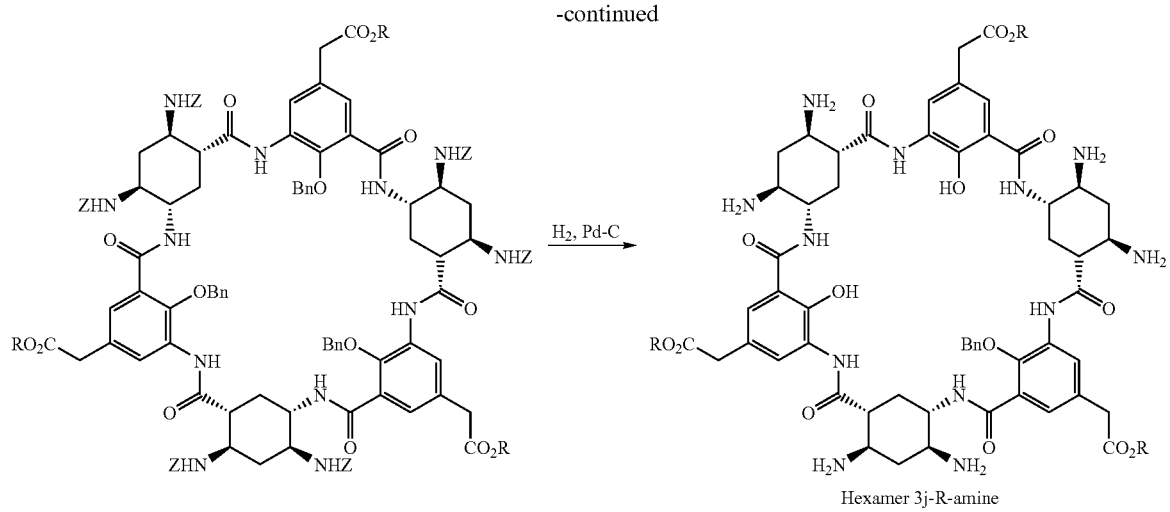

Hexamer 3j-R-amine

In another variation, a stepwise convergent method involves synthon trimers and a solid phase support as shown in Scheme 11. This method can also be done without the solid phase support using trimers in solution.

SCHEME 11

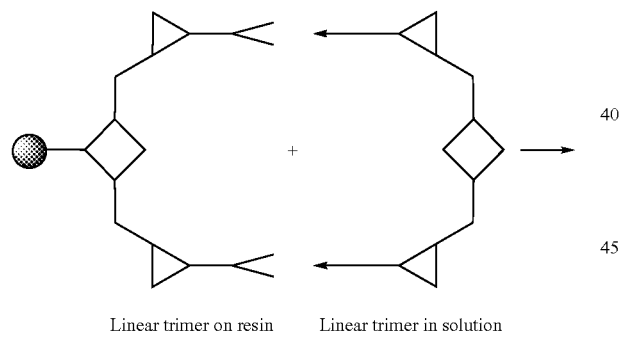

Linear trimer on resin    Linear trimer in solution

-continued

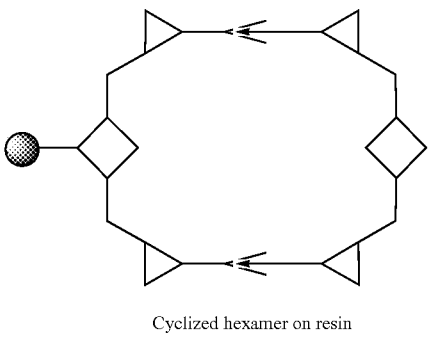

Cyclized hexamer on resin

In another variation, a template method involves synthons brought together by a template as shown in Scheme 12. Some aspects of this approach (and an $Mg^{2+}$ template) are given in Dutta et al. *Inorg. Chem.* 1998, 37, 5029.

SCHEME 12

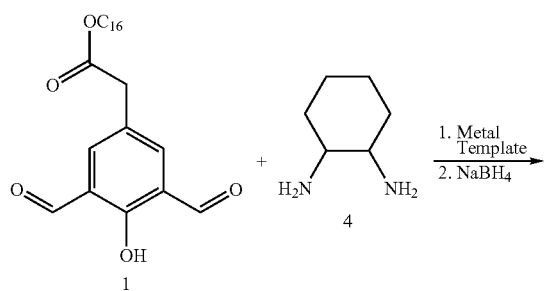

-continued
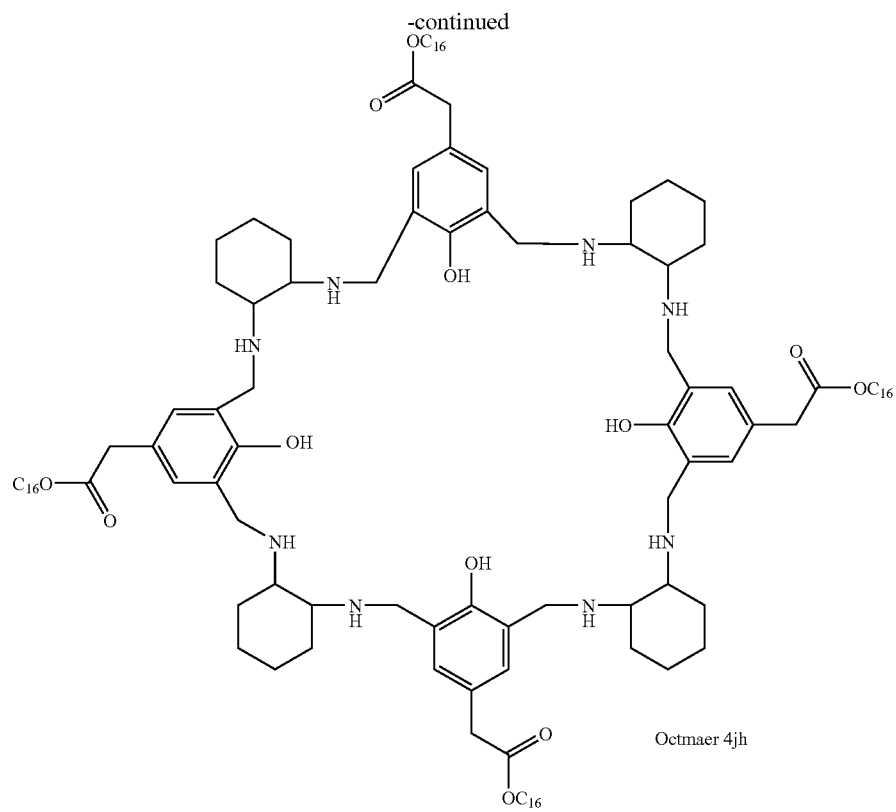
Octmaer 4jh
In another variation, a linker molecule method involves cyclizing synthons in solution as shown in Scheme 13.
SCHEME 13
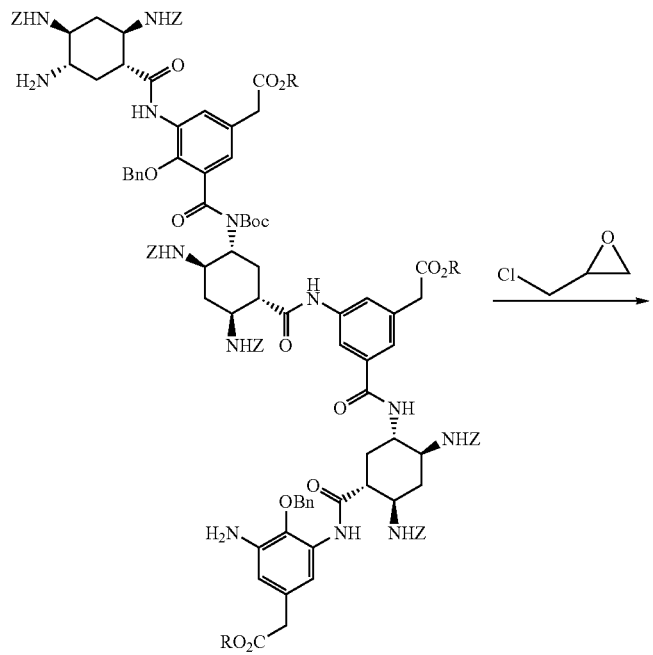

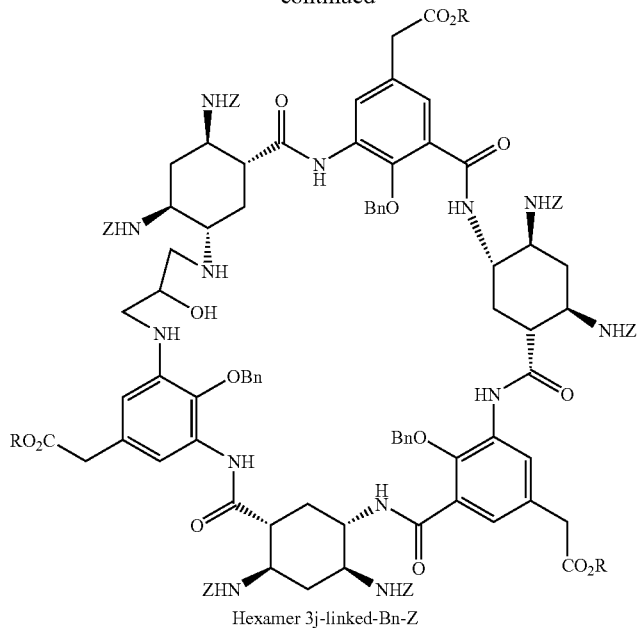

Hexamer 3j-linked-Bn-Z

Reagents for the following examples were obtained from Aldrich Chemical Company and VWR Scientific Products. All reactions were carried out under nitrogen or argon atmosphere unless otherwise noted. Solvent extracts of aqueous solutions were dried over anhydrous $Na_2SO_4$. Solutions were concentrated under reduced pressure using a rotary evaporator. Thin layer chromatography (TLC) was done on Analtech Silica gel GF (0.25 mm) plates or on Machery-Nagel Alugram Sil G/UV (0.20 mm) plates. Chromatograms were visualized with either UV light, phosphomolybdic acid, or $KMnO_4$. All compounds reported were homogeneous by TLC unless otherwise noted. HPLC analyses were performed on a Hewlett Packard 1100 system using a reverse phase C-18 silica column. Enantiomeric excess was determined by HPLC using a reverse phase (l)-leucine silica column from Regis Technologies. All $^1$[H] and $^{13}$[C] NMR spectra were collected at 400 MHz on a Varian Mercury system. Electrospray mass spectra were obtained by Synpep Corp., or on a Thermo Finnigan LC-MS system.

Example 1

2,6-Diformyl-4-bromophenol

Hexamethylenetetramine (73.84 g, 526 mmol) was added to TFA (240 mL) with stirring. 4-Bromophenol (22.74 g, 131 mmol) was added in one portion and the solution heated in an oil bath to 120° C. and stirred under argon for 48 h. The reaction mixture was then cooled to ambient temperature. Water (160 mL) and 50% aqueous $H_2SO_4$ (80 mL) were added and the solution stirred for an additional 2 h. The reaction mixture was poured into water (1600 mL) and the resulting precipitate collected on a Büchner funnel. The precipitate was dissolved in ethyl acetate (EtOAc) and the solution was dried over $MgSO_4$. The solution was filtered and the solvent removed on a rotary evaporator. Purification by column chromatography on silica gel (400 g) using a gradient of 15-40% ethyl acetate in hexanes resulted in a isolation of the product as a yellow solid (18.0 g, 60%).

$^1$H NMR (400 MHz, $CDCl_3$) δ 11.54 (s, 1H, OH), 10.19 (s, 2H, CHO), 8.08 (s, 2 H, ArH).

Example 2

2,6-Diformyl-4-(dodecyn-1-yl)phenol 2,6-Diformyl-4-bromophenol (2.50 g, 10.9 mmol), 1-dodecyne (2.00 g, 12.0 mmol), CuI (65 mg, 0.33 mmol), and bis(triphenylphosphine)palladium)II) dichloride were suspended in degassed acetonitrile (MeCN) (5 mL) and degassed benzene (1 mL). The yellow suspension was sparged with argon for 30 min and degassed $Et_3N$ (1 mL) was added. The resulting brown suspension was sealed in a pressure vial, warmed to 80° C. and held there for 12 h. The mixture was then partitioned between EtOAc and $KHSO_4$ solution. The organic layer was separated, washed with brine, dried ($MgSO_4$) and concentrated under reduced pressure. The dark yellow oil was purified by column chromatography on silica gel (25% $Et_2O$ in hexanes) to give 1.56 g (46%) of the title compound.

$^1$H NMR (400 MHz, $CDCl_3$) δ11.64 (s, 1H, OH), 10.19 (s, 2H, CHO), 7.97 (s, 2H, ArH), 2.39 (t, 2H, J=7.2 Hz, propargylic), 1.59 (m, 3H, aliphatic), 1.43, (m, 2H, aliphatic), 1.28 (m, 11H, aliphatic), 0.88 (t, 3H, J=7.0 Hz, $CH_3$).

$^{13}$C NMR (400 MHz, $CDCl_3$) δ 192.5, 162.4, 140.3, 122.8, 116.7, 91.4, 77.5, 31.9, 29.6, 29.5, 29.3, 29.1, 28.9, 28.5, 22.7, 19.2, 14.1.

MS (FAB): Calcd. for $C_{20}H_{27}O_3$ 315.1960; found 315.1958 $[M+H]^+$.

Example 3

2,6-Diformyl-4-(dodecen-1-yl)phenol 2,6-Diformyl-4-bromophenol (1.00 g, 4.37 mmol), 1-dodecene (4.8 mL, 21.7 mmol), 1.40 g tetrabutylammonium bromide (4.34 mmol), 0.50 g NaHCO$_3$ (5.95 mmol), 1.00 g LiCl (23.6 mmol) and 0.100 g palladium diacetate (Pd(OAc)$_2$) (0.45 mmol) were combined in 30 mL degassed anhydrous dimethylformamide (DMF). The mixture was sparged with argon for 10 min and then sealed in a pressure vial which was warmed to 82° C. and held for 40 h. The crude reaction mixture was partitioned between CH$_2$Cl$_2$ and 0.1 M HCl solution. The organic layer was washed with 0.1 M HCl (2×), brine (2×), and saturated aqueous NaHCO$_3$ (2×), dried over MgSO$_4$ and concentrated under reduced pressure. The dark yellow oil was purified by column chromatography on silica gel (25% hexanes in Et$_2$O) to give 0.700 g (51%) of the title compound as primarily the Z isomer.

$^1$H NMR (400 MHz, CDCl$_3$) δ11.50 (s, 1H, OH), 10.21 (s, 2H, CHO), 7.95 (s, 2 H, ArH), 6.38 (d, 1H, vinyl), 6.25 (m, 1H, vinyl), 2.21 (m, 2H, allylic), 1.30-1.61 (m, 16H, aliphatic), 0.95 (t, 3H, J=7.0 Hz, CH$_3$).

MS (FAB): Calcd. for C$_{20}$H$_{27}$O$_3$ 315.20; found 315.35 [M—H]$^-$.

Example 4

(1R,6S)-6-Methoxycarbonyl-3-cyclohexene-1-carboxylic Acid (S1-2)

S1-1 (15.0 g, 75.7 mmol) was suspended in pH 7 phosphate buffer (950 mL). Pig liver esterase (2909 units) was added, and the mixture stirred at ambient temperature for 72 h with the pH maintained at 7 by addition of 2M NaOH. The reaction mixture was washed with ethyl acetate (200 mL), acidified to pH 2 with 2M HCl, and extracted with ethyl acetate (3×200 mL). The extracts were combined, dried, and evaporated to afford 13.8 g (99%) of S1-2.

$^1$H NMR: (CDCl$_3$) δ 2.32 (dt, 2H, 2$_{ax}$- and 5$_{ax}$-H's), 2.55 (dt, 2H, 2$_{eq}$- and 5$_{eq}$-H's), 3.00 (m, 2H, 1- and 6-H's), 3.62 (s, 3H, CO$_2$Me), 5.61 (m, 2H, 3- and 4-H's).

Example 5

Methyl (1S,6R)-6-Benzyloxycarbonylaminocyclohex-3-enecarboxylate (S1-3)

S1-2 (10.0 g, 54.3 mmol) was dissolved in benzene (100 mL) under N$_2$. Triethylamine (13.2 g, 18.2 mL, 130.3 mmol) was added followed by DPPA (14.9 g, 11.7 mL, 54.3 mmol). The solution was refluxed for 20 h. Benzyl alcohol (5.9 g, 5.6 mL, 54.3 mmol) was added and reflux continued for 20 h. The solution was diluted with EtOAc (200 mL), washed with saturated aqueous NaHCO$_3$ (2×50 mL), water (20 mL), and saturated aqueous NaCl (20 mL), dried and evaporated to give 13.7 g (87%) of S1-3.

$^1$H NMR: (CDCl$_3$) δ 2.19 (dt, 1H, 5$_{ax}$-H), 2.37 (tt, 2H, 2$_{ax}$- and 5$_{eq}$-H's), 2.54 (dt, 1H, 2$_{eq}$-H), 2.82 (m, 1H, 1-H), 3.65 (s, 3H, CO$_2$Me), 4.28 (m, 1H, 6-H), 5.08 (dd, 2H, CH$_2$Ar), 5.42 (d, 1H, NH), 5.62 (ddt, 2H, 3- and 4-H's), 7.35 (m, 5H, Ar H's).

Example 6

(1S,6R)-6-Benzyloxycarbonylaminocyclohex-3-enecarboxylic acid (S1-4)

S1-3 (23.5 g, 81.3 mmol) was dissolved in MeOH (150 mL) and the solution cooled to 0° C. 2M NaOH (204 mL, 0.41 mol) was added, the mixture allowed to come to ambient temperature and then it was stirred for 48 h. The reaction mixture was diluted with water (300 mL), acidified with 2M HCl, and extracted with dichloromethane (250 mL), dried, and evaporated. The residue was recrystallized from diethyl ether to give 21.7 (97%) of S1-4.

$^1$H NMR: (CDCl$_3$) δ 2.20 (d, 1H, 5$_{ax}$-H), 2.37 (d, 2H, 2$_{ax}$- and 5$_{eq}$-H's), 2.54 (d, 1H, 2$_{eq}$-H), 2.90 (br s, 1H, 1-H), 4.24 (br s, 1H, 6-H), 5.08 (dd, 2H, CH$_2$Ar), 5.48 (d, 1H, NH), 5.62 (dd, 2H, 3- and 4-H's), 7.35 (m, 5H, Ar H's).

Example 7

(1S,2R,4R,5R)-2-Benzyloxycarbonylamino-4-iodo-7-oxo-6-oxabicyclo[3.2.1]octane (S1-5)

S1-4 (13.9 g, 50.5 mmol) was dissolved in dichloromethane (100 mL) under N$_2$, 0.5 M NaHCO$_3$ (300 mL), KI (50.3 g, 303.3 mmol), and iodine (25.6 g, 101 mmol) were added and the mixture stirred at ambient temperature for 72 h. The mixture was diluted with dichloromethane (50 mL) and the organic phase separated. The organic phase was washed with saturated aqueous Na$_2$S$_2$O$_3$ (2×50 mL), water (30 mL), and saturated aqueous NaCl (20 mL), dried and evaporated to afford 16.3 g (80%) of S1-5.

$^1$H NMR: (CDCl$_3$) δ 2.15 (m, 1H, 8$_{ax}$-H), 2.42 (m, 2H, 3$_{ax}$- and 8$_{eq}$-H's), 2.75 (m, 2H, 1- and 3$_{eq}$-H's), 4.12 (br s, 1H, 2-H), 4.41 (t, 1H, 4-H), 4.76 (dd, 1H, 5-H), 4.92 (d, 1 H, NH), 5.08 (dd, 2H, CH$_2$Ar), 7.35 (m, 5H, Ar H's).

Example 8

(1S,2R,5)-2-Benzyloxycarbonylamino-7-oxo-6-oxabicyclo[3.2.1]oct-3-ene (S1-6).

S1-5 (4.0 g, 10 mmol) was dissolved in benzene (50 mL) under N$_2$. 1,8-Diazabicyclo[5.4.0]undec-7-ene (DBU) (1.8 g, 12 mmol) was added and the solution refluxed for 16 h. The precipitate was filtered and the filtrate was diluted with EtOAc (200 mL). The filtrate was washed with 1M HCl (20 mL), saturated aqueous Na$_2$S$_2$O$_3$ (20 mL), water (20 mL), and saturated aqueous NaCl (20 mL), dried and evaporated to give 2.2 g (81%) S1-6.

$^1$H NMR: (CDCl$_3$) δ 2.18 (d, 1H, 8$_{ax}$-H), 2.39 (m, 1H, 8$_{eq}$-H), 3.04 (t, 1H, 1-H), 4.70 (m, 1H, 5-H), 4.82 (t, 1H, 2-H), 5.15 (dd, 3H, CH$_2$Ar and NH), 5.76 (d, 1H, 4-H), 5.92 (m, 1H, 3-H), 7.36 (s, 5H, Ar H's).

Example 9

(1S,2R,5R)-Methyl 2-Benzyloxycarbonylamino-5-hydroxycyclohex-3-enecarboxylate (S1-7)

S1-6 (9.0 g, 33 mmol) was suspended in MeOH (90 mL) and cooled to 0° C. NaOMe (2.8 g, 52.7 mmol) was added and the mixture stirred for 3 h during which time a solution gradually formed. The solution was neutralized with 2M HCl, diluted with saturated aqueous NaCl (200 mL), and extracted with dichloromethane (2×100 mL). The extracts were combined, washed with water (20 mL) and saturated aqueous NaCl (20 ml), dried, and evaporated. The residue was flash chromatographed (silica gel (250 g), 50:50 hexane/EtOAc) to give 8.5 g (85%) of S1-7.

$^1$H NMR: (CDCl$_3$) δ 1.90 (m, 1H, 6$_{ax}$-H), 2.09 (m, 1H, 6$_{eq}$-H), 2.81 (m, 1H, 1-H), 3.55 (s, 3H, CO$_2$Me), 4.15 (m, 1H,

5-H), 4.48 (t, 1H, 2-H), 5.02 (dd, 2H, CH$_2$Ar), 5.32 (d, 1H, NH), 5.64 (dt, 1H, 4-H), 5.82 (dt, 1H, 3-H), 7.28 (s, 5H, Ar H's).

Example 10

(1S,2R,5S)-Methyl 2-Benzyloxycarbonylamino-5-tbutoxycarbonylaminocyclohex-3-enecarboxylate (S1-8)

S1-7 (7.9 g, 25.9 mmol) was dissolved in dichloromethane (150 mL) and cooled to 0° C. under N$_2$. Triethylamine (6.3 g, 8.7 mL, 62.1 mmol) and methanesulfonyl chloride (7.1 g, 62.1 mmol) were added and the mixture stirred at 0° C. for 2 h. (n-Bu)$_4$NN$_3$(14.7 g, 51.7 mmol) in dichloromethane (50 mL) was added and stirring continued at 0° C. for 3 h followed by 15 h at ambient temperature. The mixture was cooled to 0° C. and P(n-Bu)$_3$ (15.7 g, 19.3 mL, 77.7 mmol) and water (1 mL) were added and the mixture stirred at ambient temperature for 24 h. Di-tert-butyl dicarbonate (17.0 g, 77.7 mmol) was added and stirring continued for 24 h. The solvent was removed, the residue dissolved in 2:1 hexane/EtOAc (100 mL), the solution filtered, and evaporated. The residue was flash chromatographed (silica gel (240 g), 67:33 hexane/EtOAc) to give 5.9 g (56%) of S1-8.

$^1$H NMR: (CDCl$_3$) δ 1.40 (s, 9H, Boc H's), 1.88 (m, 1H, 6$_{ax}$-H), 2.21 (m, 1H, 6$_{eq}$-H), 2.95 (m, 1H, 1-H), 3.60 (s, 3H, CO$_2$Me), 4.15 (d, 1H, Boc NH), 4.50 (m, 2H, 2- and 5-H's), 5.02 (s, 2H, CH$_2$Ar), 5.38 (d, 1H, Z NH), 5.65 (m, 2H, 3- and 4-H's), 7.30 (s, 5H, Ar H's).

Example 11

(1R,2R,5S)-Methyl 2-Benzyloxycarbonylamino-5-t-butoxycarbonylaminocyclohex-3-enecarboxylate (S1-9)

S1-8 (1.1 g, 2.7 mmol) was suspended in MeOH (50 mL). NaOMe (0.73 g, 13.6 mmol) was added and the mixture refluxed for 18 h after which 0.5 M NH$_4$Cl (50 mL) was added and the resulting precipitate collected. The filtrate was evaporated and the residue triturated with water (25 mL). The insoluble portion was collected and combined with the original precipitate to give 0.85 g (77%) of S1-9.

$^1$H NMR: (CDCl$_3$) δ 1.38 (s, 9H, Boc H's), 1.66 (m, 1H, 6$_{ax}$-H), 2.22 (d, 1H, 6$_{eq}$-H), 2.58 (t, 1H, 1-H), 3.59 (3, 3 H, CO$_2$Me), 4.22 (br s, 1H, Boc NH), 4.50 (m, 2H, 2- and 5-H's), 4.75 (d, 1H, Z NH), 5.02 (s, 2H, CH$_2$Ar), 5.62 (s, 2H, 3- and 4-H's), 7.30 (s, 5H, Ar H's).

Example 12

(1R,2R,5,S)-2-Benzyloxycarbonylamino-5-t-butoxycarbonylaminocyclohex-3-enecarboxylic acid (S1-10)

S1-9 (0.85 g, 2.1 mmol) was suspended in 50:50 MeOH/dichloromethane (5 mL) and cooled to 0° C. under N$_2$ after which 2M NaOH (2.0 mL) was added and the mixture stirred at ambient temperature for 16 h. The mixture was acidified with 2M HCl upon which a white precipitate formed. The precipitate was collected, washed with water and hexane, and dried to give 0.74 g (90%) of S1-10.

$^1$H NMR: (CD$_3$OD) δ 1.42 (s, 9H, Boc H's), 1.66 (m, 1H, 6$_{ax}$-H), 2.22 (d, 1H, 6$_{eq}$-H), 2.65 (t, 1H, 1-H), 4.18 (m, 1H, 5-H), 4.45 (m, 1H, 5-H), 5.04 (s, 2H, CH$_2$Ar), 5.58 (m, 2 H, 3- and 4-H's), 7.35 (s, 5H, Ar H's).

Example 13

(1R,2R,5S)-2-Benzyloxycarbonylamino-5-t-butoxycarbonylamino-1-(2-trimethylsilyl)ethoxycarbonylaminocyclohex-3-ene (S1-11)

S1-10 (3.1 g, 7.9 mmol) was dissolved in THF (30 mL) under N$_2$ and cooled to 0° C. Triethylamine (1.6 g, 2.2 mL, 15.9 mmol) was added followed by ethyl chloroformate (1.3 g, 1.5 mL, 11.8 mmol). The mixture was stirred at 0° C. for 1 h. A solution of NaN$_3$ (1.3 g, 19.7 mmol) in water (10 mL) was added and stirring at 0° C. was continued for 2 h. The reaction mixture was partitioned between EtOAc (50 mL) and water (50 mL). The organic phase was separated, dried, and evaporated. The residue was dissolved in benzene (50 mL) and refluxed for 2 h. 2-Trimethylsilylethanol (1.0 g, 1.2 mL, 8.7 mmol) was added and reflux continued for 3 h. The reaction mixture was diluted with EtOAc (200 mL), washed with saturated aqueous NaHCO$_3$ (50 mL), water (20 mL), and saturated aqueous NaCl (20 mL), dried and evaporated. The residue was flash chromatographed (silica gel (100 g), 67:33 hexane/EtOAc) to give 3.1 g (77%) of S1-11.

$^1$H NMR: (CDCl$_3$) δ −0.02 (s, 9H, TMS), 0.90 (t, 3H, CH$_2$TMS), 1.40 (s, 9H, Boc H's), 2.38 (m, 1H, 6$_{eq}$-H), 3.62 (m, 1H, 1-H), 4.08 (m, 2H, OCH$_2$CH$_2$TMS), 4.18 (m, 1 H), 4.38 (m, 1H), 4.62 (m, 1H), 5.07 (dd, 2H, CH$_2$Ar), 5.18 (m, 1H), 5.26 (m, 1H), 5.58 (d, 1H, olefinic H), 5.64 (d, 2H, olefinic H), 7.30 (s, 5, Ar H's).

Example 14

(1R,2R,5S)-2-Benzyloxycarbonylamino-1,5-diaminocyclohex-3-ene (S1-12)

S1-11 (2.5 g, 4.9 mmol) was added to TFA (10 mL) and the solution stirred at ambient temperature for 16 h after which the solution was evaporated. The residue was dissolved in water (20 mL), basified to pH 14 with KOH and extracted with dichloromethane (3×50 mL). The extracts were combined, washed with water (20 mL), dried and evaporated to give 1.1 g (85%) of S1-12.

$^1$H NMR: (CDCl$_3$) δ 1.30 (m, 1H, 6$_{ax}$-H), 2.15 (br d, 1H, 6$_{eq}$-H), 2.68 (m, 1H, 1-H), 3.42 (br s, 1H, 5-H), 3.95 (m, 1H, 2-H), 4.85 (d, 1H, Z NH), 5.08 (t, 2H, CH$_2$Ar), 5.45 (d, 1H, 4-H), 5.62 (d, 1H, 3-H), 7.32 (s, 5H, Ar H's). ESCI MS m/e 262 M+1.

Example 15

Isolation of S1b-2 was accomplished using the following procedure: Using Schlenk technique 5.57 g (10.0 mmol) of methyl ester compound, S1b-1, was dissolved in 250 mL of THF. In another flask LiOH (1.21 g, 50.5 mmol) was dissolved in 50 mL water and de-gassed by bubbling N$_2$ through the solution using a needle for 20 minutes. The reaction was started transferring the base solution into the flask containing S1b-1 over one minute with rapid stirring. The mixture was stirred at room temperature and work-up initiated when the starting material S1b-1 was completely consumed (Using a solvent system of 66% EtOAc/33% Hexane and developing with phosphomolybdic acid reagent (Aldrich #31,927-9) the starting material S1b-1 has an Rf of 0.88 and the product streaks with an Rf of approx. 0.34 to 0.64.). The reaction usually takes 2 days. Work-Up: The THF was removed by vacuum transfer until about the same volume is left as water added to the reaction, in this case 50 mL. During this the reaction solution forms a white mass that adheres to the stir bar surrounded by clear yellow solution. As the THF is being removed a separatory funnel is set up including a funnel to pour in the reaction solution and an Erlenmeyer flask is placed underneath the separatory funnel. Into the Erlenmeyer flask is added some anhydrous $Na_2SO_4$. This apparatus should be set up before acidification is started. (It is important to set up the separatory funnel and Erlenmeyer flask etc. before acidification of the reaction solution to enable separation of phases and extraction of the product away from the acid quickly once the solution attains a pH close to 1. If the separation is not preformed rapidly the Boc functional group will be hydrolyzed significantly reducing the yield.) Once the volatiles are sufficiently removed, $CH_2Cl_2$ (125 mL) and water (65 mL) are added and the reaction flask cooled in an ice bath. The solution is stirred rapidly and 5 mL aliquots of 1N HCl are added by syringe and the reaction solution tested with pH paper. Acid is added until the spot on the pH paper shows red (not orange) around the edge indicating a pH is 1 to 2 has been achieved (The solution being tested is a mixture of $CH_2Cl_2$ and water so the pH paper will show the accurate measurement at the edge of the spot and not the center.) and the phases are separated by quickly pouring the solution into the separatory funnel. As the phases separate the stopcock is turned to release the $CH_2Cl_2$ phase (bottom) into the Erlenmeyer flask and swirl the flask to allow the drying agent to absorb water in the solution. (At this scale of this procedure 80 mL of 1N HCl was used.) Soon after phase separation the aqueous phase is extracted with $CH_2Cl_2$ (2×100 mL), dried over anhydrous $Na_2SO_4$ and the volatiles removed to produce 5.37 g/9.91 mmoles of a beautiful white microcrystals reflecting a 99.1% yield. This product can not be purified by chromatography since that process would also hydrolyze the Boc functional group on the column.

$^1$H NMR (400 MHz, $CDCl_3$) δ 7.33, 7.25 (5H, m, Ph), 6.30 (1H, d, NH), 5.97 (1H, d, NH), 5.10 (2H, m, $CH_2$Ph), 4.90 (1H, d, NH), 3.92, 3.58, 3.49 (1H, m, CHNH), 2.96, 2.48, 2.04, 1.95, 1.63 (1H, m, $CH_2$CHNH), 1.34 (9H, s, $CCH_3$).

IR (crystalline, $cm^{-1}$) 3326 br w, 3066 w, 3033 w, 2975 w, 2940 w sh, 1695 vs, 1506 vs, 1454 m sh, 1391 w, 1367 m, 1300 m sh, 1278 m sh, 1236 s, 1213 w sh, 1163 vs, 1100 w, 1053 m, 1020 m, 981 w sh, 910 w, 870 m, 846 w, 817 w, 775 w sh, 739 m, 696 m.

Example 16

Di-(l)-menthyl bicyclo[2.2.1]hept-5-ene-7-anti-(trimethylsilyl)-2-endo-3-exo-dicarboxylate (S4-26)

To a solution of S4-25 (6.09 g, 0.0155 mol) in toluene (100 mL) was added diethylaluminum chloride (8.6 mL of a 1.8 M solution in toluene) at −78° C. under nitrogen and the mixture was stirred for 1 hour. To the resulting orange solution was added S2-14 (7.00 g, 0.0466 mol) dropwise as a −78° C. solution in toluene (10 mL). The solution was kept at −78° C. for 2 hours, followed by slow warming to room temperature overnight. The aluminum reagent was quenched with a saturated solution of ammonium chloride (50 mL). The aqueous layer was separated and extracted with methylene chloride (100 mL) which was subsequently dried over magnesium sulfate. Evaporation of the solvent left a yellow solid that was purified by column chromatography (10% ethyl acetate/hexanes) to give S4-26 as a while solid (7.19 g, 0.0136 mol, 87% yield).

$^1$H NMR: ($CDCl_3$) δ 0.09 (s, 9H, $SiMe_3$), 0.74-1.95 (multiplets, 36 H, menthol), 2.72 (d, 1H, α-menthyl carbonyl CH), 3.19 (bs, 1H, bridgehead CH), 3.30 (bs, 1H, bridgehead CH), 3.40 (t, 1H, α-menthyl carbonyl CH), 4.48 (d of t, 1H, α-menthyl ester CH), 4.71 (d of t, 1 H, α-menthyl ester CH), 5.92 (d of d, 1H, CH═CH), 6.19 (d of d, 1H, CH═CH).

Example 17

5-exo-Bromo-3-exo-(l)-menthylcarboxybicyclo[2.2.1]heptane-7-ant(trimethylsilyl)-2,6-carbolactone (S4-27)

A solution of bromine (3.61 g, 0.0226 mol) in methylene chloride (20 mL) was added to a stirring solution of S4-26 (4.00 g, 0.00754 mol) in methylene chloride (80 mL). Stirring was continued at room temperature overnight. The solution was treated with 5% sodium thiosulfate (150 mL), and the organic layer separated and dried over magnesium sulfate. The solvent was evaporated at reduced pressure, and the crude product purified by column chromatography (5% ethyl acetate/hexanes) to give S4-27 as a white solid (3.53 g, 0.00754 mol, 99% yield).

$^1$H NMR: ($CDCl_3$) δ-0.19 (s, 9H, $SiMe_3$), 0.74-1.91 (multiplets, 18 H, menthol), 2.82 (d, 1H, α-lactone carbonyl CH), 3.14 (bs, 1H, lactone bridgehead CH), 3.19 (d of d, 1H, bridgehead CH), 3.29 (t, 1H, α-menthyl carbonyl CH), 3.80 (d, 1H, α-lactone ester), 4.74 (d of t, 1H, α-menthyl ester CH), 4.94 (d, 1H, bromo CH).

Example 18

Bicyclo[2.2.1]hept-5-ene-7-syn-(hydroxy)-2-exo-methyl-3-endo-(l)-menthyl dicarboxylate (S4-28)

S4-27 (3.00 g, 0.00638 mol) was dissolved in anhydrous methanol (150 mL), silver nitrate (5.40 g, 0.0318 mol) added and the suspension refluxed for 3 days. The mixture was cooled, filtered through Celite and the solvent evaporated to give an oily residue. Purification by column chromatography gave S4-28 as a light yellow oil (1.72 g, 0.00491 mol, 77% yield).

$^1$H NMR: ($CDCl_3$) δ 0.75-2.02 (multiplets, 18 H, menthol), 2.83 (d, 1H, α-menthyl carbonyl CH), 3.03 (bs, 1H, bridgehead CH), 3.14 (bs, 1H, bridgehead CH), 3.53 (t, 1 H, α-methyl carbonyl CH), 3.76 (s, 3H, $CH_3$), 4.62 (d of t, 1H, α-menthyl ester CH), 5.87 (d of d, 1H, CH═CH), 6.23 (d of d, 1H, CH═CH).

Example 19

2-exo-Methyl-3-endo-(l)-menthylbicyclo[2.2.1]hept-5-ene-7-syn(benzyloxy) dicarboxylate (S4-29)

Benzyl bromide (1.20 g, 0.0070 mol) and silver oxide (1.62 g, 0.0070 mol) were added to a stirring solution of S4-28 (0.490 g, 0.00140 mol) in DMF (25 mL). The suspension was stirred overnight and then diluted with ethyl acetate (100 mL). The solution was washed repeatedly with water followed by 1 N lithium chloride. The organic layer was separated and dried with magnesium sulfate. The solvent was evaporated under reduced pressure and the crude product was purified by column chromatography on silica gel to give S4-29 as an oil (0.220 g, 0.000500 mol, 36% yield).

$^1$H NMR: ($CDCl_3$) δ 0.74-2.08 (multiplets, 18 H, menthol), 2.83 (d, 1H, α-menthyl carbonyl CH), 3.18 (bs, 1H, bridgehead CH), 3.44 (bs, 1H, bridgehead CH), 3.52 (t, 1H, bridge CH), 3.57 (s, 3H, $CH_3$), 3.68 (t, 1H, α-methyl carbonyl CH), 4.42 (d of d, 2H, benzyl —$CH_2$—), 4.61 (d of t, 1H, α-menthyl ester CH), 5.89 (d of d, 1H, CH=CH), 6.22 (d of d, 1H, CH=CH), 7.25-7.38 (m, 5H, C$_6$H$_5$).

Example 20

Bicyclo[2.2.1]hept-5-ene-7-syn-(benzyloxy)-2-exo-carboxy-3-endo-(4-menthyl carboxylate (S4-30)

S4-29 (0.220 g, 0.00050 mol) was added to a mixture of tetrahydrofuran (1.5 mL), water (0.5 mL), and methanol (0.5 mL). Potassium hydroxide (0.036 g, 0.00065 mol) was added and the solution stirred at room temperature overnight. The solvent was evaporated under reduced pressure and the residue purified by column chromatography (10% ethyl acetate/hexanes) to give S4-30 (0.050 g, 0.00012 mol, 23% yield).
$^1$H NMR: (CDCl$_3$) δ 0.73-2.01 (multiplets, 18 H, menthol), 2.85 (d, 1H, α-menthyl carbonyl CH), 3.18 (bs, 1H, bridgehead CH), 3.98 (bs, 1H, bridgehead CH), 3.53 (bs, 1 H, bridge CH), 3.66 (t, 1H, α-methyl carbonyl CH), 4.44 (d of d, 2H, benzyl —CH$_2$—), 4.63 (d of t, 1H, α-menthyl ester CH), 5.90 (d of d, 1H, CH=CH), 6.23 (d of d, 1H, CH=CH), 7.25-7.38 (m, 5H, C$_6$H$_5$).
Mass Spec: calculated for C$_{26}$H$_{34}$O$_5$ 426.24; found 425.4 (M-1) and 851.3 (2M-1).

Example 21

Bicyclo[2.2.1]hept-5-ene-7-syn(benzyloxy)-2-exo-(trimethylsilylethoxycarbonyl)-amino-3-endo-(l)-menthyl carboxylate (S4-31)

To a solution of S4-30 in benzene is added triethylamine and diphenylphosphoryl azide. The solution is refluxed for 24 hours then cooled to room temperature. Trimethylsilylethanol is added, and the solution refluxed for an additional 48 hours. The benzene solution is partitioned between ethyl acetate and 1 M sodium bicarbonate. The organic layers are combined, washed with 1 M sodium bicarbonate and dried over sodium sulfate. The solvent is evaporated under reduced pressure to give the crude Curtius reaction product.

Example 22

Bicyclo[2.2.1]heptane-7-syn-(benzyloxy)-2-exo-(trimethylsilylethoxycarbonyl)-amino-3-endo-(l)-menthyl-5-exo-methyl-6-exo-methyl tricarboxylate (S4-32)

S4-31, dry copper(II) chloride, 10% Pd/C, and dry methanol are added to a flask with vigorous stirring. After degassing, the flask is charged with carbon monoxide to a pressure just above 1 atm., which is maintained for 72 hours. The solids are filtered and the residue worked up in the usual way to afford the biscarbonylation product.

Example 23

Bicyclo[2.2.1]heptane-7-syn(benzyloxy)-2-exo-(trimethylsilylethoxycarbonyl)-amino-3-endo-(l)-menthylcarbox-5-exo-6-exodicarboxylic anhydride (S4-33)

A mixture of S4-32, formic acid, and a catalytic amount of p-toluenesulfonic acid is stirred at 90° C. overnight. Acetic anhydride is added and the reaction mixture refluxed for 6 hours. Removal of the solvents and washing with ether gives the desired anhydride.

Example 24

Bicyclo[2.2.1]heptane-7-syn-(benzyloxy)-2-exo-(trimethylsilylethoxyearbonyl)-amino-3-endo-(l)-menthyl-6-exo-carboxy-5-exo-methyl dicarboxylate (S4-33)

To a solution of S4-32 in equal amounts of toluene and carbon tetrachloride is added quinidine. The suspension is cooled to −65° C. and stirred for 1 hour. Three equivalents of methanol are slowly added over 30 minutes. The suspension is stirred at −65° C. for 4 days followed by removal of the solvents under reduced pressure. The resulting white solid is partitioned between ethyl acetate and 2M HCl. The quinine is recovered from the acid layer and S4-33 obtained from the organic layer.

Example 25

Bicyclo[2.2.1]heptane-7-syn(benzyloxy)-2-exo-(trimethylsilylethoxycarbonyl)-amino-3-endo-(l)-menthyl-6-exo-(trimethylsilylethoxycarbonyl)amino-5-exo-methyl dicarboxylate (S4-35)

To a solution of S4-34 in benzene is added triethylamine and diphenylphosphoryl azide. The solution is refluxed for 24 hours. After cooling to room temperature, 2-trimethylsilylethanol is added and the solution refluxed for 48 hours. The benzene solution is partitioned between ethyl acetate and 1 M sodium bicarbonate. The organic layers are combined, washed with 1M sodium bicarbonate, and dried over sodium sulfate. The solvent is evaporated under reduced pressure to give the crude Curtius reaction product.

Example 26 endo-Bicyclo[2.2.1]hept-5-ene-2-benzylcarboxylate-3-carboxylic acid (S5-37)

Compound S3-19 (4.00 g, 0.0244 mol) and quinidine (8.63 g, 0.0266 mol) were suspended in equal amounts of toluene (50 mL) and carbon tetrachloride (50 mL). The suspension was cooled to −55° C. after which benzyl alcohol (7.90 g, 0.0732 mol) was added over 15 minutes. The reaction mixture became homogenous after 3 hours and was stirred at −55° C. for an additional 96 hours. After removal of the solvents, the residue was partitioned between ethyl acetate (300 mL) and 2M hydrochloric acid (100 mL). The organic layer was washed with water (2×50 mL) and saturated aqueous sodium chloride (1×50 mL). Drying over magnesium sulfate and evaporation of the solvent gave S5-37 (4.17 g, 0.0153 mol, 63% yield).
$^1$H NMR: (CDCl$_3$) δ 1.33 (d, 1H, bridge CH$_2$), 1.48 (d of t, 1H, bridge CH$_2$), 3.18 (bs, 1H, bridgehead CH), 3.21 (bs, 1H, bridgehead CH), 3.33 (t, 2H, α-acid CH), 4.98 (d of d, 2H, CH$_2$Ph), 6.22 (d of d, 1H, CH=CH), 6.29 (d of d, 1H, CH=CH), 7.30 (m, 5H, C$_6$H$_5$).

Example 27

2-endo-Benzylcarboxy-6-exo-iodobicyclo[2.2.1]heptane-3,5-carbolactone (S5-38)

S5-37 (4.10 g, 0.0151 mol) was dissolved in 0.5 M sodium bicarbonate solution (120 mL) and cooled to 0° C. Potassium iodide (15.0 g, 0.090 mol) and iodine (7.66 g, 0.030 mol) were added followed by methylene chloride (40 mL). The solution was stirred at room temperature overnight. After dilution with methylene chloride (100 mL), sodium thiosulfate was added to quench the excess iodine. The organic layer was separated and washed with water (100 mL) and sodium chloride solution (100 mL). Drying over magnesium sulfate and evaporation of the solvent gave S5-38 (5.44 g, 0.0137 mol, 91% yield).

$^1$H NMR: (CDCl$_3$) δ 1.86 (d of q, 1H, bridge —CH$_2$—), 2.47 (d of t, 1H, bridge —CH$_2$—), 2.83 (d of d, 1H, α-lactone carbonyl CH), 2.93 (bs, 1H, lactone bridgehead CH), 3.12 (d of d, 1H, α-benzyl ester CH), 3.29 (m, 1H, bridgehead CH), 4.63 (d, 1H, α-lactone ester CH), 5.14 (d of d, 2H, CH$_2$Ph), 5.19 (d, 1H, iodo CH), 7.38 (m, 5H, C$_6$H$_5$).

Example 28

2-endo-Benzylcarboxy-bicyclo[2.2.1]heptane-3,5-carbolactone (S5-39)

S5-38 (0.30 g, 0.75 mmol) was placed in DMSO under N$_2$, NaBH$_4$ (85 mg, 2.25 mmol) added and the solution stirred at 85° C. for 2 h. The mixture was cooled, diluted with water (50 mL) and extracted with dichloromethane (3×20 mL). The extracts were combined, washed with water (4×15 mL) and saturated aqueous NaCl (10 mL), dried, and evaporated to give 0.14 g (68%) of S5-39.

Example 29

5-endo-hydroxybicyclo[2.2.1]heptane-2-endo-benzyl-3-endo-methyl dicarboxylate (S5-40)

Compound S5-39 is dissolved in methanol and sodium methoxide added with stirring. Removal of the solvent gives S5-40.

Example 30

Bicyclo[2.2.1]heptane-2-endo-benzyl-3-endo-methyl-5-exo-(t-butoxycarbonyl)-amino dicarboxylate (S5-41)

In a one-pot reaction S5-40 is converted to the corresponding mesylate with methanesulfonyl chloride, sodium azide added to displace the mesylate to give exo-azide, which is followed by reduction with tributyl phosphine to give the free amine, which is protected as the t-Boc derivative to give S5-41.

Example 31

Bicyclo[2.2.1]heptane-2-endo-carboxy-3-exo-methyl-5-exo-(t-butoxycarbonyl)-amino carboxylate (S5-42)

The benzyl ether protecting group is removed by catalytic hydrogenolysis of S5-41 with 10% Pd/C in methanol at room temperature for 6 hours. Filtration of the catalyst and removal of the solvent yields crude S5-42.

Example 32

Bicyclo[2.2.1]heptane-2-endo-carboxy-3-exo-methyl-5-exo-(t-butoxycarbonyl)-amino carboxylate (S5-43)

Sodium is dissolved in methanol to generate sodium methoxide. S5-42 is added and the mixture stirred at 62° C. for 16 hr. The mixture is cooled and acetic acid added with cooling to neutralize the excess sodium methoxide. The mixture is diluted with water and extracted with ethyl acetate. The extract is dried and evaporated to give S5-43.

Example 33

Bicyclo[2.2.1]heptane-2-endo-benzyl-3-exo-methyl-5-exo-(t-butoxycarbonyl)amino dicarboxylate (S5-44)

Compound S5-43 is reacted with benzyl bromide and cesium carbonate in tetrahydrofuran at room temperature to give benzyl ester S5-44, which is isolated by acid work-up of the crude reaction mixture.

Example 34

Bicyclo[2.2.1]heptane-2-endo-benzyl-3-exo-carboxy-5-exo-(t-butoxycarbonyl)-amino carboxylate (S5-45)

Compound S5-44 is dissolved in methanol and cooled to 0° C. under N$_2$. 2M NaOH (2 equivalents) is added dropwise, the mixture allowed to come to ambient temperature and is stirred for 5 h. The solution is diluted with water, acidified with 2M HCl and extracted with ethyl acetate. The extract is washed with water, saturated aqueous NaCl, dried and evaporated to give S5-45.

Example 35

Bicyclo[2.2.1]heptane-2-endo-benzyl-3-exo-(trimethylsilylethoxycarbonyl)amino-5-exo-(t-butoxycarbonyl)amino carboxylate (S5-46)

To a solution of S5-45 in benzene is added triethylamine and diphenylphosphoryl azide. The solution is refluxed for 24 hours and then cooled to room temperature. Trimethylsilylethanol is added and the solution refluxed for 48 hours. The solution is partitioned between ethyl acetate and 1 M sodium bicarbonate. The organic layer is washed with 1 M sodium bicarbonate and dried over sodium sulfate. The solvent is evaporated under reduced pressure to give crude Curtius product S5-46.

Example 36 endo-Bicyclo[2.2.1]hept-5-ene-2-(4-methoxy)benzylcarboxylate-3-carboxylic acid (S6-48)

Compound S3-19 and quinidine are suspended in equal amounts of toluene and carbon tetrachloride and cooled to −55° C. p-Methoxybenzyl alcohol is added over 15 minutes and the solution stirred at −55° C. for 96 hours. After removal of the solvents, the residue is partitioned between ethyl acetate and 2 M hydrochloric acid. The organic layer is washed with water and saturated aqueous sodium chloride. Drying over magnesium sulfate and removal of the solvent gives S6-48.

Example 37 endo-Bicyclo[2.2.1]hept-5-ene-2-(4-methoxy)benzyl-3-(trimethylsilylethoxy-carbonyl)amino carboxylate (S6-49)

To a solution of S6-48 in benzene is added triethylamine and diphenylphosphoryl azide. The solution is refluxed for 24 hours, cooled to room temperature, trimethylsilylethanol is added, and the solution is refluxed for an additional 48 hours. The benzene solution is partitioned between ethyl acetate and 1 M sodium bicarbonate. The organic layers are combined, washed with 1 M sodium bicarbonate, and dried with sodium sulfate. The solvent is evaporated under reduced pressure to give crude Curtius product S6-49.

Example 38

Bicyclo[2.2.1]heptane-2-endo-(4-methoxy)benzyl-3-endo-(trimethylsilylethoxycarbonyl)amino-5-exo-methyl-6-exo-methyl tricarboxylate (S6-50)

S6-49, copper(II) chloride, 10% Pd/C, and dry methanol are added to a flask with vigorous stirring. After degassing the suspension, the flask is charged with carbon monoxide to a pressure just above 1 atm. The pressure of carbon monoxide is maintained over 72 hours. The solids are filtered off, and the crude reaction mixture worked up in the usual way to afford S6-50.

Example 39

Bicyclo[2.2.1]heptane-2-endo-(4-methoxy)benzyl-3-endo-(trimethylsilylethoxycarbonyl)amino-5-exo-6-exo-dicarboxylic anhydride (S6-51)

S6-50, formic acid, and a catalytic amount of p-toluenesulfonic acid is heated at 90° C. overnight. Acetic anhydride is added to the reaction mixture, and it is refluxed for an additional 6 hours. Removal of the solvents and washing with ether affords S6-51.

Example 40

Bicyclo[2.2.1]heptane-2-endo-(4-methoxy)benzyl-3-endo-(trimethylsilylethoxycarbonyl)amino-5-exo-carboxy-6-exo-methyl dicarboxylate (S6-52)

To a solution of S6-51 in equal amounts of toluene and carbon tetrachloride is added quinine. The suspension is cooled to −65° C. and stirred for 1 hour. Three equivalents of methanol are added slowly over 30 minutes. The suspension is stirred at −65° C. for 4 days followed by removal of the solvents. The resulting white solid is partitioned between ethyl acetate and 2 M HCl, with S6-52 worked up from the organic layer.

Example 41

Bicyclo[2.2.1]heptane-2-endo-(4-methoxy)benzyl-3-endo-(trimethylsilyiethoxycarbonyl)amino-5-exo-(trimethylsilylethoxycarbonyl)amino-6-exo-methyl dicarboxylate (S6-53)

To a solution of S6-52 in benzene is added triethylamine and diphenylphosphoryl azide. The solution is refluxed for 24 hours then cooled to room temperature. 2-Trimethylsilylethanol is added, and the solution is refluxed for an additional 48 hours. The benzene solution is partitioned between ethyl acetate and 1 M sodium bicarbonate. The organic layers are combined, washed with 1 M sodium bicarbonate, and dried with sodium sulfate. The solvent is evaporated under reduced pressure to give S6-53.

Example 42

Bicyclo[2.2.1]heptane-2-exo-(4-methoxy)benzyl-3-endo-(trimethylsilylethoxycarbonyl)amino-5-exo-(trimethylsilylethoxycarbonyl)amino-6-endo-methyl dicarboxylate (S6-54)

To a solution of S6-53 in tetrahydrofuran is carefully added potassium tert-butoxide. The basic solution is refluxed for 24 hours followed by addition of acetic acid. Standard extraction methods give the double epimerized product S6-54.

Example 43

Preparation of Hexamer

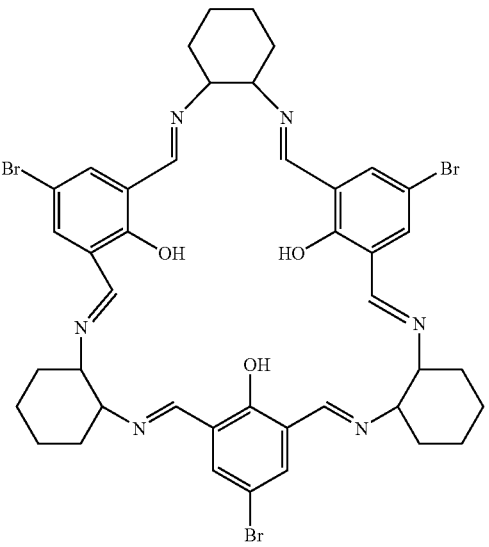

Hexamer 1a-Br

To 0.300 g (1R,2R)-(−)-trans-1,2-diaminocyclohexane (2.63 mmol) in 5 mL $CH_2Cl_2$ at 0° C. was added 0.600 g of 2,6-diformyl-4-bromophenol (2.62 mmol) in 5 mL of $CH_2Cl_2$. The yellow solution was allowed to warm to room temperature and stirred for 48 hours. The reaction solution was decanted, and added to 150 mL of methanol. After standing for 30 minutes, the yellow precipitate was collected, washed with methanol, and air-dried (0.580 g; 72% yield).

$^1$H NMR (400 MHz, $CDCl_3$) δ 14.31 (s, 3H, OH), 8.58 (s, 3H, CH=N), 8.19 (s, 3 H, CH=N), 7.88 (d, 3H, J=2.0 Hz, ArH), 7.27 (d, 3H, J=2.0 Hz, ArH), 3.30-3.42 (m, 6 H, $CH_2$—CH—N), 1.41-1.90 (m, 24 H, aliphatic).

MS (FAB): Calcd for $C_{42}H_{46}N_6O_3Br_3$ 923.115; found 923.3 [M+H]$^+$.

Example 44

Preparation of Hexamer

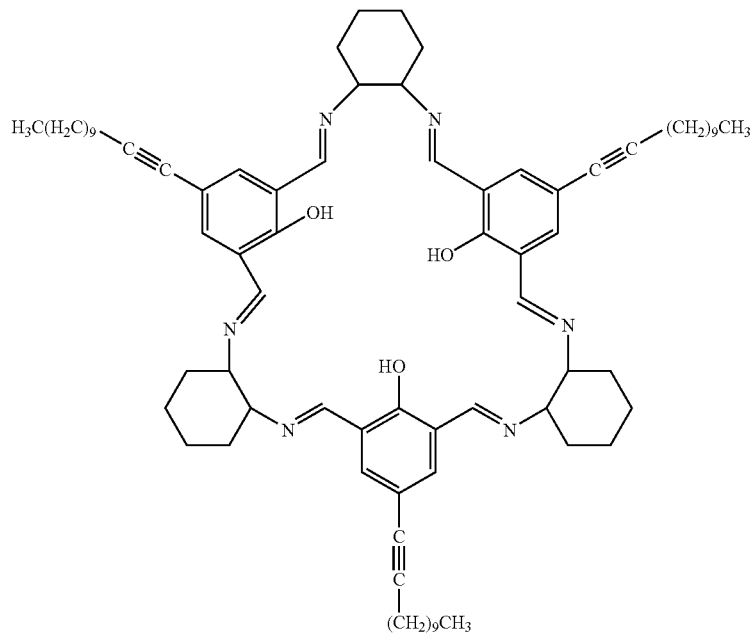

Hexamer 1a

To 0.300 g (1R,2R)-(−)-trans-1,2-diaminocyclohexane (2.63 mmol) in 6 mL $CH_2Cl_2$ at 0° C. was added 0.826 g of 2,6-diformyl-4-(1-dodec-1-yne)phenol (2.63 mmol) in 6 mL of $CH_2Cl_2$. The orange solution was stirred at 0° C. for 1 hour and then allowed to warm to room temperature after which stirring was continued for 16 hours. The reaction solution was decanted and added to 150 mL of methanol. A sticky yellow solid was obtained after decanting the methanol solution. Chromatographic cleanup of the residue gave a yellow powder.

$^1$H NMR (400 MHz, $CDCl_3$) δ 14.32 (s, 3H, OH), 8.62 (s, 3H, CH=N), 8.18 (s, 3 H, CH=N), 7.84 (d, 3H, J=2.0 Hz, ArH), 7.20 (d, 3H, J=2.0 Hz, ArH), 3.30-3.42 (m, 6 H, $CH_2$—CH—N), 2.25 (t, 6 H, J=7.2 Hz, propargylic), 1.20-1.83 (m, 72H, aliphatic), 0.85 (t, 9H, J=7.0 Hz, $CH_3$).

$^3$C NMR (400 MHz, $CDCl_3$) 163.4, 161.8, 155.7, 136.9, 132.7, 123.9, 119.0, 113.9, 88.7, 79.7, 75.5, 73.2, 33.6, 33.3, 32.2, 29.8, 29.7, 29.6, 29.4, 29.2, 29.1, 24.6, 24.5, 22.9, 19.6, 14.4.

MS (FAB): Calcd for $C_{78}H_{109}N_6O_3$ 1177.856; found: 1177.8 $[M+H]^+$.

Example 45

Preparation of Hexamer

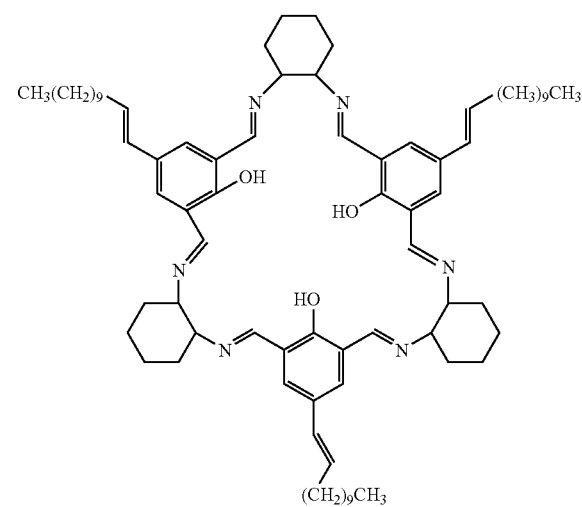

Hexamer 1d-C12

To 0.240 g of 2,6-diformyl-4-(1-dodecene)phenol (0.76 mmol) in 10 ml of benzene was added a 10 mL benzene solution of (1R,2R)-(−)-trans-1,2-diaminocyclohexane (0.087 g, 0.76 mmol). The solution was stirred at room temperature for 48 hours shielded from the light. The orange solution was taken to dryness and chromatographed (silica, 50/50 acetone/Et$_2$O) to give a yellow sticky solid (33% yield).

$^1$H NMR (400 MHz, CDCl$_3$) δ 14.12 (s, 3H, OH), 8.62 (s, 3H, CH=N), 8.40 (s, 3 H, CH=N), 7.82 (d, 3H, J=2.0 Hz, ArH), 7.28 (d, 3H, J=2.0 Hz, ArH), 6.22 (d, 3H, vinyl), 6.05 (d, 3H, vinyl), 3.30-3.42 (m, 6 H, CH$_2$—CH—N), 1.04-1.98 (m, 87 H, aliphatic).

MS (FAB): Calcd for C$_{78}$H$_{115}$N$_6$O$_3$ 1183.90; found: 1184.6 [M+H]$^+$.

Example 46

Preparation of Tetramer

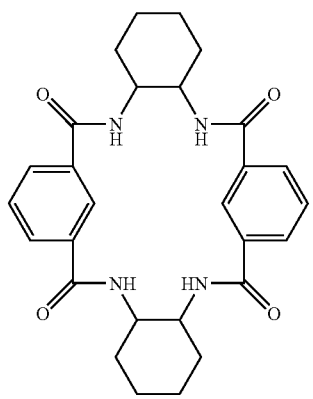

Tetramer 2-phenyl

Preparation of Hexamer:

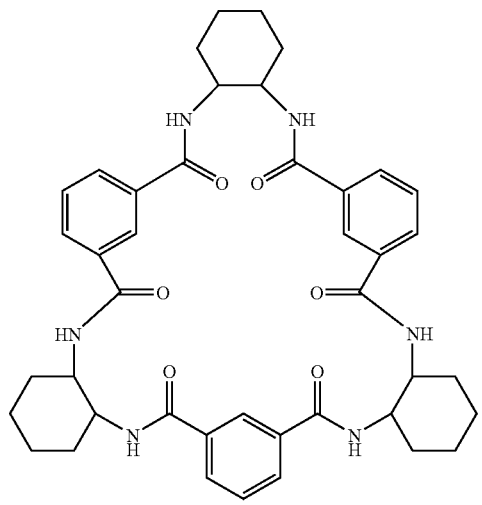

Hexamer 6-phenyl

Triethylamine (0.50 mL, 3.59 mmol) and (1R,2R)-(−)-trans-1,2-diaminocyclohexane (0.190 g, 1.66 mmol) were combined in 150 mL EtOAc and purged with N$_2$ for 5 minutes. To this solution was added 0.331 g isophthaloyl chloride (1.66 mmol) dissolved in 100 ml EtOAc dropwise over six hours. The solution was filtered and the filtrate taken to dryness. TLC (5% methanol/CH$_2$Cl$_2$) shows the product mixture to be primarily composed of two macrocyclic compositions. Chromatographic separation (silica, 5% methanol/CH$_2$Cl$_2$) gave The above tetramer (0.020 g, 5% yield) and hexamer (about 10%).

Tetramer:

$^1$H NMR (400 MHz, CDCl$_3$) δ 7.82 (s, 1H), 7.60 (br s, 2 H), 7.45 (br s, 2 H), 7.18 (br s, 1H), 390 (br s, 2 H), 2.22 (d, 2H), 1.85 (m, 4 H), 1.41 (m, 4 H).

MS (ESI): Calcd for C$_{28}$H$_{33}$N$_4$O$_4$ 489.25; found 489.4 [M+H]$^+$.

Hexamer:

MS (ESI): Calcd for C$_{42}$H$_{49}$N$_6$O$_6$ 733.37; found 733.5 [M+H]$^+$.

Example 47

Preparation of Macrocyclic Modules from Benzene and Cyclohexane Cyclic Synthons

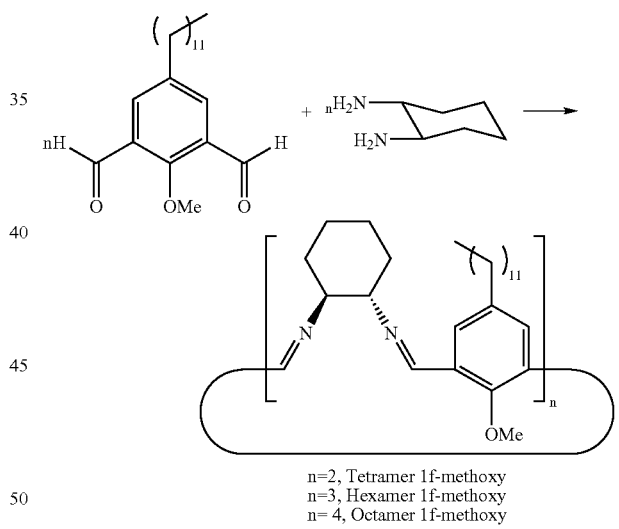

n=2, Tetramer 1f-methoxy
n=3, Hexamer 1f-methoxy
n=4, Octamer 1f-methoxy

To a 5 mL dichloromethane solution of 4-dodecyl-2,6-diformyl anisole (24 mg; 0.072 mmol) was added a 5 mL dichloromethane solution of (1R,2R)-(−)-trans-1,2-diaminocyclohexane (8.5 mg; 0.074 mmol). This solution was stirred at room temperature for 16 hours and then added to the top of a short silica column. Elution with diethyl ether and then removal of solvent led to the isolation of 22 mg of an off-white solid. Positive ion electrospray mass spectrometry demonstrated the presence of the tetramer (m/z 822, MH$^+$), hexamer (m/z 1232, MH+), and the octamer (m/z 1643, MH$^+$) in the off-white solid. Calculated molecular weights were as follows: tetramer+H (C$_{54}$H$_{85}$N$_4$O$_2$, 821.67); hexamer+H (C$_{81}$H$_{127}$N$_6$O$_3$, 1232.00); octamer+H (C$_{108}$H$_{169}$N$_8$O$_4$, 1643.33).

Example 48

Without intending to be bound by any one particular theory, one method to approximate pore size of a macrocyclic module is quantum mechanical (QM) and molecular mechanical (MM) computations. In this example, macrocyclic modules having two types of synthons, "A" and "B," were used and all linkages between synthons were assumed to be the same. For the purposes of QM and MM computations, the root mean square deviations in the pore areas were computed over dynamic runs.

For QM, each module was first optimized using the MM+ force field approach of Allinger (JACS, 1977, 99:8127) and Burkert, et al., (Molecular Mechanics, ACS Monograph 177, 1982). They were then re-optimized using the AM1 Hamiltonian (Dewar, et al., JACS, 1985, 107:3903; Dewar, et al., JACS, 1986, 108:8075; Stewart, J. Comp. Aided Mol. Design, 1990, 4:1). To verify the nature of the potential energy surface in the vicinity of the optimized structures, the associated Hessian matrices were computed using numerical double-differencing.

For MM, the OPLS-AA force field approach (Jorgensen, et al., JACS, 1996, 118:11225) was used. For imine linkages, the dihedral angle was confined to 180°±10°. The structures were minimized and equilibrated for one picosecond using 0.5 femtosecond time steps. Then a 5 nanosecond dynamics run was carried out with a 1.5 femtosecond time step. Structures were saved every picosecond. The results are shown in Tables 4 and 5.

Macrocyclic module pore areas derived from QM and MM computations for various linkages and macrocyclic module pore size are shown in Table 4. In Table 4, the macrocyclic modules had alternating synthons "A" and "B." Synthon "A" is a benzene synthon coupled to linkages L at 1,3-phenyl positions, and Synthon "B" is shown in the left-hand column of the table.

TABLE 4

| | Pore areas for various macrocyclic modules ($Å^2$) | | | | | |
|---|---|---|---|---|---|---|
| SYNTHON B | TETRAMER QM | TETRAMER MM | HEXAMER QM | HEXAMER MM | OCTAMER QM | OCTAMER MM |
| trans-1,2-cyclohexane | | | imine (trans) 14.3 $Å^2$ | Imine (trans) 13.2 ± 1.4 $Å^2$ | | |
| trans-1,2-cyclohexane | | | Acetylene 14.3 $Å^2$ | | | |
| trans-1,2-cyclohexane | | | Amine 23.1 $Å^2$ | Amine 13.9 ± 1.9 $Å^2$ | | |
| trans-1,2-cyclohexane | | | Amide 19.7 $Å^2$ | Amide 17.5 ± 2.0 $Å^2$ | | |
| trans-1,2-cyclohexane | | | Ester 18.9 $Å^2$ | Ester 19.6 ± 2.0 $Å^2$ | | |
| Equatorial-1,3-cyclohexane | | | imine (trans) 18.1 $Å^2$ | Imine (trans) 21.8 ± 1.6 $Å^2$ | imine (trans) 66.2 $Å^2$ | Imine (trans) 74.5 ± 7.7 $Å^2$ |
| Equatorial-1,3-cyclohexane | | | Amine 14.7 $Å^2$ | Amine 19.9 ± 2.6 $Å^2$ | | |
| Equatorial-1,3-cyclohexane | | | Amide 24.8 $Å^2$ | Amide 21.7 ± 1.8 $Å^2$ | | |
| Equatorial-1,3-cyclohexane | | | Ester 22.9 $Å^2$ | Ester 22.8 ± 2.4 $Å^2$ | | |
| Equatorial-3-amino-cyclohexene | imine (trans) oxygen-oxygen distance 2.481 Å | imine (trans) oxygen-oxygen distance 3.7 ± .3 Å | imine (trans) 18.4 $Å^2$ | Imine (trans) 21.0 ± 1.5 $Å^2$ | imine (trans) 56.7 $Å^2$ | Imine (trans) 60.5⁺ – 8.3 $Å^2$ |
| trans-1,2-pyrrolidine | | | imine (trans) 10.4 $Å^2$ | Imine (trans) 9.2 ± 1.4 $Å^2$ | | |
| Equatorial-1,3-piperidene | | | imine (trans) 19.2 $Å^2$ | Imine (trans) 20.9 ± 1.1 $Å^2$ | | |

TABLE 4-continued

Pore areas for various macrocyclic modules (Å²)

| SYNTHON B | TETRAMER QM | TETRAMER MM | HEXAMER QM | HEXAMER MM | OCTAMER QM | OCTAMER MM |
|---|---|---|---|---|---|---|
| Endo-exo-1,2-bicycloheptane | | | imine (trans) 11.1 Å² | Imine (trans) 14.1 ± +−11 Å² | | |
| Endo-endo-1,3-bicycloheptane | | | imine (trans) 18.8 Å² | Imine (trans) 20.7 ± 1.4 Å² | | |
| Endo-exo-1,3-bicycloheptane | | | Imine 19.5 Å² | Imine 10.1 ± +4.9 Å² | | |
| Equatorial-1,3-cyclohexane | | | Amine 9.8 Å² | Amine 9.9 ± 2.4 Å² | | |
| Endo-endo-1,3-bicyclooctene | | | imine (trans) 18.9 Å² | Imine (trans) 21.6 ± 1.5 Å² | | |
| Endo-exo-1,3-bicyclooctene | | | imine (trans) 15.6 Å² | Imine (trans) 18.7 ± 1.6 Å² | | |
| Equatorial-3,9-decalin | | | imine (trans) 35.4 Å² | Imine (trans) 40.0 ± 2.2 Å² | | |

Further macrocyclic module pore areas derived from QM and MM computations for various linkages and macrocyclic module pore size are shown in Table 5. In Table 5, the macrocyclic modules had alternating synthons "A" and "B." In Table 5, Synthon "A" is a naphthalene synthon coupled to linkages L at 2,7-naphthyl positions, and Synthon "B" is shown in the left-hand column of the table.

TABLE 5

Pore areas for various macrocyclic modules (Å²)

| SYNTHON B | HEXAMER QM | HEXAMER MM |
|---|---|---|
| Trans-1,2-cyclohexane | imine (trans) 23.5 Å² | imine (trans) 25.4 ± 4.9 Å² |
| Endo-endo-1,3-bicycloheptane | imine (trans) 30.1 Å² | imine (trans) 30.0 ± 3.6 Å² |

Figure 1B:
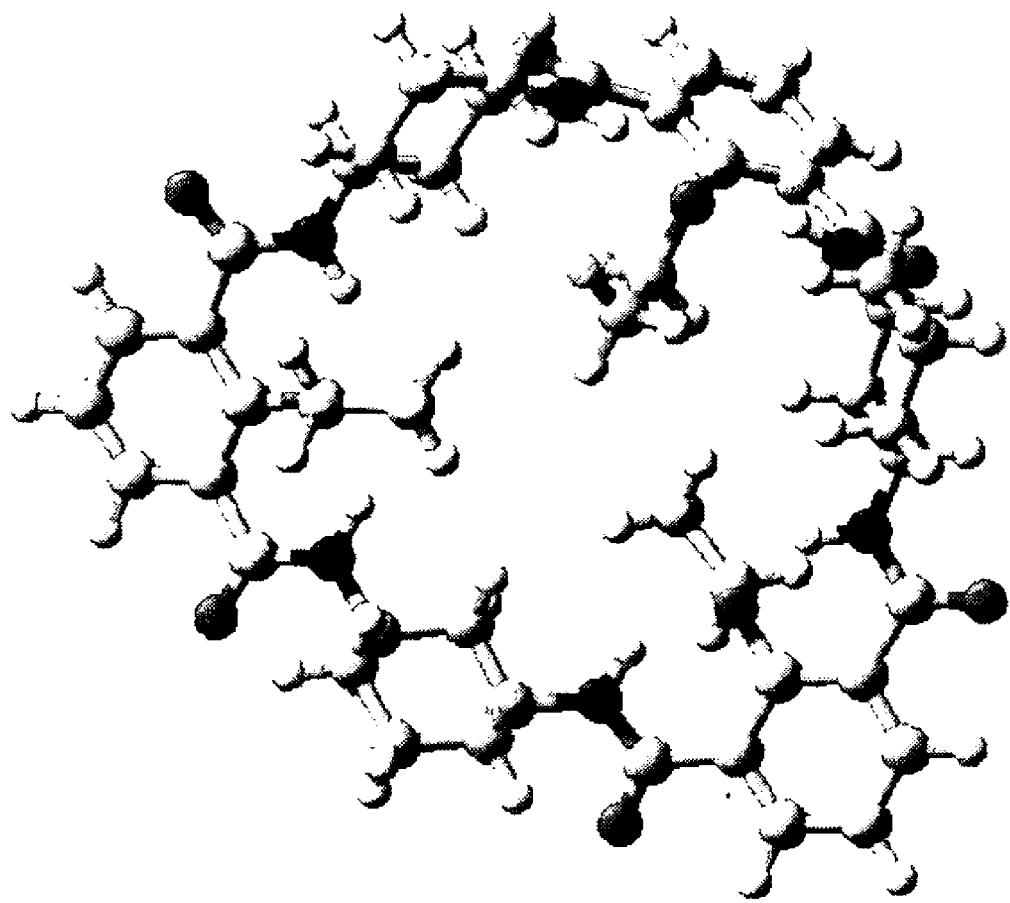
FIG. 1B shows a representation of an example of the structure of an embodiment of a hexamer macrocyclic module.

An example of the energy-minimized conformations of some hexamer macrocyclic modules having groups of substituents are shown in FIGS. 1A and 1B. Referring to FIG. 1A, a Hexamer 1-h-(OH)₃ is shown having a group of —OH substituents. Referring to FIG. 1B, a Hexamer 1-h-(OEt)₃ is shown having a group of —OEt substituents. The differences in pore structure and area between these two examples, which also reflect conformational and flexibility differences, are evident. This macrocyclic module results in a composition which may be used to regulate pores. Selection of ethoxy synthon substituents over hydroxy synthon substituents for this hexamer composition is a method which may be used for transporting selected species.

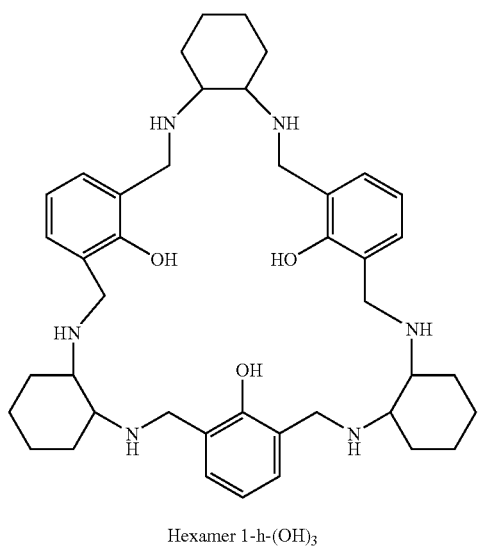

Hexamer 1-h-(OH)₃

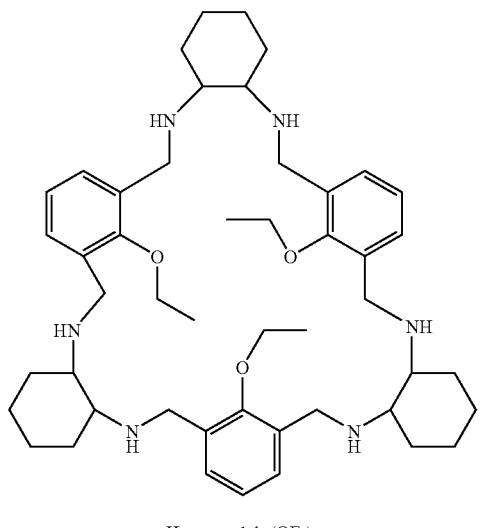

Hexamer 1-h-(OEt)₃

The pore size of macrocyclic modules was determined experimentally using a voltage-clamped bilayer procedure. A quantity of a macrocyclic module was inserted into a lipid bilayer formed by phosphatidylcholine and phosphatidylethanolamine. On one side of the bilayer was placed a solution containing the cationic species to be tested. On the other side was a solution containing a reference cationic species known to be able to pass through the pore of the macrocyclic module. Anions required for charge balance were selected which could not pass through the pores of the macrocyclic module. When a positive electrical potential was applied to the solution on the side of the lipid bilayer containing the test species, if the test species passed through the pores in the macrocyclic modules, a current was detected. The voltage was then reversed to detect current due to transport of the reference species through the pores, thereby confirming that the bilayer is a barrier to transport and that the pores of the macrocyclic modules provide transport of species.

Using the above technique, a hexameric macrocyclic module comprised of 1R,2R-(−)-transdiaminocyclohexane and 2,6-diformal-4-(1-dodec-1-ynyl)phenol synthons, having imine groups as the linkages (the first module in Table 3) was tested for transport of various ionic species. The results are shown in Table 6.

TABLE 6

Voltage-clamped bilayer test for macrocyclic module pore size

| Ionic species | Calculated van der Waals radius of ionic species (Å) | Calculated van der Waals radius of ionic species with one water shell (Å) | Does ionic species pass through pore? |
|---|---|---|---|
| $Na^+$ | 1.0 | 2.2 | Yes |
| $K^+$ | 1.3 | 2.7 | Yes |
| $Ca^{2+}$ | 1.0 | 2.7 | Yes |
| $NH_4^+$ | 1.9 | 2.9 | Yes |
| $Cs^+$ | 1.7 | 3.0 | Yes |
| $MeNH_3^+$ | 2.0 | 3.0 | Yes |
| $EtNH_3^+$ | 2.6 | 3.6 | No |
| $NMe_4^+$ | 2.6 | 3.6 | No |
| Aminoguanidinium | 3.1 | 4.1 | No |
| $NEt_4^+$ | 3.9 | 4.4 | No |
| Choline | 3.8 | 4.8 | No |
| Glucosamine | 4.2 | 5.2 | No |

The results in Table 6 show that the cut-off for passage through the pore in the selected module is a van der Waals radius of between 2.0 and 2.6 Å. In Table 4, the QM and MM computed pore sizes are given as areas. Using the equation for area of a circle, $A=\pi r^2$, the computed area of the pore in the first module of Table 4, 14.3 Å$^2$, gives a value for r of 2.13 Å. Ions having van der Waals radii of less than 2.13 Å would be expected to traverse the pore and those with larger radii would not, and that is what was observed. $CH_3NH_3^+$, having a radius of 2.0 Å, passed through the pore while $CH_3CH_2NH_3^+$, with a radius of 2.6 Å, did not. Without being held to a particular theory, and recognizing that several factors influence pore transport, the observed ability of hydrated ions to pass through the pore may be due to partial dehydration of the species to enter the pore, transport of water molecules and ions through the pore separately or with reduced interaction during transport, and re-coordination of water molecules and ions after transport. The details of pore structure, composition, and chemistry, the flexibility of the macrocyclic module, and other interactions may affect the transport process.

Example 49

Pore properties of 1,2-imine-linked and 1,2-amine-linked hexamer macrocyclic modules are illustrated in Table 7. Referring to Table 7, the bilayer clamp data indicates that the passage and exclusion of certain species through the pore of the modules correlates with the computational size of the pores. Further, these surprising data show that a very small change in the placement of atoms and/or structural features can lead to a discrete change in transport properties and allow regulation of transport through the pore by variation of synthons and linkages, among other factors.

TABLE 7

Voltage-clamped bilayer test for macrocyclic module pore size

| Solute species | Radius of Solute | Radius of solute with $H_2O$ (radius of $2^{nd}$ hydration shell in parentheses) | Hexamer 1a (1,2-imine) Radius = 3.3 Å | Hexamer 1jh (1,2-amine) Radius = 3.9 Å |
|---|---|---|---|---|
| $Li^+$ | 0.6 | 2.0 (5.6) | No | Yes |
| $Na^+$ | 1.0 | 2.2 | Yes | Yes |
| $K^+$ | 1.3 | 2.7 | Yes | Yes |
| $Ca^{2+}$ | 1.0 | 2.7 | Yes | Yes |
| $Mg^{2+}$ | 0.7 | 2.8 (5.5) | No | Yes |
| $NH_3^+$ | 1.9 | 2.9 | Yes | Yes |
| $Cs^+$ | 1.7 | 3 | Yes | Yes |
| $MeNH_3^+$ | 2 | 3 | Yes | Yes |

TABLE 7-continued

Voltage-clamped bilayer test for macrocyclic module pore size

| Solute species | Radius of Solute | Radius of solute with H$_2$O (radius of 2$^{nd}$ hydration shell in parentheses) | Hexamer 1a (1,2-imine) Radius = 3.3 Å | Hexamer 1jh (1,2-amine) Radius = 3.9 Å |
|---|---|---|---|---|
| EtNH$_3^+$ | 2.6 | 3.6 | No | Yes |
| NMe$_4^+$ | 2.6 | 3.6 | No | Yes |
| Aminoguanidine | 3.1 | 4.1 | No | Yes |
| Choline | 3.8 | 4.8 | No | Yes |
| NEt$_4^+$ | 3.9 | 4.4 | No | No |
| Glucosamine | 4.2 | 5.2 | No | No |
| NPr$_4^+$ | — | — | — | No |

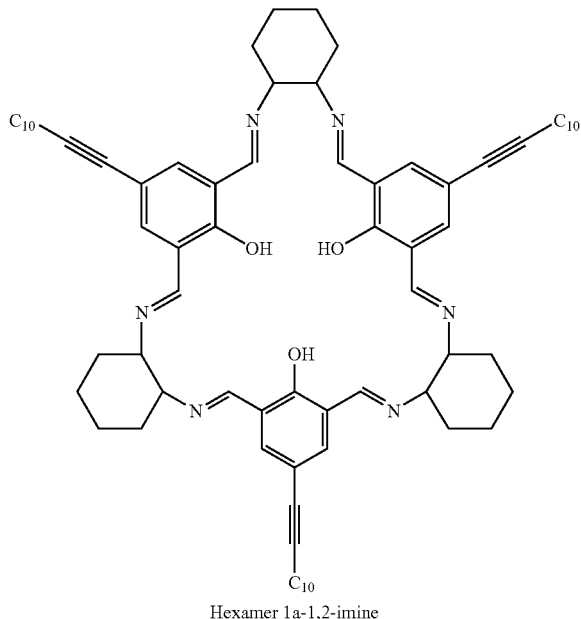

Hexamer 1a-1,2-imine

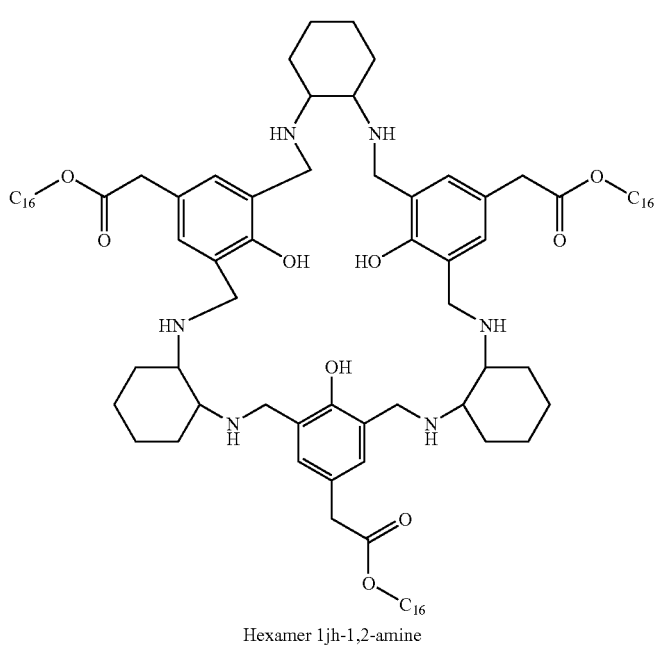

Hexamer 1jh-1,2-amine

Example 50

Figure 2A:
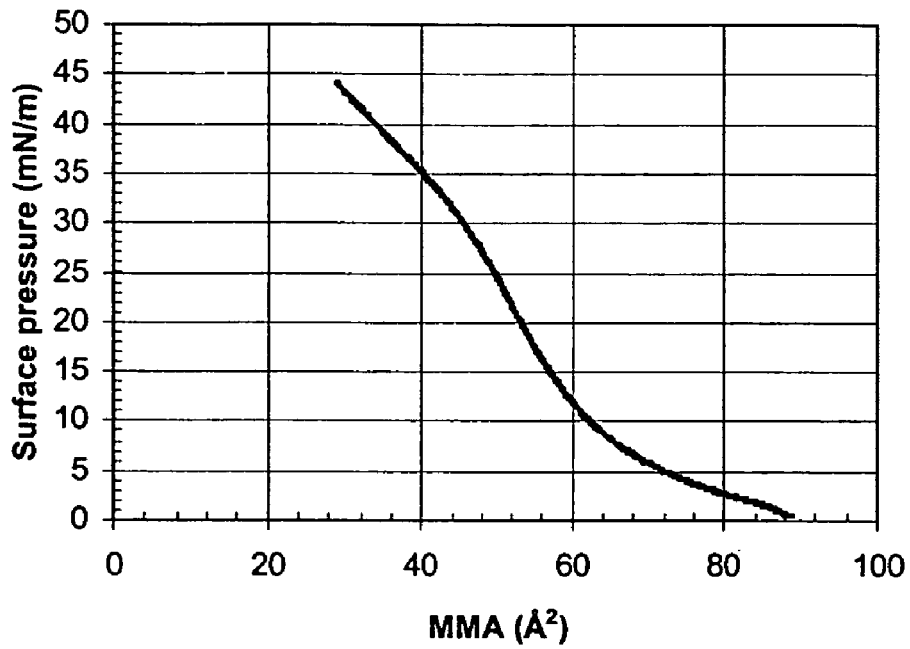
FIG. 2A shows an example of the Langmuir isotherm of an embodiment of a hexamer became macrocyclic module.
Figure 2B:
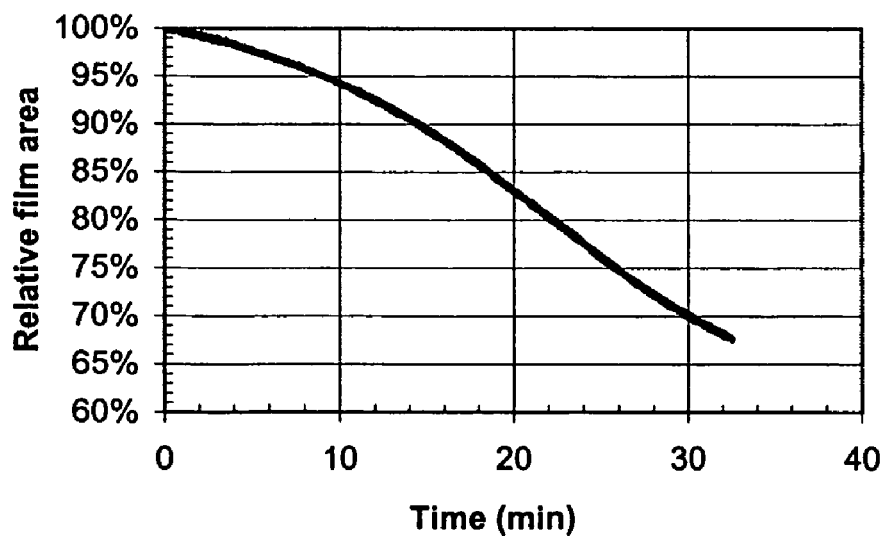
FIG. 2B shows an example of the isobaric creep of an embodiment of a hexamer macrocyclic module.

The Langmuir isotherm and isobaric creep for hexamer 1a-Me are shown in FIGS. 2A and 2B, respectively.

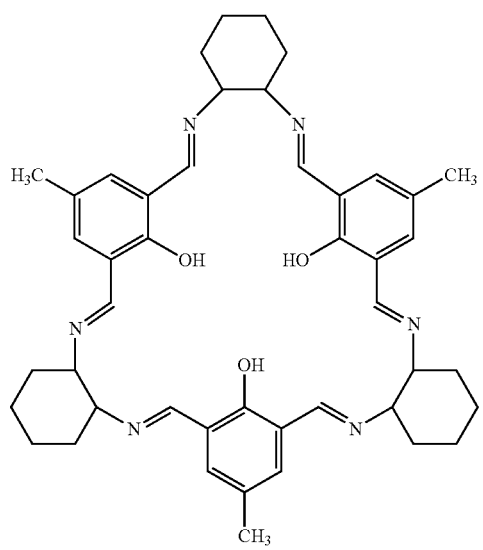

Hexamer 1a-Me

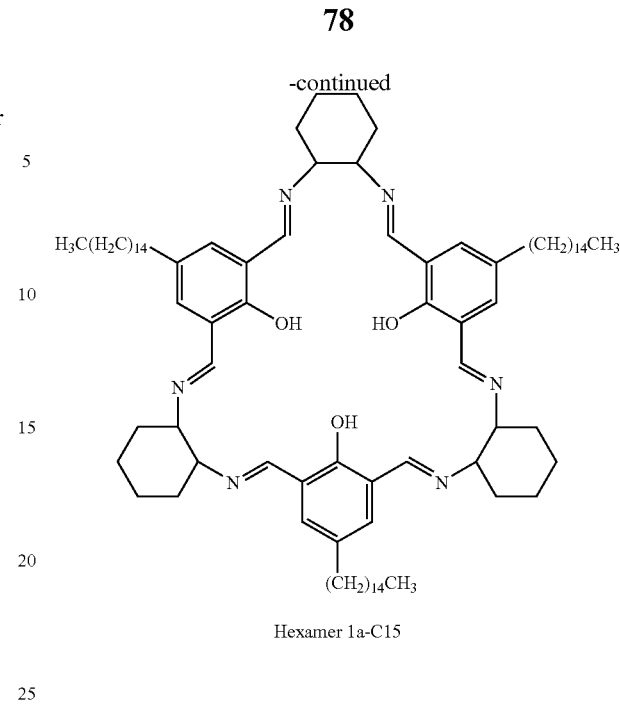

Hexamer 1a-C15

Figure 3A:
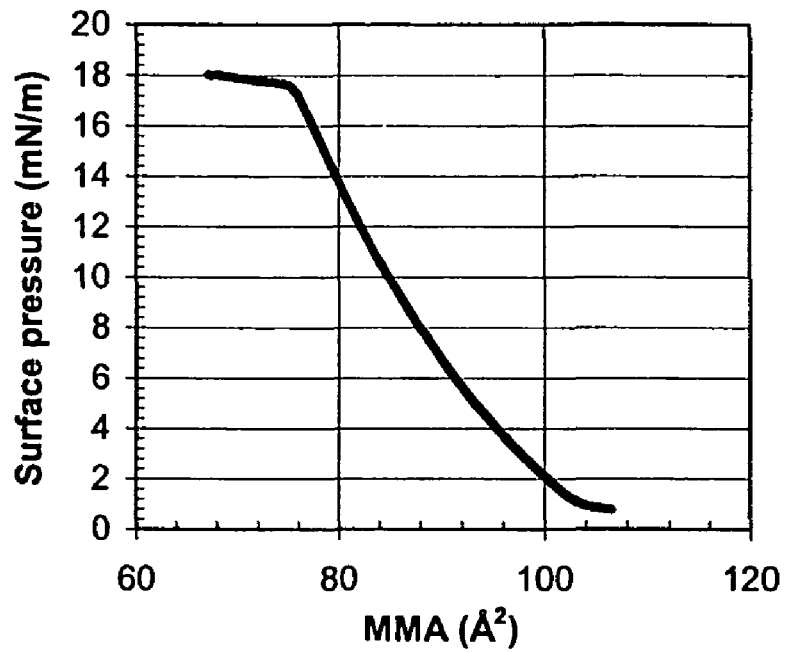
FIG. 3A shows an example of the Langmuir isotherm of an embodiment of a hexamer macrocyclic module.
Figure 3B:
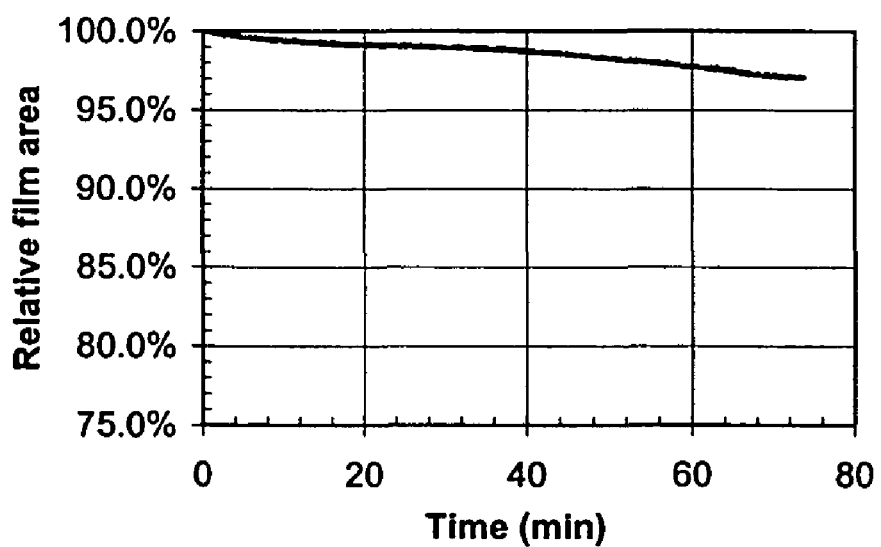
FIG. 3B shows an example of the isobaric creep of an embodiment of a hexamer macrocyclic module.

The relative stability of the Langmuir film of Hexamer 1a-Me is illustrated by the isobaric creep data shown in FIG. 2B. The area of the film decreased by about 30% after about 30 min at 5 mN/m surface pressure. The Langmuir isotherm and isobaric creep for Hexamer 1a-C15 are shown in FIGS. 3A and 3B, respectively. The relative stability of the Langmuir film of Hexamer 1a-C15 is illustrated by the isobaric creep data shown in FIG. 3B. The area of the film decreased by about 1-2% after about 30 min at 10 mN/m surface pressure, and by about 2% after about 60 min. The collapse pressure was about 18 mN/m for Hexamer 1a-C15.

Example 51

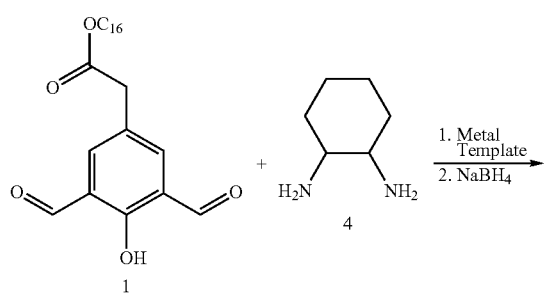

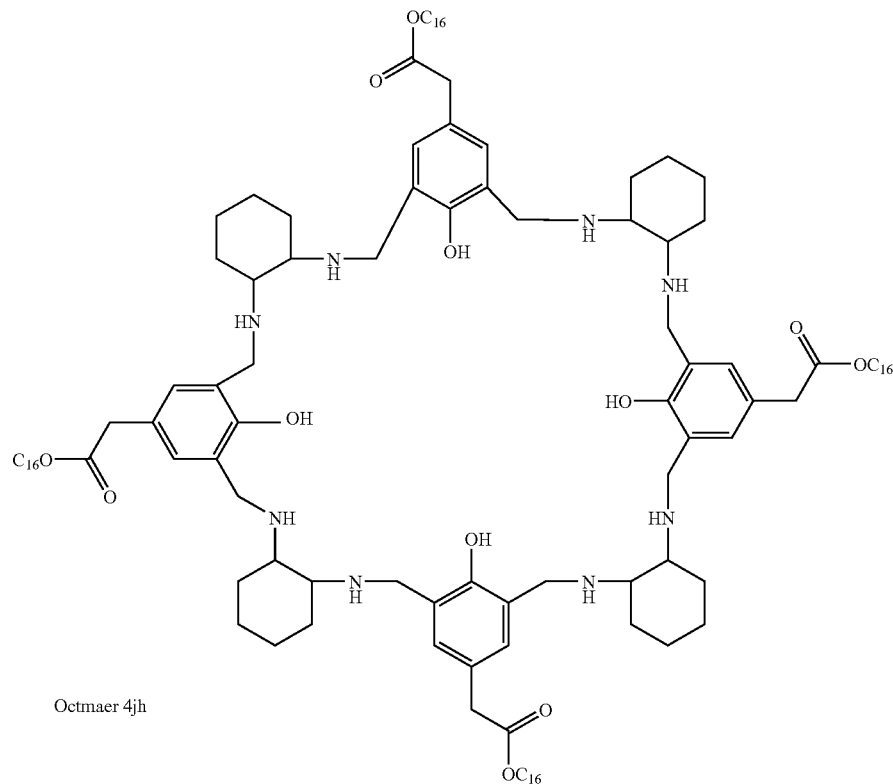

Octmaer 4jh

Templated Imine Octamer. To a 3 neck 100 mL round bottomed flask with stirbar, fitted with condenser and addition funnel under argon, amphiphilic dialdehyde phenol 1 (500 mg, 1.16 mmol) was added. Next, $Mg(NO_3)_2 \cdot 6\ H_2O$ (148 mg, 0.58 mmol) 2 and $Mg(OAc)_2 \cdot 4\ H_2O$ (124 mg, 0.58 mmol) were successively added. The flask was put under vacuo and backfilled with argon 3×. Anhydrous methanol was transferred to the flask via syringe under argon and the resulting suspension stirred. The mixture was then refluxed for 10 min affording a homogeneous solution. The reaction was allowed to cool to room temperature under positive argon pressure. (1R,2R)-(−)-trans-1,2-diaminocyclohexane 4 was added to the addition funnel followed by cannula transfer of anhydrous MeOH (11.6 mL) under argon. The diamine/MeOH solution was added to the stirred homogeneous metal template/dialdehyde solution drop wise over a period of 1 h affording an orange oil. The addition funnel was replaced with a glass stopper and the mixture was refluxed for 3 days. The solvent was removed in vacuo affording a yellow crystalline solid that was used without further purification.

Amine Octamer. To a 50 mL schlenk flask with stirbar under argon Imine Octamer (314 mg, 0.14 mmol) was added. Next anhydrous THF (15 mL) and MeOH (6.4 mL) were added via syringe under argon and the suspension stirred at room temperature. To the homogeneous solution, $NaBH_4$ (136 mg, 3.6 mmol) was added in portions and the mixture stirred at room temperature for 12 h. The solution was filtered, followed by addition of 19.9 mL $H_2O$. The pH was adjusted to ca. 2 by addition of 4 M HCl, then 6.8 mL of an ethylenediamine tetraaceticacid disodium salt dihydrate (0.13 M in $H_2O$) was added and the mixture stirred for 5 min. To the solution, 2.0% ammonium hydroxide was added and stirring continued for an additional 5 min. The solution was extracted with ethyl acetate (3×100 mL) the organic layer separated, dried over $Na_2SO_4$ and the solvent removed via rotoevaporation affording a pale yellow solid. Recrystallization from chloroform and hexanes afforded the Amine Octamer. Molecular weight was confirmed by ESIMS M+H=experimental=2058.7 m/z, calcd=2058.7 m/z.

Example 52

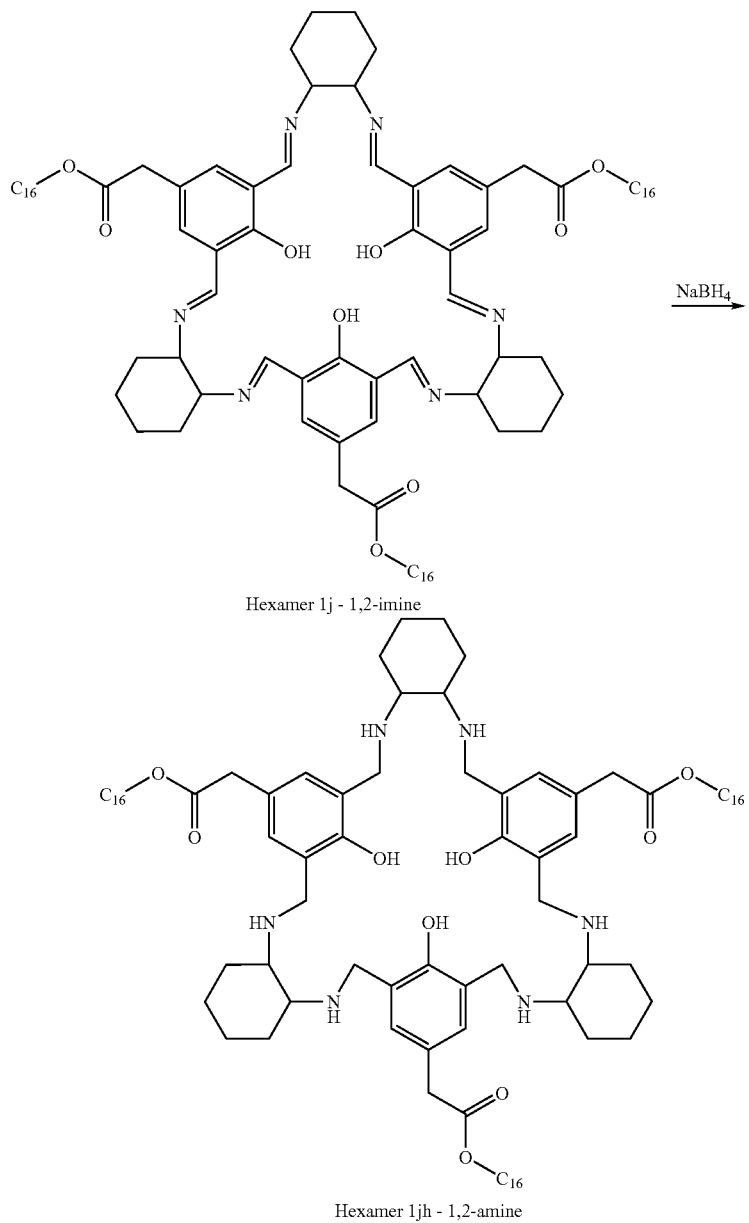

Hexamer 1j - 1,2-imine

Hexamer 1jh - 1,2-amine

Hexamer 1j. The two substrates, (−)-R,R-1,2-trans-diaminocyclohexane (0.462 mmol, 0.053 g) and 2,6-diformyl-4-hexadecyl benzylphenol carboxylate (0.462 mmol, 0.200 g) were added to a 10 mL vial containing a magnetic stirbar followed by the addition of 2 mL of $CH_2Cl_2$. The yellow solution was stirred at room temperature. After 24 h the reaction solution was plugged through silica gel with diethyl ether, and the solvent removed via roto-evaporation. (232 mg; 98% yield). $^1$H NMR (400 MHz, $CDCl_3$): δ 14.11 (s, 3H, OH), 8.67 (s, 3H, CH=N), 8.23 (s, 3H, CH=N), 7.70 (s, 3H, ArH), 7.11 (s, 3H, ArH), 4.05-3.90 (t, 6 H, $^3J$=6.6 Hz, $CH_2C(O)OCH_2(CH_2)_{14}CH_3$), 3.44 (s, 6 H, $CH_2C(O)OCH_2(CH_2)_{14}CH_3$), 3.30-3.42 (m, 6 H, $CH_2$—CH—N), 1.21-1.90 (m, 108 H, aliphatic) 0.92-0.86 (t, 9H, $^3J$=6.6 Hz. ESIMS (+) Calcd for $C_{96}H_{151}N_6O_9$: 1533; Found: 1534 $[M+H]^+$.

Hexamer 1jh. To a 100 mL pear-shaped flask with magnetic stirbar under argon, Hexamer 1j (0.387 mmol, 0.594 g) was added and dissolved in THF:MeOH (7:3, 28:12 mL, respectively). Next, $NaBH_4$ (2.32 mmol, 0.088 g) was added slowly in portions at room temperature for 6.5 h. The solvent was removed by roto-evaporation, the residue dissolved in 125 mL ethyl acetate and washed 3×50 mL of $H_2O$. The organic layer was separated, dried over $Na_2SO_4$ and the solvent removed by roto-evaporation. The resulting residue was recrystallized from $CH_2Cl_2$ and MeOH affording a white solid (0.440 g; 74% yield). 1H NMR (400 MHz, $CDCl_3$): δ 6.86 (s, 6 H, ArH), 4.10-4.00 (t, 6 H, $^3J$=6.6 Hz, $CH_2C(O)OCH_2(CH_2)_{14}CH_3$), 3.87-3.69 (dd, 6H, $^3J$=13.7 Hz, $^3J$(CNH)=42.4 Hz $CH_2$—CH—N), 3.43 (s, 6 H, $CH_2C(O)OCH_2(CH_2)_{14}CH_3$), 2.40-2.28 (m, 6 H, aliphatic), 2.15-1.95 (m, 6 H, aliphatic), 1.75-1.60 (m, 6 H, aliphatic), 1.60-1.55

(m, 6 H, aliphatic) 1.37-1.05 (m, 84 H, aliphatic) 0.92-0.86 (t, 9H, $^3J$=6.8 Hz. ESIMS (+) Calcd for $C_{96}H_{163}N_6O_9$: 1544; Found: 1545 [M+H]$^+$.

Example 53

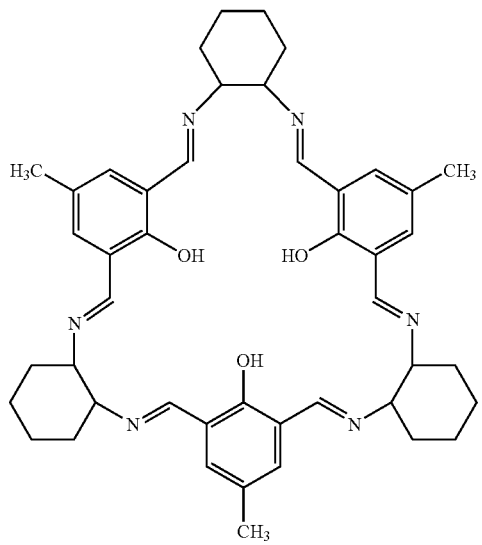

Hexamer 1a-Me-1,2-imine

Hexamer 1A-Me. A solution of 2-hydroxy-5-methyl-1,3-benzenedicarboxaldehye (53 mg, 0.32 mmol) in dichloromethane (0.6 mL) was added to a solution of (1R,2R)-(–)-1,2-diaminocyclohexane (37 mg, 0.32 mmol) in dichloromethane (0.5 mL). The mixture was stirred at ambient temperature for 16 h, added dropwise to methanol (75 mL) and chilled (4° C.) for 4 h. The precipitate was collected to afford 71 mg (92%) of hexamer 1A-Me. $^1$H NMR (CDCl$_3$): δ 13.88 (s, 3H, OH), 8.66 (s, 3H, ArCH=N), 8.19 (s, 3H, ArCH=N), 7.52 (d, 3H, J=2 Hz, Ar H), 6.86 (d, 3H, J=2 Hz, Ar H), 3.35 (m, 6H, cyclohexane 1,2-H's), 2.03 (3, 9H, Me), 1.6-1.9 (m, 18H, cyclohexane 3,6-H$_2$ and 4$_{eq}$,5$_{eq}$-H's), 1.45 (m, 6H, cyclohexane 4$_{ax}$,5$_{ax}$-H's); $^{13}$C NMR δ 63.67, 159.55, 156.38, 134.42, 129.75, 127.13, 119.00, 75.68, 73.62, 33.68, 33.41, 24.65, 24.57, 20.22; ESI (+) MS m/e (%) 727 M+H (100); IR 1634 cm$^{-1}$.

The claimed invention is:

1. A macrocyclic module of the formula:

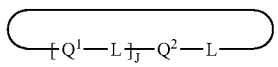

wherein:

J is 2-23;

Q$^1$ are synthons each independently selected from (a) phenyl synthons coupled to linkages L at 1,2-phenyl positions, (b) phenyl synthons coupled to linkages L at 1,3-phenyl positions, and (c) cyclohexane synthons coupled to linkages L at 1,2-cyclohexyl positions; wherein each ring position of each Q$^1$ not coupled to a linkage L is independently substituted with hydrogen or a functional group;

Q$^2$ is a cyclohexane synthon coupled to linkages L at 1,2-cyclohexyl positions; wherein each ring position of Q$^2$ not coupled to an L is independently substituted with hydrogen or a functional group, and wherein at least one of the ring positions of Q$^1$ or Q$^2$ that is not coupled to an L is substituted with a lipophilic moiety independently selected from -(8C-28C)alkyl, —O(8C-28C)alkyl, —NH(8C-28C)alkyl, —OC(O)-(8C-28C)alkyl, —C(O)O-(8C-28C)alkyl, —NHC(O)-(8C-28C)alkyl, C(O)NH-(8C-28C)alkyl, —CH=CH-(8C-28C)alkyl and —C≡C-(8C-28C)alkyl, each of which groups optionally being interrupted within the (8C-28C)alkyl portion of the group by one or more —S—, double bond, triple bond or —SiR'R"— groups, and optionally being substituted within the (8C-28C)alkyl portion of the group with one or more fluorine atoms, and wherein R' and R" are independently selected from (1C-18C)alkyl; wherein each functional group is independently selected from —C(O)F, —C(O)O-4-nitrophenyl, —C(O)O-pentafluorophenyl, —C(O)O-N-hydroxysuccinimide, a lipophilic group, —OH, —C(O)OH, —C(O)H, —C(O)OCH$_3$, —C(O)Cl, —NRR, —NRRR$^+$A$^-$, -MgX, -Li, -OLi, —OK, —ONa, —SH, —C(O)(CH$_2$)$_2$C(O)OCH$_3$, —NH-alkyl-C(O)CH$_2$CH(NH$_2$)CO$_2$-alkyl, —CH=CH$_2$, —CH=CHR, —CH=CR$_2$, 4-vinylaryl, —C(O)CH=CH$_2$, —NHC(O)CH=CH$_2$, —

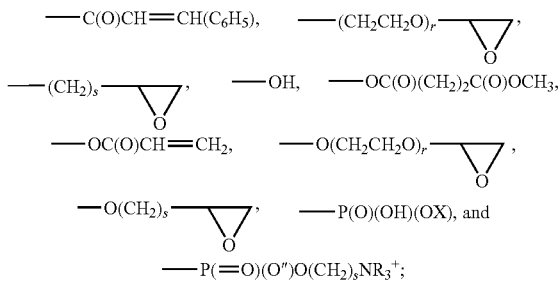

wherein R are each independently selected from hydrogen and (1C-6C)alkyl; X is selected from Cl, Br, and I; A$^-$ is an anion; r is 1-50; and s is 1-4; and L are linkages between the synthons each independently selected from —NHC(O)—, —CH=N—, and —CH$_2$NH— wherein linkages L are each independently configured in either of two possible configurations, forward and reverse, with respect to the synthons it couples together, if the two configurations are different structures.

2. The macrocyclic module of claim 1 having the formula:

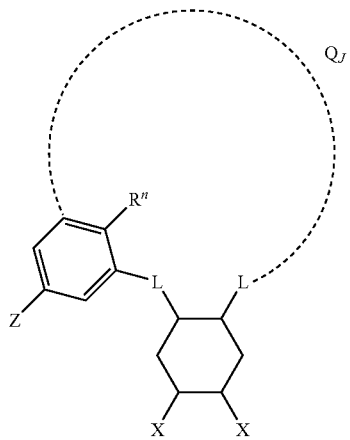

wherein: Q is 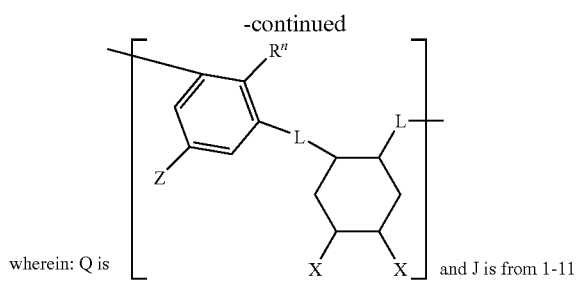 and J is from 1-11

X and R″ are each independently selected from hydrogen, —C(O)F, —C(O)O-4-nitrophenyl, —C(O)O-pentafluorophenyl, —C(O)O—N-hydroxysuccinimide, —OH, —C(O)OH, —C(O)H, —C(O)OCH$_3$, —C(O)Cl, —NRR, —NRRR$^+$A$^-$, -MgX', -Li, —OLi, —OK, —ONa, —SH, —C(O)(CH$_2$)$_2$C(O)OCH$_3$, —NH-alkyl-C(O)CH$_2$CH(NH$_2$)CO$_2$-alkyl, —CH=CH$_2$, —CH=CHR, —CH=CR$_2$, 4-vinylaryl, —C(O)CH=CH$_2$, —NHC(O)CH=CH$_2$, —C(O)CH=CH(C$_6$H$_5$),

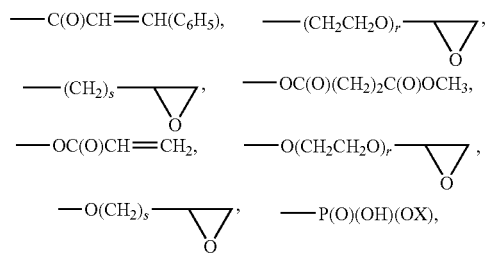

and —P(=O)(O)O(CH$_2$)$_s$NR$_3^+$; wherein R are each independently selected from hydrogen and (1C-6C)alkyl; X is selected from the group consisting of Cl, Br, and I; A$^-$ is an anion; r is 1-50; s is 1-4; and Z are each independently hydrogen or a lipophilic group, wherein at least one of Z is a lipophilic group independently selected from -(8C-28C)alkyl, —O(8C-28C)alkyl, —NH(8C-28C)alkyl, —OC(O)-(8C-28C)alkyl, —C(O)O-(8C-28C)alkyl, —NHC(O)-(8C-28C)alkyl, C(O)NH-(8C-28C)alkyl, —CH=CH-(8C-28C)alkyl and —C≡C-(8C-28C)alkyl, each of which groups optionally being interrupted within the (8C-28C)alkyl portion of the group by one or more —S—, double bond, triple bond or —SiR'R″— groups, and optionally being substituted within the (8C-28C)alkyl portion of the group with one or more fluorine atoms, and wherein R' and R″ are independently selected from (1C-18C)alkyl.

3. The macrocyclic module of claim 1, wherein J is 3.

4. The macrocyclic module of claim 1, wherein J is 5.

5. The macrocyclic module of claim 1, wherein J is 7.

6. The macrocyclic module of claim 1, wherein Q$^1$ is a phenyl synthon coupled to linkages L at the 1,3-phenyl positions.

7. The macrocyclic module of claim 6, wherein Q$^1$ is substituted with one lipophilic group.

8. The macrocyclic module of claim 1, wherein L is —NHC(O)—.

9. The macrocyclic module of claim 1, wherein L is —CH=N—.

10. The macrocyclic module of claim 1, wherein L is —CH$_2$NH—.

11. The macrocyclic module of claim 1, which is selected from the following structures:

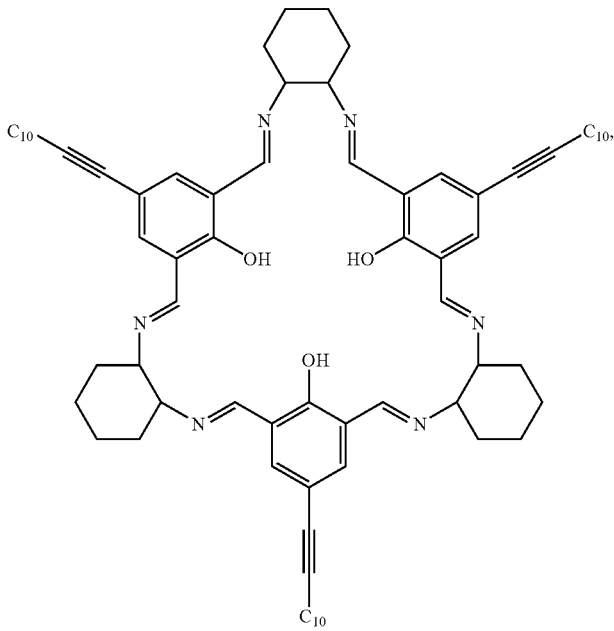

-continued
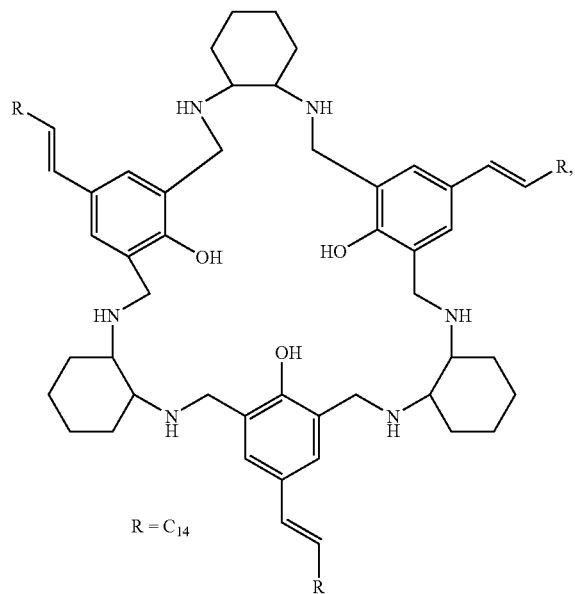
R = C₁₄
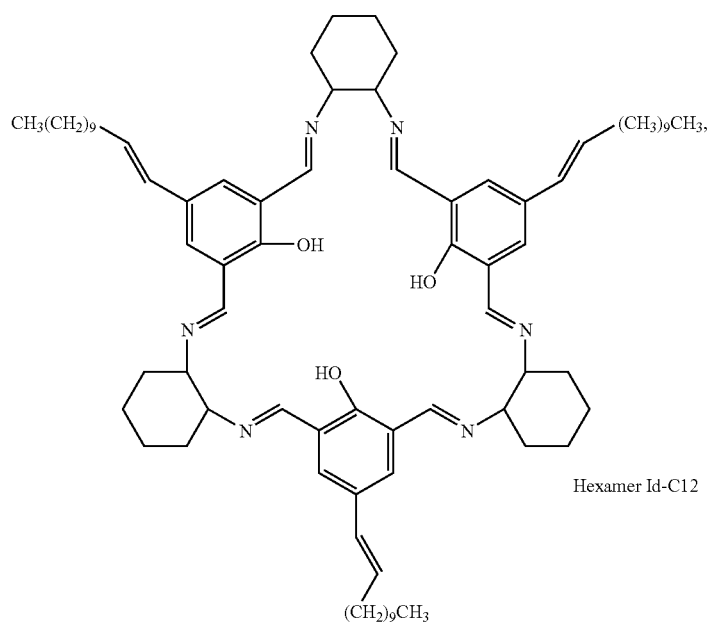
Hexamer Id-C12

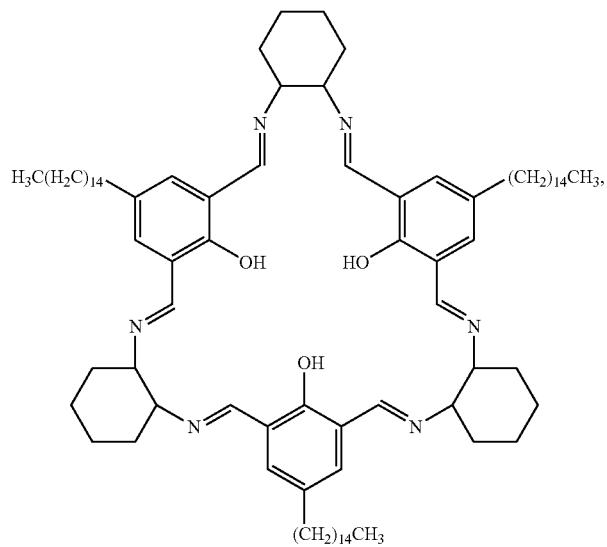
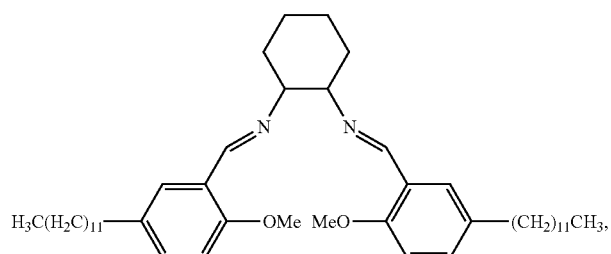
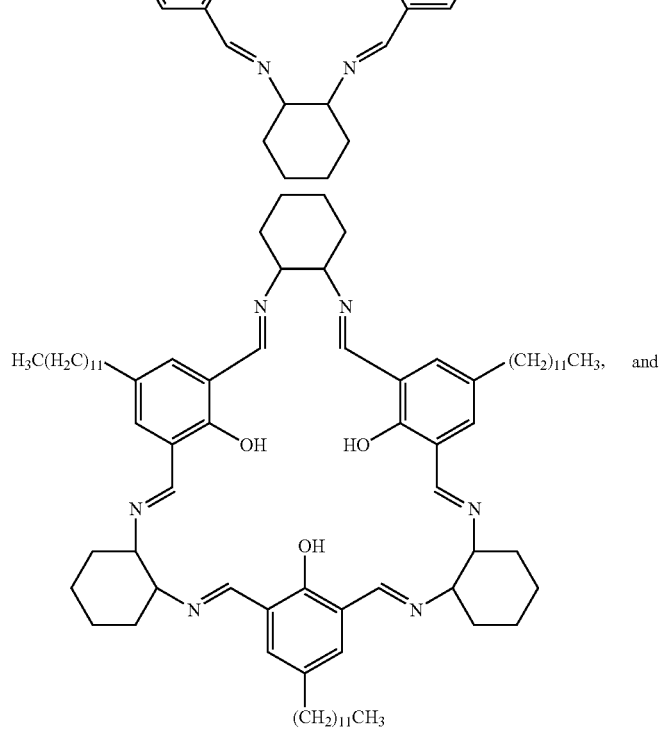

-continued
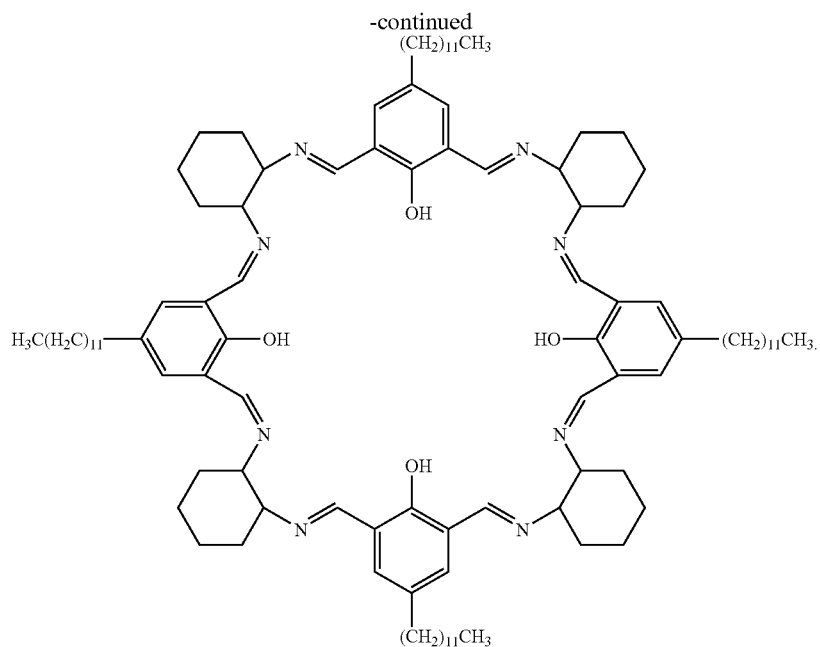
* * * * *